US009303078B2

(12) United States Patent
Garcia et al.

(10) Patent No.: US 9,303,078 B2

(45) Date of Patent: Apr. 5, 2016

(54) NUCLEIC ACID MOLECULES AND METHODS FOR EXCHANGING EXON(S) BY TRANSSPLICING

(75) Inventors: Luis Garcia, Bailly (FR); Stéphanie Lorain, Vincennes (FR)

(73) Assignees: ASSOCIATION INSTITUT DE MYOLOGIE, Paris (FR); CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); UNIVERSITE PIERRE ET MARIE CURRIE (PARIS 6), Paris (FR)

( * ) Notice: Subject to any disclaimer, the term of this patent is extended or adjusted under 35 U.S.C. 154(b) by 840 days.

(21) Appl. No.: 13/500,612

(22) PCT Filed: Oct. 8, 2010

(86) PCT No.: PCT/EP2010/065142

§ 371 (c)(1), (2), (4) Date: Jun. 13, 2012

(87) PCT Pub. No.: WO2011/042556

PCT Pub. Date: Apr. 14, 2011

(65) Prior Publication Data

US 2012/0245220 A1 Sep. 27, 2012
US 2013/0065948 A2 Mar. 14, 2013

Related U.S. Application Data

(60) Provisional application No. 61/249,702, filed on Oct. 8, 2009.

(51) Int. Cl.

| | |
|---|---|
| ***C12N 15/00*** | (2006.01) |
| ***C12N 5/00*** | (2006.01) |
| ***C07K 14/47*** | (2006.01) |
| ***A61K 48/00*** | (2006.01) |
| ***C12N 15/85*** | (2006.01) |

(52) U.S. Cl.

CPC ........... *C07K 14/4708* (2013.01); *A61K 48/005* (2013.01); *C12N 15/85* (2013.01); *C12N 2840/445* (2013.01); *C12N 2840/85* (2013.01)

(58) Field of Classification Search

USPC ............................................... 435/320.1, 320

See application file for complete search history.

(56) References Cited

U.S. PATENT DOCUMENTS

| | | | |
|---|---|---|---|
| 6,013,487 | A | 1/2000 | Mitchell |
| 6,083,702 | A | 7/2000 | Mitchell et al. |
| 6,280,978 | B1 | 8/2001 | Mitchell et al. |
| 2002/0193580 | A1 | 12/2002 | Mitchell et al. |

FOREIGN PATENT DOCUMENTS

| | | | |
|---|---|---|---|
| EP | 2 151 248 | 2/2010 | |
| EP | 2151248 | 10/2010 | |
| WO | 2004/050680 | 6/2004 | |
| WO | WO2006119137 A1 * | 11/2006 | ............. C07H 21/02 |

OTHER PUBLICATIONS

Human DMD Exon 23 sequence, EMBL-ENA, Accession No. L05636, Aug. 21, 1995.*
Seth et al, J Biol Chem, 2008, 283:10058-10067.*
International Search Report for PCT/EP2010/065142 Mailed Jan. 20, 2011.
International Search Report based on International Search Report PCT/EP2010/065142; mailed Jan. 20, 2011.
Chao et al.; "Phenotype correction of hemophilia A mice by spliceosome-mediated RNA trans-splicing"; Nature Medicine; Aug. 2003; vol. 9; No. 8; pp. 1015-1019; Nature Publishing Group.
Charrier et al.; "A lentiviral vector encoding the human Wiskott-Aldrich syndrome protein corrects immune and cytoskeletal defects in WASP knockout mice"; Gene Therapy; 2005; vol. 12; pp. 597-606; Nature Publishing Group.
Chiara et al.; "A two-step mechanism for 5' and 3' splice-site pairing"; Nature; Jun. 8, 1995; vol. 375; pp. 510-513.
Coady et al.; "Development of a Single Vector System that Enhances Trans-Splicing of SMN2 Transcripts"; PLoS ONE; Oct. 2008; vol. 3; Issue 10; pp. 1-11.
Denti et al.; "Body-wide gene therapy of Duchenne muscular dystrophy in the mdx mouse model"; PNAS; Mar. 7, 2006; vol. 103; No. 10; The National Academy of Sciences of the USA; pp. 3758-3763.
Dingwall et al.; "Protein Import Into the Cell Nucleus"; Ann. Rev. Cell Biol.; 1986; vol. 2; pp. 367-390; Annual Reviews Inc.
Edom et al.; "Clones of Human Satellite Cells Can Express in Vitro both Fast and Slow Myosin Heavy Chains"; Development 21 Biology; 1994; vol. 164; pp. 219-229; Academic Press, Inc.

(Continued)

*Primary Examiner* — Michael Wilson

(74) *Attorney, Agent, or Firm* — Miles & Stockbridge P.C.

(57) ABSTRACT

The present invention provided methods and compositions for generating novel nucleic acid molecules through targeted spliceosome mediated simple or double trans-splicing. The compositions of the invention include pre-trans-splicing molecules (PTMs) designed to interact with a target precursor messenger RNA molecule (target pre-mRNA) and to mediate a simple or double trans-splicing reaction resulting in the generation of a novel chimeric RNA molecule (Chimeric RNA).

22 Claims, 6 Drawing Sheets

(56) References Cited

OTHER PUBLICATIONS

Eul et al.; "Experimental evidence for RNA trans-splicing in mammalian cells"; The EMBO Journal; 1995; vol. 14; No. 13; pp. 3226-3235; Oxford University Press.
Finta et al.; "Intergenic mRNA Molecules Resulting from trans-splicing"; The Journal of Biological Chemistry; 2002; vol. 277; No. 8; pp. 5882-5890; The American Society for Biochemistry and Molecular Biology, Inc.
Goyenvalle et al.; "Rescue of Dystrophic Muscle Through U7 snRNA-Mediated Exon Skipping"; Science; Dec. 3, 2004; vol. 306; pp. 1796-1799.
Kierlin-Duncan et al.; "Using 5'-PTMs to repair mutant Beta-globin transcripts"; RNA; 2007; vol. 13; pp. 1317-1327; RNA Society.
Liu et al.; "Spliceosome-Mediated RNA Trans-Splicing with Recombinant Adeno-Associated Virus Partially Restores Cystic Fibrosis Transmembrane Conductance Regulator Function to Polarized Human Cystic Fibrosis Airway Epithelial Cells"; Human Gene Therapy; Sep. 2005; vol. 16; pp. 1116-1123.
Mansfield et al.; "Repair of CFTR mRNA by spliceosome-mediated RNA trans-splicing"; Gene Therapy; 2000; vol. 7; pp. 1885-1895; Macmillian Publishers.
McCarthy et al.; "Characterization of an intron splice enhancer that regulates alternative splicing of human GH pre-mRNA"; Human Molecular Genetics; 1998; vol. 7; No. 9; pp. 1491-1496; Oxford University Press.
Mouly et al.; "Plasticity of Human Satellite Cells"; Neuromusc. Disord; 1993; vol. 3; Nos. 5/6; pp. 371-377; Elsevier Science Ltd.
Shimizu et al.; "Immunoglobulin double-isotype expression by trans-mRNA in a human immunoglobin transgenic mouse"; Proc. Natl. Acad. Sci.; Oct. 1989; vol. 86; pp. 8020-8023.
Staley et al.; "Mechanical Devices of the Spliceosome: Motors, Clock, Springs, and Things"; Cell; Feb. 6, 1998; vol. 92; pp. 315-326; Cell Press.
Tacke et al.; "Determinants of SR protein specificity"; Current Opinion in Cell Biology; 1999; vol. 11; pp. 358-362; Elsevier Science Ltd.
Tahara et al.; "Trans-splicing repair of CD40 ligand deficiency results in naturally regulated correction of a mouse model of hyper-IgM X-linked immunodeficiency"; Nature Medicine; Aug. 2004; vol. 10; No. 8; Nature Publishing Group.
Horiuchi et al.; "Alternative trans-splicing: a novel mode of pre-mRNA processing"; Biol. Cell; 2006; vol. 98; pp. 135-140.
Vellard et al.; "A potential splicing factor is encoded by the opposite strand of the trans-spliced c-myb exon"; Proc. Natl. Acad. Sci.; Apr. 1992; vol. 89; pp. 2511-2515; Biochemistry.
Yokota et al.; "Efficacy of Systemic Morpholino Exon-Skipping in Duchenne Dystropy Dogs"; Ann Neurol; 2009; vol. 65; pp. 667-676; American Neurological Association.
Zufferey et al.; "Multiply attenuated lentiviral vector achieves efficient gene delivery in vivo"; Nature Biotechnology; Sep. 1997; vol. 15; pp. 871-875; Nature Publishing Group.
Puttaraju et al.; "Messenger RNA Repair and Restoration of Protein Function by Spliceosome-Mediated RNA Trans-Splicing"; Molecular Therapy; Aug. 2001; vol. 4; No. 2; pp. 105-114; The American Society of Gene Therapy.
Lorain et al.; "Trans-splicing approaches to repair Duchenne dystrophin transcripts"; Neuromusc; 2009; vol. 19; Nos. 8/9; p. 578; Abstract XP026395140.
Yuasa et al.; "Gene Therapy of Duchenne Muscular Dystrophy by Splicesome-Mediated RNA Trans-Splicing"; J. Gene Med.; Apr. 2008; vol. 10; p. 477; Abstract XP009142359; The 13th Annual Meeting 2007 Japan Society of Gene Therapy.
Lorain et al.; "Exon exchange approach to repair Duchenne dystrophin transcripts"; PLOS; May 2010; vol. 5; No. 5; pp. 1-15; Abstract XP002613584.
Lorain et al.; "Exon exchange approach to repair Duchenne dystrophin transcripts"; Neuromuscular Disorders; vol. 20; 2010; p. 639; Abstract XP027263796.
Garcia-Blanco; "Messenger RNA reprogramming by spliceosome-mediated RNA trans-splicing"; The Journal of Clinical Investigation; Aug. 2003; vol. 112; No. 4; pp. 474-480.
Wood et al.; "Modulating the Expression of Disease Genes with RNA-Based Therapy"; PLoS Genetics; Jun. 2007; vol. 3; Issue 6; pp. 845-854.
Garcia-Blanco et al.; "Alternative splicing in disease and therapy"; Nature Biotechnology; May 2004; vol. 22; No. 5; pp. 535-546.
Hengge; "SMaRT Technology Enables Gene Expression Repair in Skin Gene Therapy"; Journal of Investigative Dermatology; 2008; vol. 128; pp. 499-500; The Society for Investigative Dermatology.
Rodriguez-Martin; "Reprogramming of tau alternative splicing by spliceosome-mediated RNA trans-splicing: implications for tauopathies"; PNAS; Oct. 25, 2005; vol. 102; No. 43; pp. 15659-15664.
Wally et al.; "5' Trans-splicing Repair of the PLEC1 Gene"; Journal of Investigative Dermatology; 2008; vol. 128; pp. 568-574; The Society for Investigative Dermatology.
Zayed et al.; "Correction of DNA Protein Kinase Deficiency by Spliceosome-mediated RNA Trans-splicing and Sleeping Beauty Transposon Delivery"; Molecular Therapy; Jul. 2007; vol. 15; No. 7; pp. 1273-1279; The American Society of Gene Therapy.
Puttaraju et al.; "Spliceosome-mediated RNA trans-splicing as a tool for gene therapy"; Mar. 1999; vol. 17; pp. 246-252; Nature Biotechnology.
Mansfield et al.; "5' Exon replacement and repair by spliceosome-mediated RNA trans-splicing"; RNA; 2003; vol. 9; pp. 1290-1297; RNA Society.
Moore et al.; "Splicing of Precursors to mRNA by the Spliceosome"; The RNA World; 1993; pp. 303-358; Cold Spring Harbor Laboratory Press.
Coady et al.; "Development of a Single Vector System that Enhances Trans-Splicing of SMN2 Transcripts"; PLoSone; Oct. 2008; vol. 3; Issue 10; e3468; pp. 1-6.
Sambrook et al.; "Molecular Cloning: A Laboratory Manual"; 1989; Cold Spring Harbor Laboratory Press; 1449 pages.
V. Wally et al., "Spliceosome-Mediated Trans-Splicing: The Therapeuetic Cut and Paste." Journal of Investigative Dermatology (2012), vol. 132, pp. 1959-1966.
Y. Yang et al., "Spliceosome-Mediated RNA Trans-splicing." Molecular Therapy (2005) vol. 12, No. 6, pp. 1006-1012.

* cited by examiner

A

B

B

NUCLEIC ACID MOLECULES AND METHODS FOR EXCHANGING EXON(S) BY TRANSSPLICING

CROSS REFERENCE TO RELATED APPLICATIONS

This application is a §371 National Stage Application of PCT/EP2010/065142, filed Oct. 8, 2010, which claims priority to U.S. Provisional Application No. 61/249,702 filed Oct. 8, 2009.

BACKGROUND OF THE INVENTION

1. Field of the Invention

The present invention provides methods and compositions for generating novel nucleic acid molecules through targeted spliceosome mediated simple or double trans-splicing. The compositions of the invention include pre-trans-splicing molecules (PTMs, herein also called "TS molecule" for "Trans-Splicing molecules") designed to interact with a target precursor messenger RNA molecule (target pre-mRNA) and to mediate a simple or double trans-splicing reaction resulting in the generation of a novel chimeric RNA molecule (chimeric RNA). This approach enables to replace whole nucleotide sequences such as exonic sequences in a targeted mRNA and is therefore very interesting to address disorders caused by dominant mutations while preserving levels and tissue specificity. This RNA repair strategy is thus useful to replace mutated nucleic acid sequences into the normal ones and thereby treat many genetic disorders.

In particular, the PTMs of the present invention include those genetically engineered to interact with DMD target pre-mRNA so as to result in correction of DMD genetic defects responsible for the Duchenne muscular dystrophy (DMD).

The compositions of the invention further include recombinant vector systems capable of expressing the PTMs of the invention and cells expressing said PTMs. The methods of the invention encompass contacting the PTMs of the invention with a DMD target pre-mRNA under conditions in which a portion of the PTM is trans-spliced to a portion of the target pre-mRNA to form a mRNA molecule wherein the genetic defect in the DMD gene has been corrected. The methods and compositions of the present invention can be used in gene therapy for correction of neuromuscular disorders such as the Duchenne muscular dystrophy. The principle of this treatment can also be applied to any genetic disease where the pathogenic mutation involves an alteration of the transcript that can be corrected by simple or double trans-splicing.

2. Description of Related Art

DNA sequences in the chromosome are transcribed into pre-mRNAs which contain coding regions (exons) and generally also contain intervening non-coding regions (introns). Introns are removed from pre-mRNAs in a precise process called cis-splicing. Splicing takes place as a coordinated interaction of several small nuclear ribonucleoprotein particles (snRNPs) and many protein factors that assemble to form an enzymatic complex known as the spliceosome (Staley and Guthrie, 1998).

In most cases, the splicing reaction occurs within the same pre-mRNA molecule, which is termed cis-splicing. Splicing between two independently transcribed pre-mRNAs is termed trans-splicing. Trans-splicing was first discovered in trypanosomes and subsequently in nematodes, flatworms and in plant mitochondria, drosophila, mice an humans (Takayuki Horiuchi and Toshiro Aigaki, 2006).

The mechanism of splice leader trans-splicing, which is nearly identical to that of conventional cis-splicing, proceeds via two phosphoryl transfer reactions. The first causes the formation of a 2'-5' phosphodiester bond producing a 'Y' shaped branched intermediate, equivalent to the lariat intermediate in cis-splicing. The second reaction, exon ligation, proceeds as in conventional cis-splicing. In addition, sequences at the 3' splice site and some of the snRNPs which catalyze the trans-splicing reaction, closely resemble their counterparts involved in cis-splicing.

Trans-splicing may also refer to a different process, where an intron of one pre-mRNA interacts with an intron of a second pre-mRNA, enhancing the recombination of splice sites between two conventional pre-mRNAs. This type of trans-splicing was postulated to account for transcripts encoding a human immunoglobulin variable region sequence linked to the endogenous constant region in a transgenic mouse (Shimizu et al., 1989). In addition, trans-splicing of c-myb pre-RNA has been demonstrated (Vellard, M. et al. 1992) and more recently, RNA transcripts from cloned SV40 trans-spliced to each other were detected in cultured cells and nuclear extracts (Eul et al., 1995). However, naturally occurring trans-splicing of mammalian pre-mRNAs is thought to be a rare event (Finta, C. et al., 2002).

In vitro trans-splicing has been used as a model system to examine the mechanism of splicing by several. Reasonably efficient trans-splicing (30% of cis-spliced analog) was achieved between RNAs capable of base pairing to each other, whereas splicing of RNAs not tethered by base pairing was further diminished by a factor of 10. Other in vitro trans-splicing reactions not requiring obvious RNA-RNA interactions among the substrates were observed for example by Chiara & Reed (1995, Nature). These reactions occur at relatively low frequencies and require specialized elements, such as a downstream 5' splice site or exonic splicing enhancers.

SUMMARY OF THE INVENTION

The present invention relates to the use of targeted trans-splicing mediated by native mammalian splicing machinery, i.e., spliceosomes, to reprogram or alter the coding sequence of a targeted m-RNA.

A lot of studies have already described PTMs that can mediate "simple" trans-splicing, that is, a technology that enables to replace either the 3' part of a transcript, or, more rarely, the 5' part (Mansfield et al, 2003; Kierlin-Duncan & Sullenger, 2007). For example, U.S. Pat. Nos. 6,083,702, 6,013,487 and 6,280,978 describe the use of PTMs to mediate a "simple" trans-splicing reaction by contacting a target precursor mRNA to generate novel chimeric RNAs. Importantly, the "simple" trans-splicing technologies enable to correct a number of mutations using minigenes or endogenous transcripts in genetic disease context like hemophilia A (Chao et al., 2003), spinal muscular atrophy (Coady et al., 2008), X-linked immunodeficiency (Tahara et al., 2004) and cystic fibrosis where the widespread mutation CFTRAF508 was replaced efficiently in vivo by the normal sequence via a trans-splicing reaction (Liu et al., 2005).

As opposed to "simple" trans-splicing, "double" trans-splicing enables to replace or introduce a sequence, such as exonic sequences, in a targeted mRNA (herein called ExChange: concomitant 3' and 5' trans-splicing reactions). More precisely, double trans-splicing can modify a given or replace a missing exonic sequence within a given gene transcript while at the same time preserving the regulatory intronic sequences which are present 5' and 3' of the exonic sequence targeted by double trans-splicing, thereby allowing for alternative transcripts to occur. Conversely to conventional gene therapy, "double" trans-splicing approaches would be very interesting to address disorders caused by dominant mutations, while preserving levels and tissue specificity. Exon exchange (ExChange) using double trans-splicing, at both sides of a targeted exon, would have the advantage of minimizing exogenous material as well as preserving full regulatory elements potentially present in 5' and/or 3' untranslated domains of the rescued mRNA. As a RNA repair strategy, the ExChange approach will produce the corrected protein where it is naturally expressed. It has the supplementary advantage upon other RNA surgery strategies of correcting precisely the sequence defect without changing anything to the whole messenger sequence (i.e. the open reading frame and untranslated regions). Hence, the regulatory sequences present in 5' and 3' UTRs are preserved, something which never happens in classical gene therapy where cDNAs are amputated of their non coding sequences. These regions are now known to be essential for mRNA stability and translation regulation; in particular, they are targets for miRNAs which play important role in a variety of disease (Zhang & Farwell, 2008).

However no study has ever described so far an efficient PTM enabling to perform a "double" trans-splicing, that is a PTM containing both a 3' splice region and a 5' splice region and a nucleotide sequence to be inserted into a target mRNA. Furthermore, no study has ever demonstrated that such PTM might be able to replace with high efficiency a nucleotide sequence inside a target mRNA.

The herein presented results demonstrate for the first time an efficient PTM enabling high level of ExChange (i.e. concomitant 3' and 5' trans-splicing reactions), and therefore the possibility of rescuing mutated transcripts by specifically replacing a mutated exon by its normal version during a double trans-splicing reaction. By using the PTM presented in the present invention, one can obtain an ExChange efficiency that reaches a level of at least about 50%, for example 53%, of repaired transcripts with DMD minigene as target. Importantly, no non-specific end products were ever detected, suggesting that the chosen annealing sequences of the PTM did not decipher cryptic splicing site nor obstruct splicing events.

The trans-splicing technology uses a trans-splicing molecule that "tricks" the spliceosome into using it as a substrate for splicing. In the ExChange approach, the game is more "tricky" since the spliceosome must realize a double trans-splicing between the pre-messenger transcript and the PTM. After having tested various combinations of antisenses, it was found by the present inventors that the dogmas: i) blocking endogenous splicing signals on the nascent pre-mRNA transcript via base-pairing or ii) at the opposite, bringing the replacing exon closer to endogenous splice site to be joined, did not produce the best results, as shown in the present examples. Indeed, the best antisense for the first trans-splicing (3' replacement) matched with the middle of the first intron while the second one (5' replacement) was better when located close to the 3' end of the exon to be replaced.

DETAILED DESCRIPTION OF A PREFERRED EMBODIMENT

Figure Legends

Figure 1:
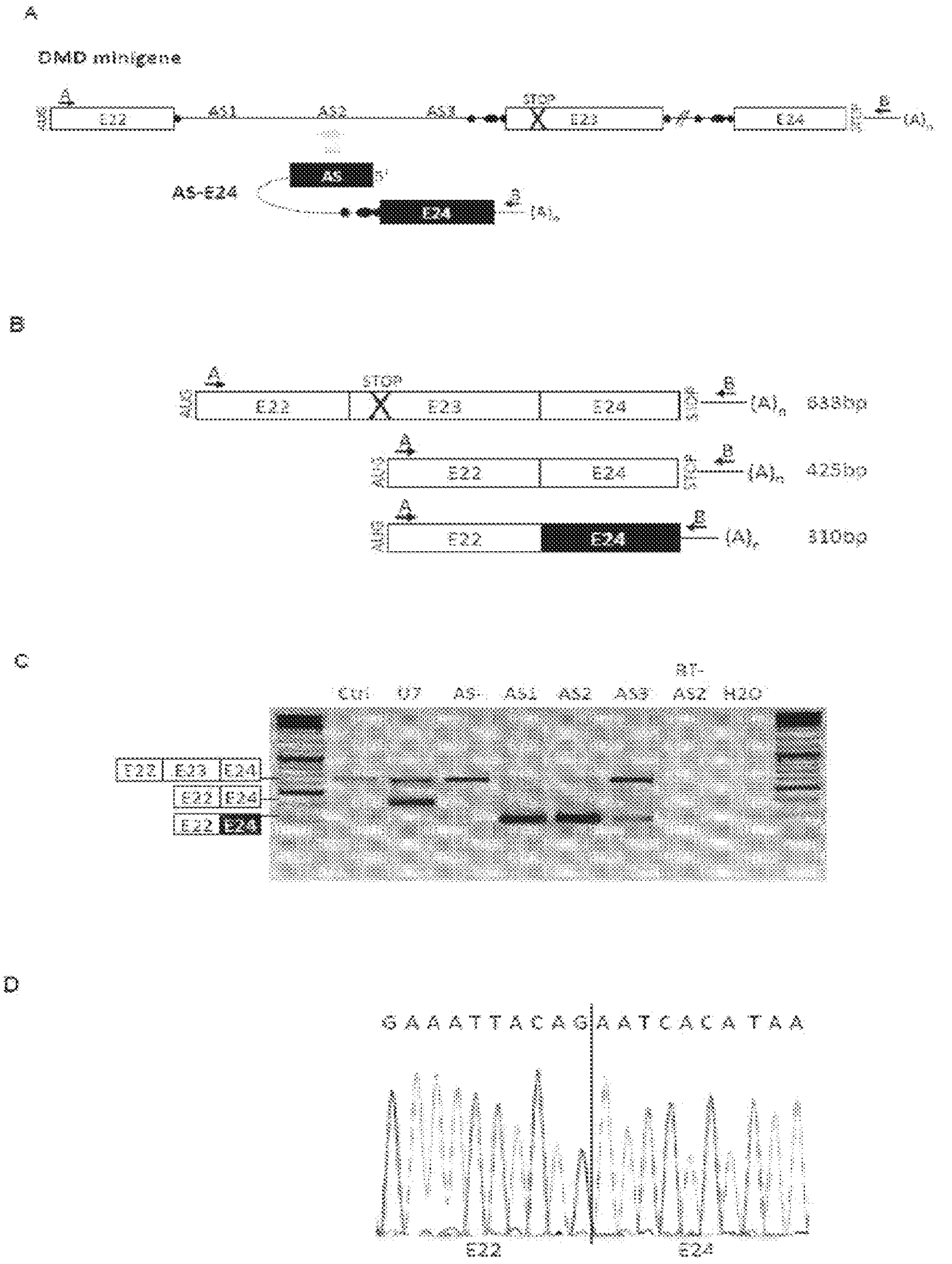
FIGS. 1-6 represent embodiments as described herein.

The FIG. 1 Exposes the Trans-Splicing Strategy for the 3' Replacement:

(A) Exons 22 to 24 (boxes E22 to E24) with natural introns (lines with black balls illustrating the splice sites) on the DMD minigene. The cross represents the nonsense mdx mutation in E23. The trans-splicing (TS) molecule AS-E24 comprises a 150 nt antisense sequence (AS) complementary to intron 22 as well as a spacer, a strong conserved yeast branch point sequence, a polypyrimidine tract, a 3' acceptor site (the three last elements are represented as blacks balls) and E24. TS constructs were made with three different antisense sequences, AS1 to AS3. Arrows indicate the positions of the forward A and reverse B PCR primers in the minigene and the TS molecule. (B) Expected transcripts generated by cis-splicing (E23 inclusion and skipping) and trans-splicing, and the predicted sizes of the corresponding PCR amplification products detected using the RT-PCR strategy illustrated in (A). (C) RT-PCR analysis using PCR primers A and B of NIH3T3 cells cotransfected with DMD minigene and constructions pSMD2-GFP (Ctrl), pSMD2-U7-SD23-BP22 (U7), pSMD2-E24 (AS-), pSMD2-AS1-E24 (AS1), pSMD2-A52-E24 (AS2) and pSMD2-A53-E24 (AS3). RT-AS2: samples containing DMD minigene and pSMD2-A52-E24 without reverse transcription; H2O: PCR negative control. (D) An exact E22-E24 junction was confirmed by sequencing of the 310 bp product.

Figure 2:
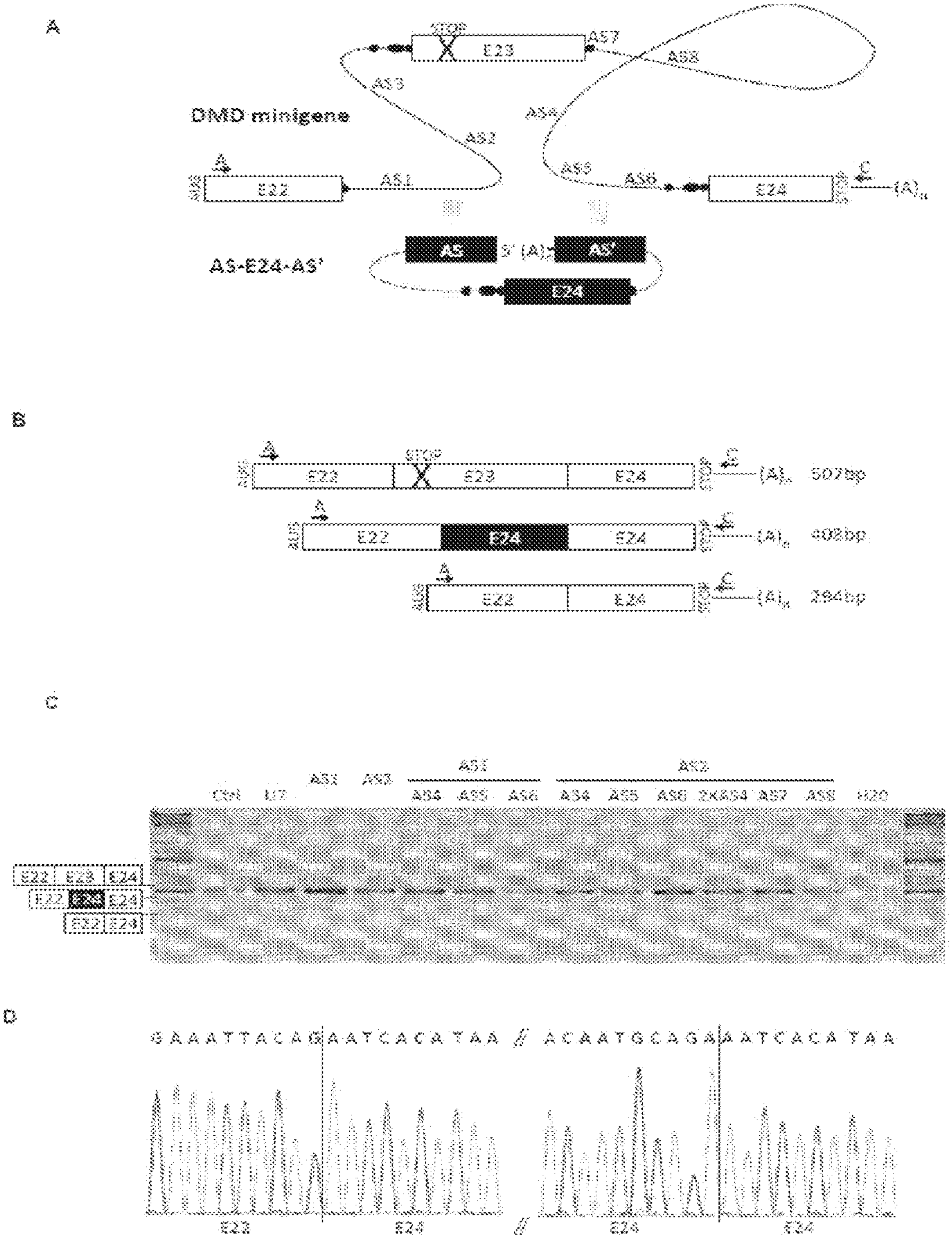

The FIG. 2 Shows the Exon Replacement Approach on DMD Reporter Transcripts.

(A) The exon exchange molecule (EX) AS-E24-AS' comprises the same elements as the TS molecule (see FIG. 1A) followed by a 5' donor site (black ball) and a second antisens sequence (AS') of 150 nt complementary to intron 23. EX constructs were made with five different AS' antisense sequences, AS4 to AS8. Arrows indicate the positions of the forward A and reverse C PCR primers in the minigene. (B) Expected transcripts generated by cis-splicing (E23 inclusion and skipping) and exon exchange, and predicted sizes of the corresponding PCR amplification products detected using the RT-PCR strategy illustrated in (A). (C) RT-PCR analysis using primers A and C of NIH3T3 cells cotransfected with DMD minigene and constructions pSMD2-GFP (Ctrl), pSMD2-U7-SD23-BP22 (U7), the TS constructions pSMD2-AS1-E24 (AS1), pSMD2-AS2-E24 (AS2) and EX molecules pSMD2-AS-E24-AS' containing AS1 or AS2 and AS4 to AS8. AS2-2XAS4, EX plasmid pSMD2-AS2-E24-2×AS4 containing two AS4 copies; H20: PCR negative control. (D) Accurate E22-E24 and E24-E24 junctions were confirmed by sequencing of the 408 bp product.

Figure 3:
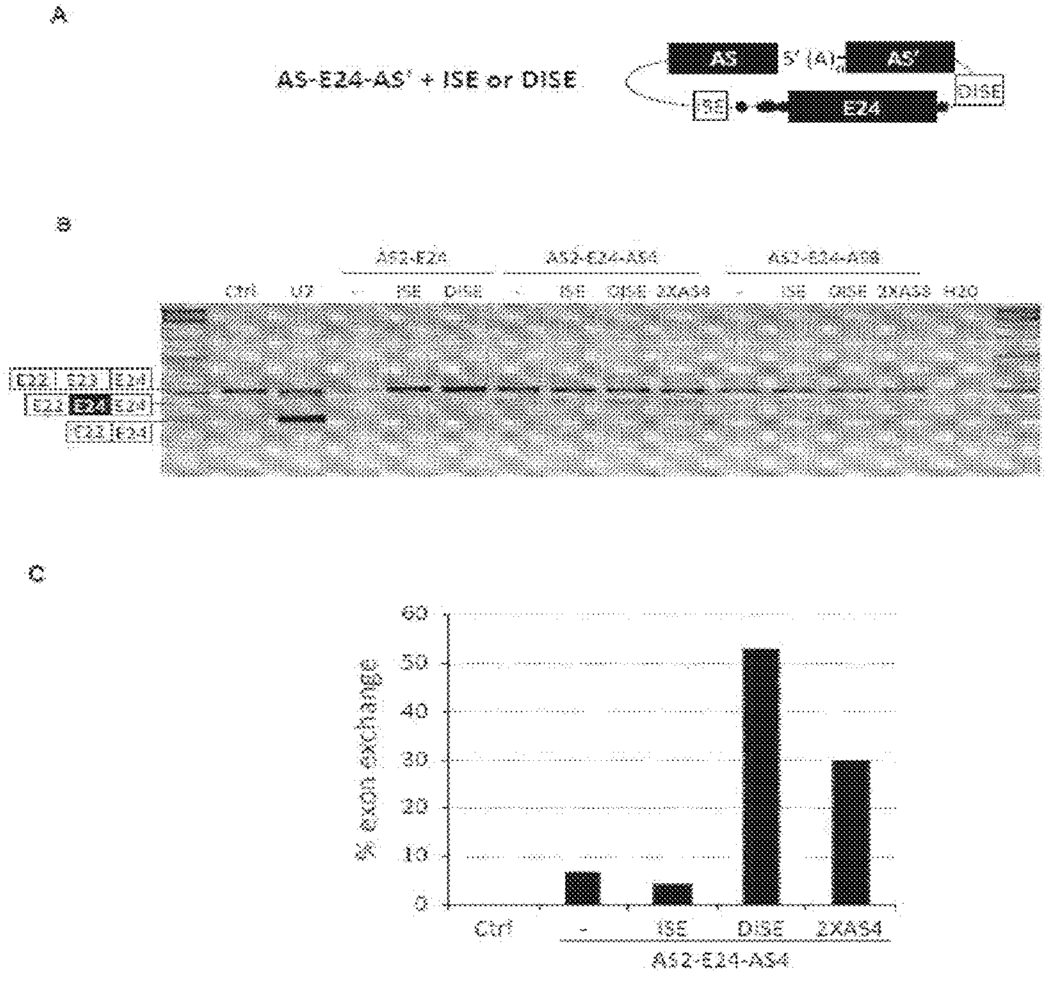

The FIG. 3 Shows the Effect of Intronic Splice Enhancer Sequences on Exon Replacement Efficiency.

(A) Exon exchange molecules AS-E24-AS' with intronic splice enhancers ISE or DISE sequences. (B) RT-PCR analysis using primers A and C of NIH3T3 cells cotransfected with DMD minigene and constructs pSMD2-GFP (Ctrl), pSMD2-U7-SD23-BP22 (U7) and the following EX plasmids with AS4 or AS8: pSMD2-AS2-E24-AS' (–), pSMD2-AS2-ISE-E24-AS' (ISE), pSMD2-AS2-E24-DISE-AS' (DISE) and pSMD2-AS2-E24-2XAS' (2XAS'). H20: PCR negative control. (C) Efficiency of DMD exon exchange induced by AS4 containing EX molecules analyzed by absolute quantitative real-time RT-PCR.

Figure 4:
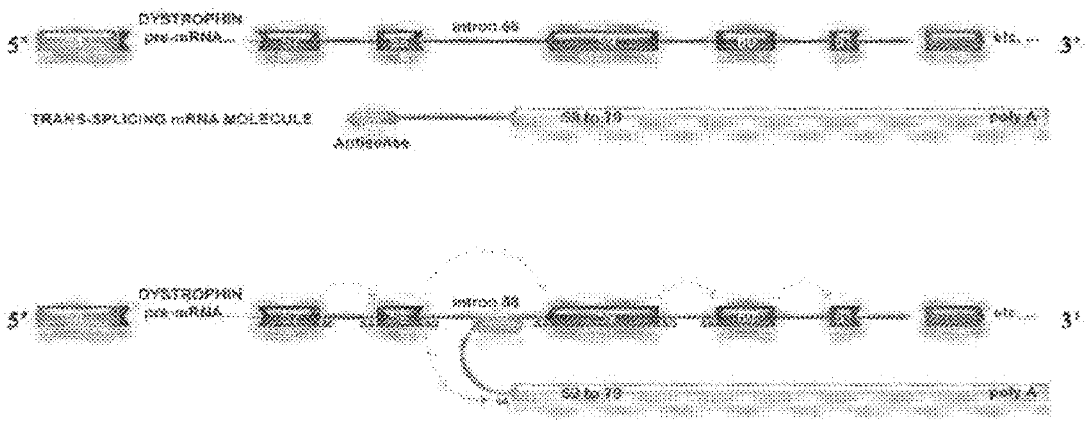

The FIG. 4 Shows the Trans-Splicing Strategy for Dystrophin Transcript Repair with the Simple Transsplicing Molecule of the Invention SEQ ID No 71 (Example 2)

The endogenous pre-messenger dystrophin transcript is illustrated on the top with boxes representing exons, and black lines representing introns. The trans-splicing mRNA molecule (second line) comprise a 150 nt antisense sequence complementary to intron 58 of the DMD gene as well as a spacer, a strong conserved yeast branch point sequence (BP), a polypyrimidine tract (PPT), a 3' splice acceptor (SA) and the normal human dystrophin cDNA from exon 59 to the exon 79 STOP codon.

Figure 5:
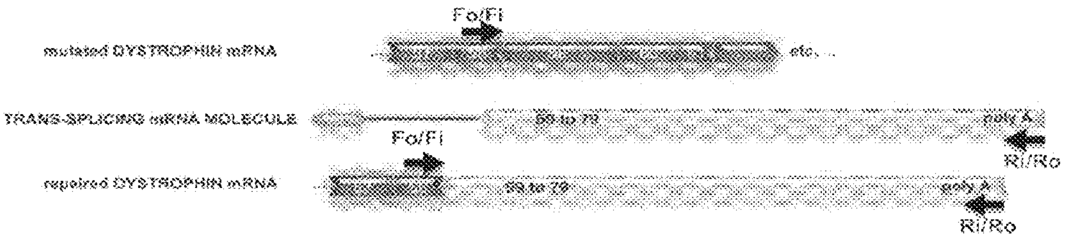
Figure 5:
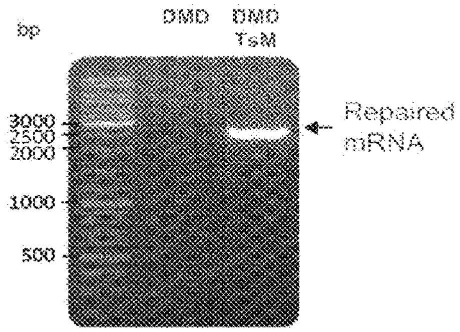

The FIG. 5 Shows the Detection of Repaired Dystrophin Transcripts with the Simple Transsplicing Molecule of the Invention SEQ ID No 71 (Example 2)

(A) Mutated dystrophin mRNA is represented on the top, as well as the trans-splicing mRNA molecule SEQ ID NO: (second line), and expected dystrophin transcripts generated by cis-splicing and trans-splicing (third line). Arrows indicate the positions of the forward Fo/Fi and reverse Ro/Ri PCR primers designed to detect only the repaired dystrophin cDNA by generating a 2443 bp PCR product. (B) RT-PCR analysis using PCR primers Fo/Fi and Ro/Ri of total RNAs extracted from patient myotubes (DMD) transduced by lentivirus expressing the simple trans-splicing mRNA molecules (TsM). Lane "–": DMD non transduced myotubes.

Figure 6:
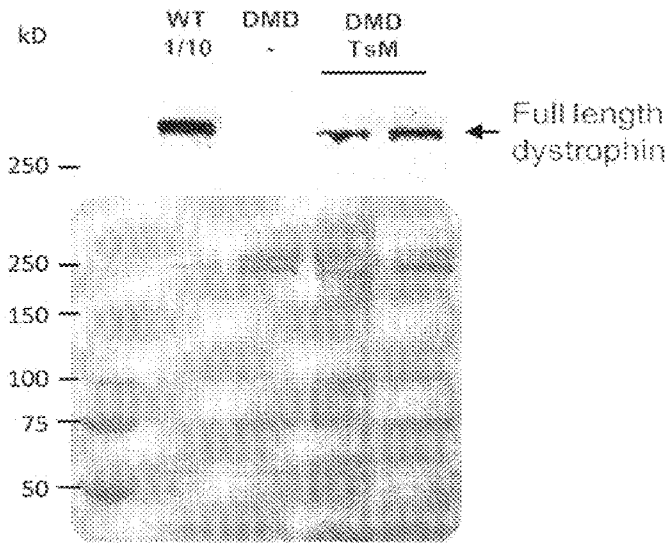

The FIG. 6 Shows the Dystrophin Rescue in DMD Cells Using the Simple Transsplicing Molecule of the Invention SEQ ID No 71 (Example 2)

Western blot of total protein extracted from DMD patient myotubes transduced by lentivirus expressing the TSM molecules, stained with the NCL-DYS1 monoclonal antibody. The full-length 427 kD dystrophin is indicated as detected in normal CHQ myotubes sample (WT). Lane "–": DMD non transduced myotubes. Each lane was loaded with 50 μg of total protein except Ctrl, 5 μg. Red panel: visualization of total proteins present on the same membrane by Ponceau red staining.

In a first aspect, the present invention is drawn to a nucleic acid molecule comprising:

a) two target binding domains AS and AS' that target the binding of the nucleic acid molecule to a target pre-mRNA, wherein the two target binding domains AS and AS' are located respectively at the 5'-end and at the 3'-end of the nucleic acid molecule, b) a 3' splice region comprising a branch point, a polypyrimidine tract and a 3' splice acceptor site, c) a 5' splice region comprising a 5' splice donor site, d) a spacer sequence that separates the 3' splice region from the 5'-end target binding domain AS, e) a spacer sequence that separates the 5' splice region from the 3'-end target binding domain AS', and f) a nucleotide sequence to be trans-spliced to the target pre-mRNA, wherein said nucleotide sequence encodes at least a part of a normal polypeptide, and is located between the 3' splice region and the 5' splice region of said nucleic acid.

This nucleic acid molecule is hereafter referred to as "double trans-splicing molecule", or "double PTM" of the invention.

Preferably, said nucleic acid molecule comprises:

a) two target binding domains AS and AS' that target binding of the nucleic acid molecule to the pre-mRNA of the dystrophin gene (DMD), wherein the two target binding domains AS and AS' are located respectively at the 5'-end and at the 3'-end of the nucleic acid molecule, b) a 3' splice region comprising a branch point, a polypyrimidine tract and a 3' splice acceptor site, c) a 5' splice region comprising a 5' splice donor site, d) a spacer sequence that separates the 3' splice region from the 5'-end target binding domain AS, e) a spacer sequence that separates the 5' splice region from the 3'-end target binding domain AS', and f) a nucleotide sequence to be trans-spliced to the target pre-mRNA of the dystrophin gene (DMD), wherein said nucleotide sequence encodes at least a part of the normal dystrophin polypeptide, and is located between the 3' splice region and the 5' splice region of said nucleic acid.

In a second aspect, the present invention is drawn to a nucleic acid molecule comprising:

a) one target binding domain (AS) that target binding of the nucleic acid molecule to the pre-mRNA of the dystrophin gene (DMD), b) a 3' splice region comprising a branch point, a polypyrimidine tract and a 3' splice acceptor site, c) a spacer sequence that separates the 3' splice region from the target binding domain AS, d) a nucleotide sequence to be trans-spliced to the target pre-mRNA wherein said nucleotide sequence encodes at least a part of the DMD polypeptide.

This nucleic acid molecule is hereafter referred to as "simple trans-splicing molecule", or "simple PTM" of the invention.

The present invention is also drawn to a recombinant vector comprising the PTMs of the invention and to a cell comprising the PTMs of the invention, or the recombinant vector of comprising the PTMs of the invention.

The compositions and methods can be used to provide a gene encoding a functional biologically active molecule to cells of an individual with an inherited genetic disorder where expression of the missing or mutant gene product produces a normal phenotype.

Specifically, the compositions and methods can be used to replace in vitro a mutated endogenous exon 23 or exon 70 of the DMD gene within a cell, comprising contacting the cellular pre-mRNA of the DMD gene with the PTMs of the present invention, under conditions in which the nucleotide sequence to be trans-spliced is trans-spliced to the target pre-mRNA of the DMD gene to form a chimeric mRNA within the cell.

To go further, the present invention also discloses a method for in vivo correcting a DMD genetic defect in a subject, comprising administering to said subject the PTMs of the invention, or the vector comprising the PTMs of the invention, or the cell comprising the PTMs of the invention.

More specifically, the present invention discloses a method for correcting at least one genetic mutation present in exon 23 or 70 of the DMD gene in a subject in need thereof, comprising administering to said subject the PTMs of the invention, wherein the nucleotide sequence to be trans-spliced is at least the exon 23 or at least the exon 70 of the DMD gene.

The present invention also provides pharmaceutical compositions comprising an effective amount of the PTMs of the invention and a pharmaceutically acceptable carrier.

In a first aspect, the present invention relies on the designing and the optimization of a double PTM dedicated to concomitant 3' and 5' trans-splicing reactions in order to replace specific nucleotide sequence, and for example a mutated exon, or to replace missing exons in the case of deletion mutations. Such a double PTM therefore necessarily contains a 3' splice region and a 5' splice region. Also, the double PTM must contain at least two distinct target binding domains that enable the PTM to recognize and get very close to the target mRNA. In the context of the invention, these two target binding domains are called "AS" (for Anti Sens).

In this first aspect, the present invention is thus drawn to a nucleic acid molecule comprising:

a) two target binding domains AS and AS' that target the binding of the nucleic acid molecule to a target pre-mRNA, wherein the two target binding domains AS and AS' are located respectively at the 5'-end and at the 3'-end of the nucleic acid molecule, b) a 3' splice region comprising a branch point, a polypyrimidine tract and a 3' splice acceptor site, c) a 5' splice region comprising a 5' splice donor site, d) a spacer sequence that separates the 3' splice region from the 5'-end target binding domain AS, e) a spacer sequence that separates the 5' splice region from the 3'-end target binding domain AS', and f) a nucleotide sequence to be trans-spliced to the target pre-mRNA, wherein said nucleotide sequence encodes at least a part of a normal polypeptide, and is located between the 3' splice region and the 5' splice region of said nucleic acid.

This nucleic acid molecule is hereafter designated by the "double trans-splicing molecule of the invention" or "the double PTM of the invention".

The target binding domain of a PTM endows the PTM with a binding affinity for the target pre-mRNA. As used herein, a target binding domain is defined as any molecule, i.e., nucleotide, protein, chemical compound, etc., that confers specificity of binding and anchors the pre-mRNA closely in space to the PTM so that the spliceosome processing machinery of the nucleus can trans-splice a portion of the PTM to a portion of the pre-mRNA. The target binding domains of the PTM are preferably nucleotide sequences which are complementary to and in anti-sense orientation to the targeted region of the selected target pre-mRNA. The target binding domains may comprise up to several thousand nucleotides. In preferred embodiments of the invention the target binding domains may comprise between about 100 and 200 nucleotides, and preferably about 150 nucleotides.

A sequence "complementary" to a portion of an RNA, as referred to herein, means a sequence having sufficient complementarity to be able to hybridize with the target pre-mRNA, forming a stable duplex. The ability to hybridize will depend on both the degree of complementarity and the length of the nucleic acid (See, for example, Sambrook et al., 1989, Molecular Cloning, A Laboratory Manual, 2d Ed., Cold Spring Harbor Laboratory Press, Cold Spring Harbor, N.Y.). Generally, the longer the hybridizing nucleic acid, the more base mismatches with an RNA it may contain and still form a stable duplex. One skilled in the art can ascertain a tolerable degree of mismatch or length of duplex by use of standard procedures to determine the stability of the hybridized complex. Binding domains may encompass any or all sequences located within the target intron and flanking exons and may consist of contiguous sequence or contain sequence gaps ranging in size from a few to several hundred nucleotides in length. In such cases, the binding domain may be considered to be comprised of multiple, smaller binding domains that are positioned within the PTM in either orientation (sense or antisense) relative to the target sequence or to each other. Any or all sequence elements within the binding domain may contain significant complementarity to the target region.

After having tested various combinations of antisens nucleotide sequences, the present inventors have found that, contrary to what was commonly taught in the art, it is no use to block the endogenous splicing signals on the nascent pre-mRNA transcript via base-pairing. Therefore, in a preferred embodiment, the target binding domains of the double PTM of the present invention are not blocking the endogenous splicing signals on the nascent pre-RNA transcript.

In a first embodiment, the target pre-RNA is a mutated exon of a gene, and the nucleotide sequence to be trans-spliced to the target pre-mRNA, is the corresponding normal exon, or exons, of said gene.

The gene targeted by double-trans-splicing must be a gene that is actively transcribed in the cell targeted by the procedure. It must be composed of several exons that are transcribed into a pre-mRNA molecule.

In this case, it has been shown here for the first time that bringing the replacing exon closer to endogenous splice site to be joined does not produce the best results. Therefore, in the context of the invention, the target binding domains AS and AS' are preferably not complementary to sequences that are close to the endogenous splice sites of the mutated exon to be replaced, that is, below 200 nucleotides from the endogenous splice sites.

The double PTM molecule also contains a 3' splice region that includes a branch point sequence, a polypyrimidine tract (such as SEQ ID NO 28) and a 3' splice acceptor site. The double PTM molecule also contains a 5' splice region.

Consensus sequences for the 5' splice donor site and the 3' splice region used in RNA splicing are well known in the art (See, Moore, et al., 1993, The RNA World, Cold Spring Harbor Laboratory Press, p. 303-358). In addition, modified consensus sequences that maintain the ability to function as 5' donor splice sites and 3' splice regions may be used in the practice of the invention. Briefly, the mammalian consensus sequences for the 5' donor splice site and the 3' acceptor splice site are respectively: GTAAGT and TCCCTCCAG. For example, the 5' donor splice site of the double PTM of the invention can be GTAAGA (SEQ ID NO: 30) and the 3' acceptor splice site of the double PTM of the invention can be GGAAAACAG (SEQ ID NO: 29).

The branch point consensus sequence in mammals is YNYURAC (Y=pyrimidine; N=any nucleotide; R=purine). For example, the branch point can be TACTAAC (SEQ ID NO:25) corresponding to the well conserved yeast branch point (Mansfield et al 2000). The A is the site of branch formation. A polypyrimidine tract is located between the branch point and the 3' splice site acceptor and is important for different branch point utilization and 3' splice site recognition. Recently, pre-mRNA introns beginning with the dinucleotide AU and ending with the dinucleotide AC have been identified and referred to as U12 introns. U12 intron sequences as well as any sequences that function as splice acceptor/donor sequences may also be used to generate the double PTMs of the invention.

A spacer region to separate the RNA splice site from the target binding domain is also included in the double PTM. The double PTM of the invention contains at least two different spacers: a spacer sequence that separates the 3' splice region from the 5'-end target binding domain AS, and a spacer sequence that separates the 5' splice region from the 3'-end target binding domain AS'. They are preferably non coding sequences and comprise between 10 and 100 nucleotides, preferably between 20 and 70 nucleotides, more preferably between 30 and 50 nucleotides. The spacer regions may be designed to include features such as stop codons which would block any translation of a spliced PTM. In an embodiment of the invention, splicing enhancers such as, for example, sequences referred to as exonic splicing enhancers may also be included in the double PTM design. Transacting splicing factors, namely the serine/arginine-rich (SR) proteins, have been shown to interact with such exonic splicing enhancers and modulate splicing (Tacke et al., 1999). Also, the G-rich intronic splice enhancer from the human GH-1 gene (SEQ ID NO: 26) and/or the DISE sequence from the rat FGFR2 gene (SEQ ID NO: 27) can be used as splicing enhancers.

In a more preferred embodiment, the spacer sequence that separates the 3' splice region from the 5'-end target binding domain AS contains a ISE, for example the G-rich intronic splice enhancer from the human GH-1 gene (SEQ ID NO: 26), and the spacer sequence that separates the 5' splice region from the 3'-end target binding domain AS contains a DISE sequence, for example the DISE sequence from the rat FGFR2 gene (SEQ ID NO: 27), preferably in close vicinity of the nucleotide sequence to be trans-spliced, that is the DISE sequence should be located not farer than 60 nucleotides from the nucleotide sequence to be trans-spliced.

Additional features can be added to the double PTM molecule either after, or before, the nucleotide sequence encoding a translatable protein, such as polyadenylation signals to modify RNA expression/stability, or 5' splice sequences to enhance splicing, additional binding regions, "safety"-self complementary regions, additional splice sites, or protective groups to modulate the stability of the molecule and prevent degradation. In addition, stop codons may be included in the PTM structure to prevent translation of unspliced PTMs. Further elements such as a 3' hairpin structure, circularized RNA, nucleotide base modification, or synthetic analogs can be incorporated into double PTMs to promote or facilitate nuclear localization and spliceosomal incorporation, and intra-cellular stability.

As an example, the present invention relates to the design and the optimization of ExChange constructs (PTMs) designed for rescuing mutated mRNAs from very large genes such as the dystrophin gene DMD (for example the human DMD gene identified as NC_000023.10 or the mouse DMD gene identified as NC_000086.6). Mutations in the dystrophin gene DMD cause the Duchenne muscular dystrophy (DMD), the most common severe childhood muscular pathology. Recently, exon skipping strategies have proven to be efficacious in restoring functional dystrophin expression in models of muscular dystrophy including the mdx mouse, the GRMD dog and muscle stem cells from DMD patients and in four DMD patients by local intramuscular injection (Goyenvalle et al., 2004; Denti et al., 2006; Yokota et al., 2009). Indeed, the modular structure of the dystrophin, with its central rod-domain made of 24 spectrin-like repeats, tolerates large truncations. However, exon skipping strategies only concern patients for whom forced splicing would generate a shorter but still functional protein. Many pathological situations escape this prerequisite. In this context, ExChange strategies could be of great interest for replacing precisely a mutated exon of DMD by a normal corresponding exon, and for example the mutated exon 23 which carries a stop mutation in the mdx mouse model of DMD (cf. SEQ ID NO 9), or a genetic anomaly present between exons 59 and 79, which represent 8% of Duchenne patients. Furthermore, ExChange strategies could be useful for replacing missing exons, thereby producing a full length gene product instead of a truncated gene product as results from exon skipping approaches.

In such a view, the present invention shows here for the first time a PTM enabling an efficient exon exchange (for example one exon of the DMD gene, and more particularly the exon 23 of the DMD gene) importantly demonstrating that the ExChange of a specific exon is possible and efficient with the "double" trans-splicing technology.

In a preferred embodiment, the present invention is thus drawn to a nucleic acid molecule comprising:

a) two target binding domains AS and AS' that target binding of the nucleic acid molecule to the pre-mRNA of the dystrophin gene (DMD), wherein the two target binding domains AS and AS' are located respectively at the 5'-end and at the 3'-end of the nucleic acid molecule, b) a 3' splice region comprising a branch point, a polypyrimidine tract and a 3' splice acceptor site, c) a 5' splice region comprising a 5' splice donor site, d) a spacer sequence that separates the 3' splice region from the 5'-end target binding domain AS, e) a spacer sequence that separates the 5' splice region from the 3'-end target binding domain AS', and f) a nucleotide sequence to be trans-spliced to the target pre-mRNA of the dystrophin gene (DMD), wherein said nucleotide sequence encodes at least a part of the normal dystrophin polypeptide, and is located between the 3' splice region and the 5' splice region of said nucleic acid.

The general design, construction and genetic engineering of PTMs and demonstration of their ability to mediate successful trans-splicing reactions within the cell are described in detail in U.S. Pat. Nos. 6,083,702, 6,013,487 and 6,280,978 as well as patent Ser. Nos. 09/941,492, 09/756,095, 09/756,096 and 09/756,097 the disclosures of which are incorporated by reference in their entirety herein.

In a particular embodiment, in the double PTM of the present invention, the nucleotide sequence to be trans-spliced comprises at least one exon of the normal DMD gene, preferably the sequence of exon 23 of the normal DMD gene, that is SEQ ID NO 8 (from the mouse gene) or SEQ ID NO 60 (from the human gene), or the exon 70 of the normal DMD gene (SEQ ID NO 72 for the human gene, SEQ ID NO 73 for the mouse gene).

In a preferred embodiment of the invention, the 5'-end target binding domain AS targets the binding of the nucleic acid to the intron 22 of the pre-mRNA of the DMD gene (SEQ ID NO 11 for the mouse gene, or SEQ ID NO 61 for the human gene) and the 3'-end target binding domain AS' targets the binding of the nucleic acid to the intron 23 of the pre-RNA of the DMD gene (SEQ ID NO 12 for the mouse gene, SEQ ID NO 62 for the human gene).

In an embodiment of the invention, the target binding domains AS and AS' comprises between about 100 and about 200 nucleotides, preferably about 150 nucleotides.

In a preferred embodiment, the 5'-end target binding domain AS comprises at least 20 successive nucleotides of one of the nucleotide sequence chosen among: SEQ ID NO 13 (hereafter called "AS1") and SEQ ID NO 14 (hereafter called "AS2"). Preferably, the 5'-end target binding domain AS comprises at least 20 successive nucleotides of SEQ ID NO 15.

On the other hand, the 3'-end target binding domain AS' targets preferably the binding of the nucleic acid to a nucleotide sequence located in the 5'-half of the nucleotide sequence of intron 23, and, more preferably, to a nucleotide sequence located in SEQ ID NO 22 (for the mouse gene) and comprises at least 20 successive nucleotides of one of the nucleotide sequences chosen among: SEQ ID NO 16 (hereafter called "AS4"), SEQ ID NO 19 (herafter called "AS 7"), SEQ ID NO 20 (hereafter called "AS8") and SEQ ID NO 21 (hereafter called "2×AS4"). In a preferred embodiment, the 3'-end target binding domain AS' comprises at least 20 successive nucleotides of SEQ ID NO 21.

In another embodiment, the double PTM of the invention comprises a conserved yeast branch point sequence, for example the yeast branch point of SEQ ID NO 25.

In another embodiment, the spacer separating the 5' splice donor site and the 3'-end target binding domain AS' comprises between 10 and 100 nucleotides, preferably between 20 and 70 nucleotides, more preferably between 30 and 50 nucleotides. In a preferred embodiment, this spacer comprises a downstream intronic splice enhancer (DISE), which is preferably the DISE sequence from the rat FGFR2 gene, i.e. the SEQ ID NO 27.

The spacer sequence that separates the 3' splice region from the 5'-end target binding domain AS comprises between 10 and 100 nucleotides, preferably between 20 and 70 nucleotides, more preferably between 30 and 50 nucleotides.

Such spacers are preferably non coding sequences but may be designed to include features such as stop codons which would block any translation of a spliced PTM. Examples of useful spacers are given in the experimental part of this application. They are for example SEQ ID NO 23 (3' end), and SEQ ID NO 24 (5' end).

In a specific embodiment, the present invention is drawn to a recombinant vector comprising the nucleic acid previously described. More particularly, the double PTM of interest may be recombinantly engineered into a variety of host vector systems that also provide for replication of the DNA in large scale and contain the necessary elements for directing the transcription of the double PTM. The use of such a construct to transfect target cells in the patient will result in the transcription of sufficient amounts of double PTMs that will form complementary base pairs with the endogenously expressed pre-mRNA targets, such as for example, DMD pre-mRNA target, and thereby facilitate a trans-splicing reaction between the complexed nucleic acid molecules. Such a vector can remain episomal or become chromosomally integrated, as long as it can be transcribed to produce the desired RNA, i.e., PTM. Such vectors can be constructed by recombinant DNA technology methods standard in the art. Vectors comprising the double PTM of interest can be plasmid, viral, or others known in the art, used for replication and expression in mammalian cells. Expression of the double PTM can be regulated by any promoter/enhancer sequences known in the art to act in mammalian, preferably human cells. Such promoters/enhancers can be inducible or constitutive. Such promoters include but are not limited to: the SV40 early promoter region, the promoter contained in the 3' long terminal repeat of Rous sarcoma virus, the herpes thymidine kinase promoter, the regulatory sequences of the metallothionein gene, the viral CMV promoter, the human chorionic gonadotropin-P promoter, etc. Any type of plasmid, cosmid, YAC or viral vector can be used to prepare the recombinant DNA construct which can be introduced directly into the tissue site. Alternatively, viral vectors can be used which selectively infect the desired target cell. Vectors for use in the practice of the invention include any eukaryotic expression vectors, including but not limited to viral expression vectors such as those derived from the class of retroviruses, adenoviruses or adeno-associated viruses.

In a preferred embodiment, the recombinant vector of the invention is an eukaryotic expression vector.

In another specific embodiment, the present invention comprises delivering the double PTM of the invention to a target cell. Various delivery systems are known and can be used to transfer the compositions of the invention into cells, e.g. encapsulation in liposomes, microparticles, microcapsules, recombinant cells capable of expressing the composition, receptor-mediated endocytosis, construction of a nucleic acid as part of a retroviral, adenoviral, adeno-associated viral or other vector, injection of DNA, electroporation, calcium phosphate mediated transfection, etc. In this case, the PTM which may be in any form used by one skilled in the art, for example, an RNA molecule, or a DNA vector which is transcribed into a RNA molecule, wherein said PTM binds to a pre-mRNA and mediates a double trans-splicing reaction resulting in the formation of a chimeric RNA comprising a portion of the PTM molecule spliced to a portion of the pre-mRNA. The present invention also concerns a cell comprising the double PTM of the invention, or the recombinant vector of comprising the double PTM of the invention.

In a preferred embodiment, the cell comprising the double PTM or the recombinant vector comprising the double PTM is an eukaryotic cell.

The compositions and methods can be used to provide a gene encoding a functional biologically active molecule to cells of an individual with an inherited genetic disorder where expression of the missing or mutant gene product produces a normal phenotype.

Specifically, the compositions and methods can be used to replace in vitro a mutated endogenous exon of the DMD gene within a cell comprising contacting the cellular pre-mRNA of the DMD gene with the double PTM of the present invention, under conditions in which the nucleotide sequence to be trans-spliced is trans-spliced to the target pre-mRNA of the DMD gene to form a chimeric mRNA within the cell. Said mutated exon is preferably exon 23 of the DMD gene.

To go further, the present invention also discloses a method for in vivo correcting a DMD genetic defect in a subject, comprising administering to said subject the double PTM of the invention, or the vector comprising the double PTM of the invention, or the cell comprising the double PTM of the invention.

More specifically, the present invention discloses a method for correcting at least one genetic mutation present in at least one endogenous mutated exon of the DMD gene in a subject in need thereof, comprising administering to said subject the double PTM of the invention.

Preferably, said endogenous mutated exon is exon 23 of the DMD gene, or exon 70 of the DMD gene, and the nucleotide sequence to be trans-spliced comprises at least the exon 23 of the DMD gene (SEQ ID NO 8 for the mouse gene, SEQ ID NO 60 for the human gene), or at least the exon 70 of the DMD gene (SEQ ID NO 72 for the mouse gene, SEQ ID NO 73 for the human gene).

In other words, the present invention discloses a double PTM, a vector comprising it, or a cell comprising it, for their use for correcting a DMD genetic defect in a subject in need thereof, or, more precisely, for their use for correcting at least one genetic mutation present in at least one of the DMD gene in a subject in need thereof, wherein, preferably said endogenous mutated exon is exon 23 of the DMD gene or exon 70 of the DMD gene, and the nucleotide sequence to be trans-spliced comprises at least the exon 23 of the DMD gene (SEQ ID NO 8 for the mouse gene, SEQ ID NO 60 for the human gene), or at least the exon 70 of the DMD gene (SEQ ID NO 72 for the mouse gene, SEQ ID NO 73 for the human gene).

The present invention also provides pharmaceutical compositions comprising an effective amount of the double PTM of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

Eventually, the present invention is drawn to a method for treating the Duchenne muscular dystrophy in a subject in need thereof, comprising administering to said subject the pharmaceutical composition comprising the double PTM of the invention. Preferably, the nucleotide sequence to be trans-spliced comprises at least an exon of the DMD gene, for example the exon 23 of the DMD gene (SEQ ID NO 8 or SEQ ID NO 60), or the exon 70 of the DMD gene (SEQ ID NO 72 or SEQ ID NO 73). In other words, the present invention covers the double PTM of the invention for its use for treating the Duchenne muscular dystrophy in a subject in need thereof. Preferably, the nucleotide sequence to be trans-spliced is at least an exon of the DMD gene, for example the exon 23 of the DMD gene (SEQ ID NO 8 or SEQ ID NO 60) or the exon 70 of the DMD gene (SEQ ID NO 72 or SEQ ID NO 73).

In a specific embodiment, it may be desirable to administer the pharmaceutical compositions of the invention locally to the area in need of treatment, i.e. in the muscles. This may be achieved by, for example, and not by way of limitation, local infusion during surgery, loco-regional infusion under high pressure in a limb where the arterial and venous blood flux is intermittently interrupted by a tourniquet, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other controlled release drug delivery systems exist, such as nanoparticles, matrices such as controlled-release polymers, hydrogels. The double PTM will be administered in amounts which are effective to produce the desired effect in the targeted cell. Effective dosages of the double PTMs can be determined through procedures well known to those in the art which address such parameters as biological half-life, bioavailability and toxicity. The amount of the composition of the invention which will be effective will depend on the severity of the DMD being treated, and can be determined by standard clinical techniques.

The double PTM can also be delivered to cells or stem cells ex vivo which can, in a second step after ex vivo correction, be transferred as a cell transplant to an individual with the goal of correcting an organ or an individual affected by a genetic disease through cell therapy.

In a second aspect, the present invention is drawn to a nucleic acid molecule dedicated to simple trans-splicing as it is described in the following examples.

In this particular embodiment, the nucleic acid molecule of the invention comprises:

a) one target binding domain (AS) that target binding of the nucleic acid molecule to the pre-mRNA of the dystrophin gene (DMD), b) a 3' splice region comprising a branch point, a polypyrimidine tract and a 3' splice acceptor site, c) a spacer sequence that separates the 3' splice region from the target binding domain AS, d) a nucleotide sequence to be trans-spliced to the target pre-mRNA wherein said nucleotide sequence encodes at least a part of the DMD polypeptide.

This nucleic acid molecule is hereafter referred to as "simple trans-splicing molecule", or "simple PTM" of the invention.

The different parts of this simple trans-splicing molecule (3' splice acceptor site, branch point, polypyrimidine tract, spacer sequence) are the same as described above for the PTM mediating double trans-splicing, that is, for example, SEQ ID NO 29 for the 3' splice acceptor site, SEQ ID NO 25 for the branch point, SEQ ID NO 28 for the polypyrimidine tract, SEQ ID NO 23 for the 3' end spacer.

As a matter of fact, the present invention shows also here for the first time a simple PTM enabling efficient exon(s) replacement (for example replacing anormal exon 70 of the human DMD gene, by the normal one), importantly demonstrating that the replacement of specific exon(s) is possible and efficient also with a "simple" trans-splicing technology (cf. example 2).

In this simple PTM, the nucleotide sequence to be trans-spliced to the pre-mRNA of the dystrophin gene (DMD) comprises preferably one or several exon(s) of the normal DMD gene, more preferably the exon 23 or any one of the exons 59 to 79 of the DMD gene. Even more preferably, the sequence to be trans-spliced is the exon 70 of the DMD gene, or the cDNA from all the exons 59 to 79 of the DMD gene, as shown in example 2 below.

More precisely, in the simple PTM of the present invention, the nucleotide sequence to be trans-spliced is either the sequence of exon 23 of the normal DMD gene (that is SEQ ID NO 8 for the mouse gene or SEQ ID NO 60 for the human gene), or the sequence of exon 70 of the DMD gene (that is, SEQ ID NO 72 for the human gene, and SEQ ID NO 73 for the mouse gene), or the cDNA corresponding to exons 59 to 79 of the DMD gene (that is SEQ ID NO 69 for the mouse gene or SEQ ID NO 70 for the human gene).

In a preferred embodiment of the invention, the 5' end target binding domain AS of the simple PTM of the invention targets the binding of the nucleic acid to intron 22 of the pre-mRNA of the DMD gene (SEQ ID NO 11 for the mouse gene, or SEQ ID NO 61 for the human gene), or to intron 58 of the pre-mRNA of the DMD gene (SEQ ID NO: 66 for the mouse gene, SEQ ID NO 67 for the human gene).

In a more preferred embodiment, the 5' end target binding domain AS of the simple PTM of the invention has the sequence SEQ ID NO 68 (for targeting the PTM to intron 58 of the DMD gene) or SEQ ID NO 13, SEQ ID NO 14, SEQ ID NO 15, or SEQ ID NO 58 (for targeting the PTM to intron 22 of the DMD gene).

In an even more preferred embodiment, the simple trans-splicing molecule of the invention has the SEQ ID NO 71.

In a specific embodiment, the present invention is drawn to a recombinant vector comprising the simple PTM previously described. More particularly, the simple PTM of interest may be recombinantly engineered into a variety of host vector systems that also provide for replication of the DNA in large scale and contain the necessary elements for directing the transcription of the simple PTM. The use of such a construct to transfect target cells in the patient will result in the transcription of sufficient amounts of simple PTMs that will form complementary base pairs with the endogenously expressed pre-mRNA targets, such as for example, DMD pre-mRNA target, and thereby facilitate a trans-splicing reaction between the complexed nucleic acid molecules. Such a vector can remain episomal or become chromosomally integrated, as long as it can be transcribed to produce the desired RNA, i.e., PTM. Such vectors can be constructed by recombinant DNA technology methods standard in the art. Vectors comprising the simple PTM of interest can be plasmid, viral, or others known in the art, used for replication and expression in mammalian cells. Expression of the simple PTM can be regulated by any promoter/enhancer sequences known in the art to act in mammalian, preferably human cells. Such promoters/enhancers can be inducible or constitutive. Such promoters include but are not limited to: the SV40 early promoter region, the promoter contained in the 3' long terminal repeat of Rous sarcoma virus, the herpes thymidine kinase promoter, the regulatory sequences of the metallothionein gene, the viral CMV promoter, the human chorionic gonadotropin-P promoter, etc. Any type of plasmid, cosmid, YAC or viral vector can be used to prepare the recombinant DNA construct which can be introduced directly into the tissue site. Alternatively, viral vectors can be used which selectively infect the desired target cell. Vectors for use in the practice of the invention include any eukaryotic expression vectors, including but not limited to viral expression vectors such as those derived from the class of retroviruses, adenoviruses or adeno-associated viruses.

In a preferred embodiment, the recombinant vector of the invention is an eukaryotic expression vector.

In another specific embodiment, the present invention comprises delivering the simple PTM of the invention to a target cell. Various delivery systems are known and can be used to transfer the compositions of the invention into cells, e.g. encapsulation in liposomes, microparticles, microcapsules, recombinant cells capable of expressing the composition, receptor-mediated endocytosis, construction of a nucleic acid as part of a retroviral, adenoviral, adeno-associated viral or other vector, injection of DNA, electroporation, calcium phosphate mediated transfection, etc. In this case, the simple PTM which may be in any form used by one skilled in the art, for example, an RNA molecule, or a DNA vector which is transcribed into a RNA molecule, wherein said simple PTM binds to a pre-mRNA and mediates a simple trans-splicing reaction resulting in the formation of a chimeric RNA comprising a portion of the simple PTM molecule spliced to a portion of the pre-mRNA. The present invention also concerns a cell comprising the simple PTM of the invention, or the recombinant vector of comprising the simple PTM of the invention.

In a preferred embodiment, the cell comprising the simple PTM or the recombinant vector comprising the simple PTM is an eukaryotic cell.

The simple PTM of the invention appears to be a very interesting tool to target DMD patients independently of their DMD mutation. By enabling to restore mutated exons of the DMD gene, this molecule appears to be also an efficient tool to treat DMD patients.

Therefore, the present invention is also drawn to a method for treating a patient suffering from the Duchenne muscular dystrophy comprising administering to said patient a pharmaceutical composition comprising the simple trans-splicing molecule of the invention or the recombinant vector comprising it, or the cell comprising them. In other words, the present invention is drawn to the simple trans-splicing molecule of the invention, or the recombinant vector comprising it, or the cell comprising them for their use in a pharmaceutical composition for treating the Duchenne muscular dystrophy in a subject in need thereof.

More precisely, the present invention also concerns a method for correcting a DMD genetic defect in a subject, comprising administering to said subject the simple trans-splicing molecule of the invention, or the recombinant vector comprising it, or the cell comprising them. In other words, the invention is drawn to the simple trans-splicing molecule of the invention, or the recombinant vector comprising it, or the cell comprising them, for their use for correcting a DMD genetic defect in a subject in need thereof.

Preferably, the nucleotide sequence to be trans-spliced comprises at least one exon of the DMD gene, and comprises more preferably at least exon 23 of the normal DMD gene (that is SEQ ID NO 8 for the mouse gene or SEQ ID NO 60 for the human gene), or exon 70 of the DMD gene (that is, SEQ ID NO 72 for the human gene, or SEQ ID NO 73 for the murine gene) or any exon chosen among exons 59 to 79 of the DMD gene. In a preferred embodiment, it comprises the cDNA from exon 59 to 79 of DMD gene (that is, SEQ ID NO 70 for the human gene, and SEQ ID NO 69 for the mouse gene).

The present invention also concerns an in vitro method of replacing at least one mutated endogenous exon of the DMD gene within a cell, comprising contacting the cellular pre-mRNA of the DMD gene with the simple trans-splicing molecule of the invention, under conditions in which the nucleotide sequence to be trans-spliced is trans-spliced to the target pre-mRNA of the DMD gene to form a chimeric mRNA within the cell. Preferably, said mutated exon is exon 23 of the DMD gene, or exon 70 of the DMD gene or any exon chosen among exons 59 to 79 of the DMD gene. More preferably, the nucleotide sequence to be trans-spliced to the target pre-mRNA of the DMD gene thus comprises at least exon 23, or exon 70 of the DMD gene, or any exon chosen among exons 59 to 79 of the DMD gene. Even more preferably the nucleotide sequence to be trans-spliced to the target pre-mRNA of the DMD gene comprises the cDNA from exon 59 to 79 of DMD human gene.

The present invention also concerns a method for correcting at least one genetic mutation present in at least one exon of the DMD gene in a subject in need thereof, comprising administering to said subject the simple trans-splicing molecule of the invention. Preferably, said at least one exon of the DMD gene is exon 23 or exon 70, and the nucleotide sequence to be trans-spliced comprises at least the exon 23 of the DMD gene (that is SEQ ID NO 8 for the mouse gene or SEQ ID NO 60 for the human gene), or the exon 70 of the DMD gene (that is, SEQ ID NO 72 for the human gene, or SEQ ID NO 73 for the murine gene), or the cDNA from exon 59 to exon 79 of the normal DMD human gene (SEQ ID NO 70).

In this case, in other words, the invention is drawn to the simple trans-splicing molecule of the invention, or the recombinant vector comprising it, or the cell comprising them, for their use for correcting at least one genetic mutation present in exon 23 or exon 70 of the normal human DMD gene in a subject in need thereof, wherein the nucleotide sequence to be trans-spliced comprises at least the exon 23 of the normal DMD gene (that is SEQ ID NO 8 for the mouse gene or SEQ ID NO 60 for the human gene), or the exon 70 of the normal DMD gene (that is, SEQ ID NO 72 for the human gene, or SEQ ID NO 73 for the mouse gene), or the cDNA from exon 59 to exon 79 of the normal DMD human gene (SEQ ID NO 70).

The present invention also provides pharmaceutical compositions comprising an effective amount of the simple PTM of the invention, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Examples of suitable pharmaceutical carriers are described in "Remington's Pharmaceutical sciences" by E. W. Martin.

In a specific embodiment, it may be desirable to administer the pharmaceutical compositions of the invention locally to the area in need of treatment, i.e. in the muscles. This may be achieved by, for example, and not by way of limitation, local infusion during surgery, loco-regional infusion under high pressure in a limb where the arterial and venous blood flux is intermittently interrupted by a tourniquet, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Other controlled release drug delivery systems exist, such as nanoparticles, matrices such as controlled-release polymers, hydrogels. The simple PTM will be administered in amounts which are effective to produce the desired effect in the targeted cell. Effective dosages of the simple PTMs can be determined through procedures well known to those in the art which address such parameters as biological half-life, bioavailability and toxicity. The amount of the composition of the invention which will be effective will depend on the severity of the DMD being treated, and can be determined by standard clinical techniques.

The simple PTM can also be delivered to cells or stem cells ex vivo which can, in a second step after ex vivo correction, be transferred as a cell transplant to an individual with the goal of correcting an organ or an individual affected by a genetic disease through cell therapy.

EXAMPLES

1. Double Trans-Splicing Molecule of the Invention

1.1. Materials and Methods

Plasmids Constructions

The murine DMD minigene target (3993 bp (SEQ ID NO 39)) comprising exons E22, E23, and E24 and the natural E23 flanking intronic sequences was constructed by PCR amplification from mdx genomic DNA and subcloned in pSMD2 into KpnI site. An ATG in Kozack ACCACCATGG context and a STOP codon were introduced at both sides of the minigene.

The E24 for the TS and EX molecules (114 bp (SEQ ID NO 10)) was amplified from the DMD minigene. The different domains of the TS and EX molecules detailed in Results section were constructed by PCR and subcloned in pSMD2 into HindIII and EcoRI between the CMV promoter and the polyA signal. Antisens sequences AS bind to DMD intron 22: AS1 targets nucleotides −763 to −614 (SEQ ID NO 13); AS2, −463 to −314 (SEQ ID NO 14); AS3 −159 to −10 (SEQ ID NO 15); AS3bis −159 to +5 (SEQ ID NO 58) (where nucleotide +1 is the first E23 nucleotide). The second antisens domains AS' bind to DMD intron 23: AS4, +1801 to +1950 (SEQ ID NO 16); AS5, +2101 to +2250 (SEQ ID NO 17); AS6, +2401 to +2550 (SEQ ID NO 18); AS7, −5 to +145 (SEQ ID NO 19); AS8, +151 to +300 (SEQ ID NO 20) (where nucleotide +1 is the first nucleotide of intron 23).

All expression cassettes are under the control of the strong CMV promoter and a polyA signal and were verified by sequencing.

Cell Culture and Transfection

Mouse embryonic fibroblast NIH3T3 cells were maintained in DMEM (Invitrogen) supplemented with 10% heat-inactivated FBS (Invitrogen), 100 units/ml penicillin, and 100 μg/ml streptomycin. For transfections, cells were grown to 70% confluence in 12-well plates and exposed to the DNA/Lipofectamine 2000 reagent (Invitrogen) complex for 5 h in DMEM before being returned to normal culture medium. Typically, 0.5 μg of DMD minigene and 1.5 μg of TS or EX molecules DNA were used in each transfection. Cells were routinely analyzed 72 h after transfection.

RT-PCR Analysis

Total RNA was isolated from transfected cells by using RNAeasy extraction kit (Qiagen). Reverse transcription was performed on 200 ng of RNA by using the Superscript II (Invitrogen) and the reverse primer pSMD2-R1 (see below) at 10 min at 25° C., 50 min at 42° C., and a final step of 5 min at 95° C. To detect non-repaired and repaired DMD transcripts, reverse transcribed RNA was amplified by PCR under the following conditions: 95° C. for 5 min, 30 cycles of 30 s at 95° C., 1 min at 56° C., 45 s to 1 min at 72° C., and a final step of 7 min at 72° C.

The sequences of the primers were as followed: E22-F GACACTTTACCACCAATGCGC (SEQ ID NO 36) (Primer A on FIGS. 1A-B and 2A-B), pSMD2-R1 CTTTCTGATAGGCAGCCTGC (SEQ ID NO 37) (Primer B on FIG. 1A-B) and pSMD2-R5 CTCACCCTGAAGTTCTCAGG (SEQ ID NO 38) (Primer C on FIG. 2A-B). RT-PCR products were separated by electrophoresis in 2% agarose gels with ethidium bromide and sequenced.

Quantitative Real-Time RT-PCR mRNA levels were measured by absolute quantitative real-time RT-PCR method using Absolute SYBR Green Rox Mix (Thermo scientific). Two positive control DMD cDNA fragments, E22-E23-E24 and E22-E24-E24, were cloned into the pCR®2.1-TOPO®. As a reference samples, those plasmids were 10-fold serially diluted (from $10^7$ to $10^3$ copies) and used to generate standard curves. Real-time PCR was performed and analyzed on a DNA Engine Opticon 2 (Bio-Rad). In each experiment, duplicates of standard dilution series of control plasmids and first strand cDNA generated by the Superscript II (Invitrogen) from 200 ng of total RNA were amplified by specific primers. Primers for E23, E23-F AGATGGCCAAGAAAGCACC (SEQ ID NO: 32) and E23-R CTTTCCACCAACTGGGAGG, (SEQ ID NO: 33) were used to measure non-repaired DMD transcript; and primers for E24-E24 junction, E24-F TGAAAAAACAGCTCAAACAATGC (SEQ ID NO: 34) and E24-R AGCATCCCCCAGGGCAGGC (SEQ ID NO: 35), for the repaired transcript.

1.2. Results

Design of Trans-Splicing Molecules (TS Molecules)

In ExChange molecules, the replacing exon is flanked by artificial intronic sequences with strong acceptor and donor splice sites, which are connected to antisense sequences designed to anneal the target mRNA. Annealing is crucial to permit the trans-splicing reaction, although it is not enough. Ideally, the site of annealing must disturb the definition of the targeted exon in the parental pre-messenger while enhancing cross-splicing in between the two independent mRNAs. In the case of ExChange, there are more constraints since two trans-splicing reactions must be synchronized at both edges of the targeted exon.

The murine model for DMD, the mdx mouse, carries a nonsense mutation in exon 23 (E23$^{m}$: SEQ ID NO 9) of the dystrophin gene. In order to locate the best site of annealing in intron 22, upstream the mutated exon, three trans-splicing (TS) molecules for 3' replacement only differing in their binding domains were designed (FIG. 1A). Antisense sequences of about 150 nucleotides (AS1=SEQ ID NO 13, AS2=SEQ ID NO 14 and AS3=SEQ ID NO 15) were chosen to match either to the 5' end, the middle or the 3' end of intron 22 (SEQ ID NO 11). The idea was to test whether getting the TS molecule close to its target, 5' donor splice site of intron 22, or at the opposite, masking the 3' acceptor splice site, would facilitate trans-splicing. In the three constructions, the artificial intron included a spacer sequence (SEQ ID NO 59), a strong conserved yeast branch point sequence (SEQ ID NO 25), a polypyrimidine tract (SEQ ID NO 28), and a canonical 3' acceptor splice site (SEQ ID NO 29). To facilitate the readout, it was also decided to employ exon 24 (E24 (SEQ ID NO 10)) in the TS molecule instead of the normal version of exon 23 (E23). Indeed, E24 is smaller than E23 (114 versus 213 bp) allowing unequivocal distinction by RT-PCR of repaired mRNA (E22-E24-E24) from non-repaired parental transcripts (E22-E23$^{m}$-E24). Three TS molecules for 3' replacement were thus constructed: AS1-E24 (SEQ ID NO 40), AS2-E24 (SEQ ID NO 41), AS3-E24 (SEQ ID NO 42).

As control, a trans-splicing molecule with no binding domain (AS-, SEQ ID NO 43) was used.

To facilitate the analysis of DMD splicing in tissue culture, a DMD reporter gene made of a genomic fragment of 3993 bp comprising E22 to E24 with full-length natural introns was made (SEQ ID NO 39). Cis- and trans-splicing patterns are illustrated in FIG. 1B. An RT-PCR strategy was designed to detect specifically RNA resulting from cis- and trans-splicing events by using a forward primer E22-F (SEQ ID NO 36) (arrow A in FIG. 1B) specific for E22, and a reverse primer pSMD2-R1 (SEQ ID NO 37) (arrow B) specific for a sequence upstream the polyA signal in DMD minigene and TS molecules. Importantly, these primers also allowed discriminating E22-E24 amplicons resulting from either trans-splicing or exon skipping.

3' Replacement in DMD Transcripts

DMD reporter minigene and TS plasmids were cotransfected in the mouse embryonic fibroblast NIH3T3 cell-line. Cells were harvested 72 h after transfection, and total RNA was isolated. Cis- and trans-spliced RNA patterns were assessed by RT-PCR. As expected, samples that received only the DMD minigene displayed a single 638 bp amplicon corresponding to the cis-spliced DMD transcript E22-E23$^{m}$-E24 (Ctrl in FIG. 1C). Also, cDNAs from cells transfected with both DMD minigene and trans-splicing constructs (AS2-E24) gave no PCR products when reverse transcription was omitted (RT-AS2), ensuring about the specificity of the present assay. In the presence of U7-SD23-BP22 (U7) plasmids described to induce E23 skipping (Goyenvalle et al., 2004), a 425 bp band corresponding to E22-E24 transcript from cis-splicing was detected.

In samples that received DMD minigene and TS plasmids, a product of 310 bp was generated, corresponding specifically to the trans-spliced E22-E24 variant, and not to an exon skipping product as it was obtained with U7. In the presence of either AS1-E24 (SEQ ID NO 40) or AS2-E24 (SEQ ID NO 41), the E22-E23$^{m}$-E24 amplicon corresponding to the parental DMD minigene had almost entirely disappeared thus confirming that, here, trans-splicing efficacies were nearly complete. Importantly, trans-splicing did not occur when AS was removed (AS-) from TS constructs demonstrating that this reaction required close interaction in between the two strands of mRNA to combine. The AS3-E24 TS molecule (SEQ ID NO: 42) appeared to be less efficient. Surprisingly, extending AS3 in order to cover the 3' acceptor site of E23$^{m}$ did not improve the trans-splicing reaction (not shown). These experiments show that trans-splicing could not do without AS sequences, although getting closer the two mRNAs is not sufficient.

mRNA Repair by Using ExChange

To test the possibility of mRNA repair by ExChange, several ExChange (EX) molecules AS-E24-AS' based on the efficient TS molecules mentioned above were developed, and modified to bind both intron 22 and intron 23 of the DMD reporter minigene (FIG. 2A). The EX molecules contained the same elements as previously described in AS1-E24 and AS2-E24 TS molecules followed by a 5' donor splice site (SEQ ID NO 30) and a second 150 nt antisense targeting intron 23 (SEQ ID NO 12). Five antisenses, AS 4 (SEQ ID NO 16), AS5 (SEQ ID NO 17), AS6 (SEQ ID NO 18), AS7 (SEQ ID NO 19) and AS8 (SEQ ID NO 20), were selected within intron 23 (SEQ ID NO 12), which spans over 2607 bp. The following spacer sequences were used: for the spacer sequence that separates the 3' splice region from the 5'-end target binding domain AS, spacer 2 (SEQ ID NO 24, 42 nucleotides) was used, and for the spacer sequence that separates the 5' splice region from the 3'-end target binding domain AS', spacer 1 (SEQ ID NO 23, 34 nucleotides) was used.

Finally, the following PTM were constructed: AS1-E24-AS4 (SEQ ID NO 44), AS1-E24-AS5 (SEQ ID NO 45), AS1-E24-AS6 (SEQ ID NO 46), AS1-E24-AS7 (SEQ ID NO 47), AS2-E24-AS4 (SEQ ID NO 48), AS2-E24-AS5 (SEQ ID NO 49), AS2-E24-AS6 (SEQ ID NO 50), AS2-E24-AS7 (SEQ ID NO 51), AS2-E24-AS8 (SEQ ID NO 52) and AS2-E24-2×AS4 (SEQ ID NO 53).

As previously, EX constructs and DMD minigene were cotransfected in NIH3T3 cell-line. Cells were harvested 72 h after transfection, and total RNA was extracted. To detect specifically RNA resulting from cis-splicing and/or exon exchange events, a forward primer E22-F (SEQ ID NO 36) (arrow A in FIG. 2A-B) specific of E22, and a reverse primer pSMD2-R5 (SEQ ID NO 38) (arrow C) specific of a sequence only present in the DMD minigene upstream its polyA signal were used. Targeting of AS-E24-AS' in the DMD reporter pre-mRNA is illustrated in FIG. 2A and expected sizes of the various amplification products shown in FIG. 2B.

A RT-PCR product of 408 bp was detected in samples transfected with AS2-E24-AS' plasmids (FIG. 2C). Direct sequencing confirmed that this product corresponded to the exchanged mRNA variant E22-E24-E24 (FIG. 2D). This product was absent when one of the two antisens was lacking, showing that co-targeting of intron 22 and intron 23 is crucial for ExChange. Among the antisense combinations we tried, levels of the 408 bp band were stronger with AS2-E24-2×AS4 (SEQ ID NO 53), -AS7 (SEQ ID NO 51) and -AS8 (SEQ ID NO 52). Interestingly, the AS2-E24-2×AS4 molecule (SEQ ID NO 53), which carried two AS4, was more efficient than its single AS4 counterpart. In AS2-E24-AS7 sample, a supplementary band of 294 bp was detected corresponding to E22-E24 transcript generated by exon 23 skipping. This was not surprising considering that AS7 bound the 5' donor splice site of intron 23 and would mask its recognition by the spliceosome. It is likely that AS4, AS7 and AS8 brought back EX molecules closer to E23 than AS5 and AS6 suggesting that a tight framing is essential for efficient ExChange.

Optimization of ExChange Efficacy by Adding Up Intronic Splice Enhancers

In order to improve the ExChange reaction, the G-rich intronic splice enhancer (ISE, SEQ ID NO 26) from the human GH-1 gene was added upstream the 3' acceptor site of AS2-E24-AS4 and AS2-E24-AS8 (McCarthy & Phillips, 1998) and the DISE sequence from the rat FGFR2 gene downstream the 5' donor site (SEQ ID NO 27) (Kierlin-Duncan & Sullenger, 2007) (FIG. 3A). As shown in FIG. 3B, RT-PCR analysis revealed that insertion of the DISE sequence in AS2-E24-AS4 (SEQ ID NO 54) and AS2-E24-AS8 (SEQ ID NO 55) molecules increased significantly the 408 bp band corresponding to the E22-E24-E24 mRNA variant, while addition of ISE sequence did not enhance the ExChange efficacy. As expected, no ExChange was observed with control vectors lacking the downstream AS': AS2-ISE-E24 and AS2-E24-DISE. FIG. 3C shows ExChange efficacy of various vectors by using quantitative RT-PCR. The AS2-DISE-E24-AS4 (SEQ ID NO 54) molecule allowed obtaining 53% of exon exchange. Its efficacy was improved by about 7.5 folds when compared to its counterpart AS2-E24-AS4 (SEQ ID NO 48) lacking the DISE motive.

Interestingly, introduction of two redundant downstream AS' (here AS4) improved ExChange efficacy, which was about 30%. However, AS2-E24-DISE-2×AS4 (SEQ ID NO 57) was not more efficient than AS2-DISE-E24-AS4 (SEQ ID NO 54)(data not shown).

2. Simple Trans-Splicing Molecule of the Invention 2.1. Materials and Methods

Plasmid Constructions

The different domains of the TSM molecules were constructed by PCR and subcloned into pSMD2. Human dystrophin exons 59 to 79 until the STOP codon (2390 bp, see SEQ ID NO 70) were amplified from human myotubes cDNA while antisense sequences from human genomic DNA. Antisense sequence binds to dystrophin intron 58: nucleotides −445 to −295 (where nucleotide +1 is the first E59 nucleotide, SEQ ID NO 68). The trans-splicing cassettes were subcloned into a plasmid pRRL-cPPT-mcs-WPRE under hPGK promoter (Zufferey R et al, 1997). All the constructs were verified by sequencing.

Sequences

Artificial intron included a spacer sequence, a strong conserved yeast branch point sequence (BP), a polypyrimidine tract (PPT) and a canonical 3' splice acceptor site (SA): the same sequences are already described for the double PTM of example 1.

Cell Cultures

Primary DMD myoblast cell cultures were established from explants of biceps as described previously (Mouly V et al, 1993), in accordance with French ethics legislation. DMD and control myoblasts CHQ (Edom et al, 1994) were grown in Skeletal Muscle Cell Growth Medium (PromoCell). To induce differentiation, cultures were switched to DMEM 2% horse serum with apotransferrin (100 μg/ml) and insulin (10 μg/ml). All cultures were grown in humidified incubators at 37° C. in 5% CO2.

Lentiviral Productions

Lentiviral vectors pseudotyped with the VSV-G protein were produced by transient quadri-transfection into 293T cells were determined by transduction of HCT116 cells and assayed by quantitative real-time PCR on genomic DNA [Charrier S et al, 2005). Titration of the lentivirus is expressed as viral genome/mL (vg/mL) (ranging from $2.5\times10^9$ to $5\times10^9$ vg/mL). $5\times10^6$ vg were used to transduce $4\times10^5$ myoblasts plated the day before in 24 wells tissue culture dishes in 500 μL of DMEM supplemented with 10% FCS. Four hours post-transduction, the medium was diluted by adding 200 μL per well of previous medium. The dishes were incubated for 24 hr at 37° C. and 5% CO2 before washing.

RT-PCR Analysis

Total RNA was extracted from transduced myotubes with TRIzol reagent (Invitrogen). Five microgram of RNA was reverse transcribed using SuperScript III First-Strand Synthesis SuperMix (Invitrogen) and the reverse primer Pst1-WPRE-Ro, AACTGCAGCAGGCGGGGAGGCGGCCCAAAG (Ro on FIG. 2A). cDNAs were subjected to nested PCR amplification with Phusion High-Fidelity PCR Master Mix with GC buffer (Finnzymes) under the following conditions: 95° C. for 5 min, 20 cycles of 30 s at 95° C., 2 min at 56° C., 45 s to 1 min at 72° C., and a final step of 7 min at 72° C., using external primers E58-Fo CATGAGTACTCTTGAGACTG (Fo on FIG. 2A) and WPRE-Ro AGCAGCGTATCCACATAGCG (Ro). Five microliters of each of these reactions was then reamplified for 30 cycles using the internal primers E58-Fi, AGGACTAGAGAAACTCTACC (Fi), and WPRE-Ri, TTGTCGACCAGCGTTTCTAG (Ri). RT-PCR products were separated by electrophoresis in 1% agarose gels with ethidium bromide and sequenced.

Protein Analysis

Forty μg of protein were loaded onto NuPAGE® Novex 4-12% Bis-Tris Gel (Invitrogen), electrophoresed, blotted onto nitrocellulose membranes and probed with 1:50 NCL-DYS1 or NCL-DYS2 (NovoCastra), followed by incubation with 1:15000 horseradish peroxidase-conjugated secondary antibody (Jackson ImmunoResearch) and SuperSignal® West Pico Analysis System (Thermo Scientific).

2.2. Results

The aim of this work was to repair by simple trans-splicing dystrophin pre-mRNAs carrying any genetic anomalies present between exons 59 to 79, which represents 8% of Duchenne patients. These patients are not treatable by exon skipping therapy as these exons are indispensable for the protein function.

The simple trans-splicing molecule contains a 150 nucleotides antisense sequence complementary to intron 58 (SEQ ID NO 68), an artificial intron included a spacer sequence (SEQ ID NO 23), a strong conserved yeast branch point sequence (BP) (SEQ ID NO 25), a polypyrimidine tract (PPT) (SEQ ID NO 28) and a canonical 3' splice acceptor site (SA) (SEQ ID NO 29), and the normal human dystrophin cDNA from exon 59 to the exon 79 STOP codon (SEQ ID NO 70) (cf. FIG. 4). A RT-PCR strategy was designed to amplify specifically a 2443 bp product from mRNA resulting from trans-splicing events by using forward primers, E58-Fo and E58-Fi (arrows Fo/Fi in FIG. 5A), specific for E58, and reverse primers, WPRE-Ro and WPRE-Ri (Ro/Ri in FIG. 5A), specific for the WPRE element present on trans-splicing molecules.

Duchenne muscular dystrophy patient myoblasts carrying a non-sense mutation in exon 70 were transduced with lentivirus expressing trans-splicing molecules. After differentiation, myotubes were harvested, total RNA isolated and trans-spliced dystrophin transcripts investigated by specific RT-PCR. As expected, samples that did not receive lentivirus gave no PCR products (lane "−" in FIG. 5B). In samples that express trans-splicing molecules (TsM), a product of 2443 bp was generated corresponding specifically to the trans-spliced DMD variant as confirmed by direct sequencing of the amplicon (data not shown).

In order to detect specifically rescued dystrophin encoded by trans-spliced transcripts, Western blotting with the NCL-DYS1 monoclonal antibody that recognizes spectrin-like repeats R8 to R10 was used. Consistent with the generation of trans-spliced transcripts, the full-length 427 kD dystrophin protein was readily detected by Western blot on transduced myotubes extracts (the two lanes TsM in FIG. 6), whereas no band is present in the non treated DMD cells ("−").

BIBLIOGRAPHIC REFERENCES

Chao et al., 2003 *Nat Med* 9:1015-1019
Charrier S, et al. 2005. *Gene Ther* 12: 597-606.
Chiara & Reed 1995, *Nature* 375: 510
Coady et al., 2008 *PLoS ONE* 3:e3468
Denti et al., 2006; *Proc Natl Acad Sci USA* 103:3758-3763.
Dingwell and Laskey, 1986, *Ann. Rev. Cell Biol.* 2: 367-390
Edom F, et al, 1994. *Dev Biol* 164: 219-229.
Eul et al., 1995, *EMBO. R* 14: 3226
Finta, C. et al., 2002 *J: Biol Chem* 277: 5882-5890
Goyenvalle et al., 2004 *Science* 306:1796-1799
Kierlin-Duncan & Sullenger, 2007 *RNA* 13:1317-1327
Liu et al., 2005 *Hum Gene Ther* 16:1116-1123.
Mansfield et al, *RNA* 2003 9:1290-1297
McCarthy & Phillips, 1998 *Hum Mol Genet* 7:1491-1496.
Mouly V, et al, 1993, *Neuromuscul Disord* 3: 371-377.
Shimizu et al., 1989, *Proc. Nat'l. Acad. Sci. USA* 86: 8020
Staley and Guthrie, 1998, *Cell* 92: 315-326
Tacke et al., 1999, *Curr. Opinion. Cell Biol.* 11: 358-362
Tahara et al., 2004 *Nat Med* 10:835-841.

Takayuki Horiuchi and Toshiro Aigaki, *Biol. Cell* (2006) 98, 135-140
Vellard, M. et al. *Proc. Natl. Acad. Sci.,* 1992 89: 2511-2515
Yokota et al., 2009 *Ann Neurol* June; 65(6):667-76
Zufferey R, et al, 1997. *Nat Biotechnol* 15: 871-875.

The invention claimed is:

1. A nucleic acid molecule comprising:

a) two target binding domains AS and AS' that target the binding of the nucleic acid molecule to a target pre-mRNA, wherein said two target binding domains AS and AS' are located respectively at the 5'-end and at the 3'-end of the nucleic acid molecule, b) a 3' splice region comprising a branch point, a polypyrimidine tract and a 3' splice acceptor site, c) a 5' splice region comprising a 5' splice donor site, d) a spacer sequence that separates said 3' splice region from said 5'-end target binding domain AS, e) a spacer sequence that separates said 5' splice region from said 3'-end target binding domain AS', said spacer comprising a downstream intronic splice enhancer (DISE) and f) a nucleotide sequence to be trans-spliced to said target pre-mRNA, wherein said nucleotide sequence encodes at least a part of a polypeptide, and is located between said 3' splice region and said 5' splice region of said nucleic acid.

2. The nucleic acid molecule according to claim 1, wherein said two target binding domains AS and AS' target binding of said nucleic acid molecule to the pre-mRNA of the dystrophin (DMD) gene, and wherein the nucleotide sequence to be trans-spliced encodes at least a part of the dystrophin polypeptide.

3. The nucleic acid molecule according to claim 2, wherein said nucleotide sequence to be trans-spliced comprises at least one exon of the DMD gene.

4. The nucleic acid molecule according to claim 2, wherein said nucleotide sequence to be trans-spliced comprises at least the sequence of exon 23 of the DMD gene, or the sequence of exon 70 of the DMD gene.

5. The nucleic acid molecule according to claim 4, wherein said nucleotide sequence to be trans-spliced comprises the nucleotide sequence of exon 23 of the human DMD gene as set forth in SEQ ID NO 60.

6. The nucleic acid molecule according to claim 1, wherein each of said target binding domains AS and AS' comprises between 100 and 200 nucleotides.

7. The nucleic acid molecule according to claim 6, wherein each of said target binding domains AS and AS' comprises 150 nucleotides.

8. The nucleic acid molecule according to claim 1, wherein said 5'-end target binding domain AS targets the binding of the nucleic acid to the intron 22 of the pre-mRNA of a DMD gene.

9. The nucleic acid molecule according to claim 1, wherein said 3'-end target binding domain AS' targets the binding of the nucleic acid to the intron 23 of the pre-mRNA of a DMD gene.

10. The nucleic acid molecule according to claim 1, wherein said 5'-end target binding domain AS comprises at least 20 successive nucleotides of at least one nucleotide sequence chosen among: SEQ ID NO 13 and SEQ ID NO 14.

11. The nucleic acid molecule according to claim 1, wherein said 3'-end target binding domain AS' targets the binding of the nucleic acid to a nucleotide sequence located in said 5'-half of the nucleotide sequence of intron 23.

12. The nucleic acid molecule according to claim 11, wherein said 3'-end target binding domain AS' comprises at least 20 successive nucleotides of at least one nucleotide sequence chosen among: SEQ ID NO 16, SEQ ID NO 19, and SEQ ID NO 20.

13. The nucleic acid molecule according to claim 1, wherein said 3'-end target binding domain AS' comprises at least 20 successive nucleotides of the nucleotide sequence as set forth in SEQ ID NO 21.

14. The nucleic acid molecule according to claim 1, wherein each of the two spacers comprises from 10 to 100 nucleotides.

15. The nucleic acid molecule according to claim 14, wherein each of the two spacers comprises from 30 to 50 nucleotides.

16. The nucleic acid molecule according to claim 1, wherein said branch point is a conserved yeast branch point sequence.

17. The nucleic acid molecule according to claim 16, wherein said branch point has the nucleic acid sequence of SEQ ID NO: 25.

18. A recombinant vector comprising said nucleic acid of claim 1.

19. The vector according to claim 18, wherein said vector is an eukaryotic expression vector.

20. A cell comprising said nucleic acid molecule according to claim 1.

21. The cell according to claim 18, wherein said cell is an eukaryotic cell.

22. The nucleic acid molecule according to claim 1, wherein said spacer separating said 5' splice donor site and said 3'-end target binding domain AS' comprises the DISE sequence from the rat FGFR2 gene having the nucleic acid sequence of SEQ ID NO: 27.

* * * * *

SEQUENCE LISTING

```
<160> NUMBER OF SEQ ID NOS: 73

<210> SEQ ID NO 1
<211> LENGTH: 537
<212> TYPE: DNA
<213> ORGANISM: Artificial Sequence
<220> FEATURE:
<223> OTHER INFORMATION: Nucleotide sequence of the Pre-Trans-Splicing
      molecule protein, exon 24

<400> SEQUENCE: 1

atatatttc agatttaaaa agaataagta tacaacatgg gatttttaga atcaacaaaa     60

aaattagtct ttatatgtcc tcacatcaca gaagtttctc ttactagtat ttaatttcca    120

gacttaggct attaaaataa ctactcaata ctcgagagat ctccgcggaa cattattata    180

acgttgctcg aatactaact gatatctctt cttttttttt ttccggaaaa cagaatcaca    240

taaaaacctt acagaaatgg atggctgaag ttgatgtttt cctgaaagag gaatggcctg    300

ccctggggga tgctgaaatc ctgaaaaaac agctcaaaca atgcagagta agaacagctc    360

tttctttcca tgggttggcc tgaattctta gttccatgta attcacaaaa tcaagttata    420

attgtcttct tttctaaaat ttatattgaa aatacatgca tcacagaaaa tttccctttc    480

aatatgatta aaatgtggtt aataactaca gatttaaaaa caattgacta aatataa       537


<210> SEQ ID NO 2
<211> LENGTH: 636
<212> TYPE: DNA
<213> ORGANISM: Artificial Sequence
<220> FEATURE:
<223> OTHER INFORMATION: Nucleotide sequence of the Pre-Trans-Splicing
      molecule protein, exon 23

<400> SEQUENCE: 2

atatatttc agatttaaaa agaataagta tacaacatgg gatttttaga atcaacaaaa     60

aaattagtct ttatatgtcc tcacatcaca gaagtttctc ttactagtat ttaatttcca    120

gacttaggct attaaaataa ctactcaata ctcgagagat ctccgcggaa cattattata    180

acgttgctcg aatactaact gatatctctt cttttttttt ttccggaaaa caggctctgc    240

aaagttcttt gaaagagcaa caaaatggct tcaactatct gagtgacact gtgaaggaga    300

tggccaagaa agcaccttca gaaatatgcc agaaatatct gtcagaattt gaagagattg    360

aggggcactg gaagaaactt tcctcccagt tggtggaaag ctgccaaaag ctagaagaac    420

atatgaataa gcttcgaaaa tttcaggtaa gaacagctct ttctttccat gggttggcct    480

gaattcttag ttccatgtaa ttcacaaaat caagttataa ttgtcttctt ttctaaaatt    540

tatattgaaa atacatgcat cacagaaaat ttccctttca atatgattaa aatgtggtta    600

ataactacag atttaaaaac aattgactaa atataa                              636


<210> SEQ ID NO 3
<211> LENGTH: 71
<212> TYPE: PRT
<213> ORGANISM: Mus musculus
<220> FEATURE:
<221> NAME/KEY: misc_feature
<223> OTHER INFORMATION: Protein sequence of the murine dystrophin gene
      DMD, exon 23
```

-continued

<400> SEQUENCE: 3

```
Ala Leu Gln Ser Ser Leu Lys Glu Gln Gln Asn Gly Phe Asn Tyr Leu
1               5                   10                  15

Ser Asp Thr Val Lys Glu Met Ala Lys Lys Ala Pro Ser Glu Ile Cys
            20                  25                  30

Gln Lys Tyr Leu Ser Glu Phe Glu Glu Ile Glu Gly His Trp Lys Lys
        35                  40                  45

Leu Ser Ser Gln Leu Val Glu Ser Cys Gln Lys Leu Glu Glu His Met
    50                  55                  60

Asn Lys Leu Arg Lys Phe Gln
65                  70
```

<210> SEQ ID NO 4
<211> LENGTH: 38
<212> TYPE: PRT
<213> ORGANISM: Mus musculus
<220> FEATURE:
<221> NAME/KEY: misc_feature
<223> OTHER INFORMATION: Protein sequence of the murine dystrophin gene DMD, exon 24

<400> SEQUENCE: 4

```
Asn His Ile Lys Thr Leu Gln Lys Trp Met Ala Glu Val Asp Val Phe
1               5                   10                  15

Leu Lys Glu Glu Trp Pro Ala Leu Gly Asp Ala Glu Ile Leu Lys Lys
            20                  25                  30

Gln Leu Lys Gln Cys Arg
        35
```

<210> SEQ ID NO 5
<211> LENGTH: 3678
<212> TYPE: PRT
<213> ORGANISM: Mus musculus
<220> FEATURE:
<221> NAME/KEY: misc_feature
<223> OTHER INFORMATION: Protein sequence of the murine dystrophin gene DMD

<400> SEQUENCE: 5

```
Met Leu Trp Trp Glu Glu Val Glu Asp Cys Tyr Glu Arg Glu Asp Val
1               5                   10                  15

Gln Lys Lys Thr Phe Thr Lys Trp Ile Asn Ala Gln Phe Ser Lys Phe
            20                  25                  30

Gly Lys Gln His Ile Asp Asn Leu Phe Ser Asp Leu Gln Asp Gly Lys
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Lys Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Thr Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160
```

-continued

```
Ser Ser Trp Ser Asp Gly Leu Ala Leu Asn Ala Leu Ile His Ser His
                165                 170                 175

Arg Pro Asp Leu Phe Asp Trp Asn Ser Val Val Ser Gln His Ser Ala
            180                 185                 190

Thr Gln Arg Leu Glu His Ala Phe Asn Ile Ala Lys Cys Gln Leu Gly
        195                 200                 205

Ile Glu Lys Leu Leu Asp Pro Glu Asp Val Ala Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Thr Ser Ser Lys Val Thr Arg Glu Glu His Phe Gln Leu His His Gln
            260                 265                 270

Met His Tyr Ser Gln Gln Ile Thr Val Ser Leu Ala Gln Gly Tyr Glu
        275                 280                 285

Gln Thr Ser Ser Ser Pro Lys Pro Arg Phe Lys Ser Tyr Ala Phe Thr
    290                 295                 300

Gln Ala Ala Tyr Val Ala Thr Ser Asp Ser Thr Gln Ser Pro Tyr Pro
305                 310                 315                 320

Ser Gln His Leu Glu Ala Pro Arg Asp Lys Ser Leu Asp Ser Ser Leu
                325                 330                 335

Met Glu Thr Glu Val Asn Leu Asp Ser Tyr Gln Thr Ala Leu Glu Glu
            340                 345                 350

Val Leu Ser Trp Leu Leu Ser Ala Glu Asp Thr Leu Arg Ala Gln Gly
        355                 360                 365

Glu Ile Ser Asn Asp Val Glu Glu Val Lys Glu Gln Phe His Ala His
    370                 375                 380

Glu Gly Phe Met Met Asp Leu Thr Ser His Gln Gly Leu Val Gly Asn
385                 390                 395                 400

Val Leu Gln Leu Gly Ser Gln Leu Val Gly Lys Gly Lys Leu Ser Glu
                405                 410                 415

Asp Glu Glu Ala Glu Val Gln Glu Gln Met Asn Leu Leu Asn Ser Arg
            420                 425                 430

Trp Glu Cys Leu Arg Val Ala Ser Met Glu Lys Gln Ser Lys Leu His
        435                 440                 445

Lys Val Leu Met Asp Leu Gln Asn Gln Lys Leu Lys Glu Leu Asp Asp
    450                 455                 460

Trp Leu Thr Lys Thr Glu Glu Arg Thr Lys Lys Met Glu Glu Glu Pro
465                 470                 475                 480

Phe Gly Pro Asp Leu Glu Asp Leu Lys Cys Gln Val Gln Gln His Lys
                485                 490                 495

Val Leu Gln Glu Asp Leu Glu Gln Glu Gln Val Arg Val Asn Ser Leu
            500                 505                 510

Thr His Met Val Val Val Val Asp Glu Ser Ser Gly Asp His Ala Thr
        515                 520                 525

Ala Ala Leu Glu Glu Gln Leu Lys Val Leu Gly Asp Arg Trp Ala Asn
    530                 535                 540

Ile Cys Arg Trp Thr Glu Asp Arg Trp Ile Val Leu Gln Asp Ile Leu
545                 550                 555                 560

Leu Lys Trp Gln His Phe Thr Glu Glu Gln Cys Leu Phe Ser Thr Trp
                565                 570                 575
```

-continued

```
Leu Ser Glu Lys Glu Asp Ala Met Lys Asn Ile Gln Thr Ser Gly Phe
            580                 585                 590

Lys Asp Gln Asn Glu Met Met Ser Ser Leu His Lys Ile Ser Thr Leu
        595                 600                 605

Lys Ile Asp Leu Glu Lys Lys Lys Pro Thr Met Glu Lys Leu Ser Ser
    610                 615                 620

Leu Asn Gln Asp Leu Leu Ser Ala Leu Lys Asn Lys Ser Val Thr Gln
625                 630                 635                 640

Lys Met Glu Ile Trp Met Glu Asn Phe Ala Gln Arg Trp Asp Asn Leu
                645                 650                 655

Thr Gln Lys Leu Glu Lys Ser Ser Ala Gln Ile Ser Gln Ala Val Thr
            660                 665                 670

Thr Thr Gln Pro Ser Leu Thr Gln Thr Thr Val Met Glu Thr Val Thr
        675                 680                 685

Met Val Thr Thr Arg Glu Gln Ile Met Val Lys His Ala Gln Glu Glu
    690                 695                 700

Leu Pro Pro Pro Pro Pro Gln Lys Lys Arg Gln Ile Thr Val Asp Ser
705                 710                 715                 720

Glu Leu Arg Lys Arg Leu Asp Val Asp Ile Thr Glu Leu His Ser Trp
                725                 730                 735

Ile Thr Arg Ser Glu Ala Val Leu Gln Ser Ser Glu Phe Ala Val Tyr
            740                 745                 750

Arg Lys Glu Gly Asn Ile Ser Asp Leu Gln Glu Lys Val Asn Ala Ile
        755                 760                 765

Ala Arg Glu Lys Ala Glu Lys Phe Arg Lys Leu Gln Asp Ala Ser Arg
    770                 775                 780

Ser Ala Gln Ala Leu Val Glu Gln Met Ala Asn Glu Gly Val Asn Ala
785                 790                 795                 800

Glu Ser Ile Arg Gln Ala Ser Glu Gln Leu Asn Ser Arg Trp Thr Glu
                805                 810                 815

Phe Cys Gln Leu Leu Ser Glu Arg Val Asn Trp Leu Glu Tyr Gln Thr
            820                 825                 830

Asn Ile Ile Thr Phe Tyr Asn Gln Leu Gln Gln Leu Glu Gln Met Thr
        835                 840                 845

Thr Thr Ala Glu Asn Leu Leu Lys Thr Gln Ser Thr Thr Leu Ser Glu
    850                 855                 860

Pro Thr Ala Ile Lys Ser Gln Leu Lys Ile Cys Lys Asp Glu Val Asn
865                 870                 875                 880

Arg Leu Ser Ala Leu Gln Pro Gln Ile Glu Gln Leu Lys Ile Gln Ser
                885                 890                 895

Leu Gln Leu Lys Glu Lys Gly Gln Gly Pro Met Phe Leu Asp Ala Asp
            900                 905                 910

Phe Val Ala Phe Thr Asn His Phe Asn His Ile Phe Asp Gly Val Arg
        915                 920                 925

Ala Lys Glu Lys Glu Leu Gln Thr Ile Phe Asp Thr Leu Pro Pro Met
    930                 935                 940

Arg Tyr Gln Glu Thr Met Ser Ser Ile Arg Thr Trp Ile Gln Gln Ser
945                 950                 955                 960

Glu Ser Lys Leu Ser Val Pro Tyr Leu Ser Val Thr Glu Tyr Glu Ile
                965                 970                 975

Met Glu Glu Arg Leu Gly Lys Leu Gln Ala Leu Gln Ser Ser Leu Lys
            980                 985                 990

Glu Gln Gln Asn Gly Phe Asn Tyr  Leu Ser Asp Thr Val  Lys Glu Met
```

-continued

```
        995                 1000                1005

Ala Lys  Lys Ala Pro Ser Glu  Ile Cys Gln Lys Tyr  Leu Ser Glu
    1010                 1015                 1020

Phe Glu  Glu Ile Glu Gly His  Trp Lys Lys Leu Ser  Ser Gln Leu
    1025                 1030                 1035

Val Glu  Ser Cys Gln Lys Leu  Glu Glu His Met Asn  Lys Leu Arg
    1040                 1045                 1050

Lys Phe  Gln Asn His Ile Lys  Thr Leu Gln Lys Trp  Met Ala Glu
    1055                 1060                 1065

Val Asp  Val Phe Leu Lys Glu  Glu Trp Pro Ala Leu  Gly Asp Ala
    1070                 1075                 1080

Glu Ile  Leu Lys Lys Gln Leu  Lys Gln Cys Arg Leu  Leu Val Gly
    1085                 1090                 1095

Asp Ile  Gln Thr Ile Gln Pro  Ser Leu Asn Ser Val  Asn Glu Gly
    1100                 1105                 1110

Gly Gln  Lys Ile Lys Ser Glu  Ala Glu Leu Glu Phe  Ala Ser Arg
    1115                 1120                 1125

Leu Glu  Thr Glu Leu Arg Glu  Leu Asn Thr Gln Trp  Asp His Ile
    1130                 1135                 1140

Cys Arg  Gln Val Tyr Thr Arg  Lys Glu Ala Leu Lys  Ala Gly Leu
    1145                 1150                 1155

Asp Lys  Thr Val Ser Leu Gln  Lys Asp Leu Ser Glu  Met His Glu
    1160                 1165                 1170

Trp Met  Thr Gln Ala Glu Glu  Glu Tyr Leu Glu Arg  Asp Phe Glu
    1175                 1180                 1185

Tyr Lys  Thr Pro Asp Glu Leu  Gln Thr Ala Val Glu  Glu Met Lys
    1190                 1195                 1200

Arg Ala  Lys Glu Glu Ala Leu  Gln Lys Glu Thr Lys  Val Lys Leu
    1205                 1210                 1215

Leu Thr  Glu Thr Val Asn Ser  Val Ile Ala His Ala  Pro Pro Ser
    1220                 1225                 1230

Ala Gln  Glu Ala Leu Lys Lys  Glu Leu Glu Thr Leu  Thr Thr Asn
    1235                 1240                 1245

Tyr Gln  Trp Leu Cys Thr Arg  Leu Asn Gly Lys Cys  Lys Thr Leu
    1250                 1255                 1260

Glu Glu  Val Trp Ala Cys Trp  His Glu Leu Leu Ser  Tyr Leu Glu
    1265                 1270                 1275

Lys Ala  Asn Lys Trp Leu Asn  Glu Val Glu Leu Lys  Leu Lys Thr
    1280                 1285                 1290

Met Glu  Asn Val Pro Ala Gly  Pro Glu Glu Ile Thr  Glu Val Leu
    1295                 1300                 1305

Glu Ser  Leu Glu Asn Leu Met  His His Ser Glu Glu  Asn Pro Asn
    1310                 1315                 1320

Gln Ile  Arg Leu Leu Ala Gln  Thr Leu Thr Asp Gly  Gly Val Met
    1325                 1330                 1335

Asp Glu  Leu Ile Asn Glu Glu  Leu Glu Thr Phe Asn  Ser Arg Trp
    1340                 1345                 1350

Arg Glu  Leu His Glu Glu Ala  Val Arg Lys Gln Lys  Leu Leu Glu
    1355                 1360                 1365

Gln Ser  Ile Gln Ser Ala Gln  Glu Ile Glu Lys Ser  Leu His Leu
    1370                 1375                 1380

Ile Gln  Glu Ser Leu Glu Phe  Ile Asp Lys Gln Leu  Ala Ala Tyr
    1385                 1390                 1395
```

-continued

```
Ile Thr  Asp Lys Val Asp Ala  Ala Gln Met Pro Gln  Glu Ala Gln
    1400                 1405                 1410

Lys Ile  Gln Ser Asp Leu Thr  Ser His Glu Ile Ser  Leu Glu Glu
    1415                 1420                 1425

Met Lys  Lys His Asn Gln Gly  Lys Asp Ala Asn Gln  Arg Val Leu
    1430                 1435                 1440

Ser Gln  Ile Asp Val Ala Gln  Lys Lys Leu Gln Asp  Val Ser Met
    1445                 1450                 1455

Lys Phe  Arg Leu Phe Gln Lys  Pro Ala Asn Phe Glu  Gln Arg Leu
    1460                 1465                 1470

Glu Glu  Ser Lys Met Ile Leu  Asp Glu Val Lys Met  His Leu Pro
    1475                 1480                 1485

Ala Leu  Glu Thr Lys Ser Val  Glu Gln Glu Val Ile  Gln Ser Gln
    1490                 1495                 1500

Leu Ser  His Cys Val Asn Leu  Tyr Lys Ser Leu Ser  Glu Val Lys
    1505                 1510                 1515

Ser Glu  Val Glu Met Val Ile  Lys Thr Gly Arg Gln  Ile Val Gln
    1520                 1525                 1530

Lys Lys  Gln Thr Glu Asn Pro  Lys Glu Leu Asp Glu  Arg Val Thr
    1535                 1540                 1545

Ala Leu  Lys Leu His Tyr Asn  Glu Leu Gly Ala Lys  Val Thr Glu
    1550                 1555                 1560

Arg Lys  Gln Gln Leu Glu Lys  Cys Leu Lys Leu Ser  Arg Lys Met
    1565                 1570                 1575

Arg Lys  Glu Met Asn Val Leu  Thr Glu Trp Leu Ala  Ala Thr Asp
    1580                 1585                 1590

Thr Glu  Leu Thr Lys Arg Ser  Ala Val Glu Gly Met  Pro Ser Asn
    1595                 1600                 1605

Leu Asp  Ser Glu Val Ala Trp  Gly Lys Ala Thr Gln  Lys Glu Ile
    1610                 1615                 1620

Glu Lys  Gln Lys Ala His Leu  Lys Ser Val Thr Glu  Leu Gly Glu
    1625                 1630                 1635

Ser Leu  Lys Met Val Leu Gly  Lys Lys Glu Thr Leu  Val Glu Asp
    1640                 1645                 1650

Lys Leu  Ser Leu Leu Asn Ser  Asn Trp Ile Ala Val  Thr Ser Arg
    1655                 1660                 1665

Val Glu  Glu Trp Leu Asn Leu  Leu Leu Glu Tyr Gln  Lys His Met
    1670                 1675                 1680

Glu Thr  Phe Asp Gln Asn Ile  Glu Gln Ile Thr Lys  Trp Ile Ile
    1685                 1690                 1695

His Ala  Asp Glu Leu Leu Asp  Glu Ser Glu Lys Lys  Lys Pro Gln
    1700                 1705                 1710

Gln Lys  Glu Asp Ile Leu Lys  Arg Leu Lys Ala Glu  Met Asn Asp
    1715                 1720                 1725

Met Arg  Pro Lys Val Asp Ser  Thr Arg Asp Gln Ala  Ala Lys Leu
    1730                 1735                 1740

Met Ala  Asn Arg Gly Asp His  Cys Arg Lys Val Val  Glu Pro Gln
    1745                 1750                 1755

Ile Ser  Glu Leu Asn Arg Arg  Phe Ala Ala Ile Ser  His Arg Ile
    1760                 1765                 1770

Lys Thr  Gly Lys Ala Ser Ile  Pro Leu Lys Glu Leu  Glu Gln Phe
    1775                 1780                 1785
```

```
Asn Ser  Asp Ile Gln Lys Leu  Leu Glu Pro Leu Glu  Ala Glu Ile
    1790                 1795                 1800

Gln Gln  Gly Val Asn Leu Lys  Glu Glu Asp Phe Asn  Lys Asp Met
    1805                 1810                 1815

Ser Glu  Asp Asn Glu Gly Thr  Val Asn Glu Leu Leu  Gln Arg Gly
    1820                 1825                 1830

Asp Asn  Leu Gln Gln Arg Ile  Thr Asp Glu Arg Lys  Arg Glu Glu
    1835                 1840                 1845

Ile Lys  Ile Lys Gln Gln Leu  Leu Gln Thr Lys His  Asn Ala Leu
    1850                 1855                 1860

Lys Asp  Leu Arg Ser Gln Arg  Arg Lys Lys Ala Leu  Glu Ile Ser
    1865                 1870                 1875

His Gln  Trp Tyr Gln Tyr Lys  Arg Gln Ala Asp Asp  Leu Leu Lys
    1880                 1885                 1890

Cys Leu  Asp Glu Ile Glu Lys  Lys Leu Ala Ser Leu  Pro Glu Pro
    1895                 1900                 1905

Arg Asp  Glu Arg Lys Leu Lys  Glu Ile Asp Arg Glu  Leu Gln Lys
    1910                 1915                 1920

Lys Lys  Glu Glu Leu Asn Ala  Val Arg Arg Gln Ala  Glu Gly Leu
    1925                 1930                 1935

Ser Glu  Asn Gly Ala Ala Met  Ala Val Glu Pro Thr  Gln Ile Gln
    1940                 1945                 1950

Leu Ser  Lys Arg Trp Arg Gln  Ile Glu Ser Asn Phe  Ala Gln Phe
    1955                 1960                 1965

Arg Arg  Leu Asn Phe Ala Gln  Ile His Thr Leu His  Glu Glu Thr
    1970                 1975                 1980

Met Val  Val Thr Thr Glu Asp  Met Pro Leu Asp Val  Ser Tyr Val
    1985                 1990                 1995

Pro Ser  Thr Tyr Leu Thr Glu  Ile Ser His Ile Leu  Gln Ala Leu
    2000                 2005                 2010

Ser Glu  Val Asp His Leu Leu  Asn Thr Pro Glu Leu  Cys Ala Lys
    2015                 2020                 2025

Asp Phe  Glu Asp Leu Phe Lys  Gln Glu Glu Ser Leu  Lys Asn Ile
    2030                 2035                 2040

Lys Asp  Asn Leu Gln Gln Ile  Ser Gly Arg Ile Asp  Ile Ile His
    2045                 2050                 2055

Lys Lys  Lys Thr Ala Ala Leu  Gln Ser Ala Thr Ser  Met Glu Lys
    2060                 2065                 2070

Val Lys  Val Gln Glu Ala Val  Ala Gln Met Asp Phe  Gln Gly Glu
    2075                 2080                 2085

Lys Leu  His Arg Met Tyr Lys  Glu Arg Gln Gly Arg  Phe Asp Arg
    2090                 2095                 2100

Ser Val  Glu Lys Trp Arg His  Phe His Tyr Asp Met  Lys Val Phe
    2105                 2110                 2115

Asn Gln  Trp Leu Asn Glu Val  Glu Gln Phe Phe Lys  Lys Thr Gln
    2120                 2125                 2130

Asn Pro  Glu Asn Trp Glu His  Ala Lys Tyr Lys Trp  Tyr Leu Lys
    2135                 2140                 2145

Glu Leu  Gln Asp Gly Ile Gly  Gln Arg Gln Ala Val  Val Arg Thr
    2150                 2155                 2160

Leu Asn  Ala Thr Gly Glu Glu  Ile Ile Gln Gln Ser  Ser Lys Thr
    2165                 2170                 2175

Asp Val  Asn Ile Leu Gln Glu  Lys Leu Gly Ser Leu  Ser Leu Arg
```

```
    2180                 2185                 2190

Trp His  Asp Ile Cys Lys Glu  Leu Ala Glu Arg Arg  Lys Arg Ile
    2195                 2200                 2205

Glu Glu  Gln Lys Asn Val Leu  Ser Glu Phe Gln Arg  Asp Leu Asn
    2210                 2215                 2220

Glu Phe  Val Leu Trp Leu Glu  Glu Ala Asp Asn Ile  Ala Ile Thr
    2225                 2230                 2235

Pro Leu  Gly Asp Glu Gln Gln  Leu Lys Glu Gln Leu  Glu Gln Val
    2240                 2245                 2250

Lys Leu  Leu Ala Glu Glu Leu  Pro Leu Arg Gln Gly  Ile Leu Lys
    2255                 2260                 2265

Gln Leu  Asn Glu Thr Gly Gly  Ala Val Leu Val Ser  Ala Pro Ile
    2270                 2275                 2280

Arg Pro  Glu Glu Gln Asp Lys  Leu Glu Lys Lys Leu  Lys Gln Thr
    2285                 2290                 2295

Asn Leu  Gln Trp Ile Lys Val  Ser Arg Ala Leu Pro  Glu Lys Gln
    2300                 2305                 2310

Gly Glu  Leu Glu Val His Leu  Lys Asp Phe Arg Gln  Leu Glu Glu
    2315                 2320                 2325

Gln Leu  Asp His Leu Leu Leu  Trp Leu Ser Pro Ile  Arg Asn Gln
    2330                 2335                 2340

Leu Glu  Ile Tyr Asn Gln Pro  Ser Gln Ala Gly Pro  Phe Asp Ile
    2345                 2350                 2355

Lys Glu  Ile Glu Val Thr Val  His Gly Lys Gln Ala  Asp Val Glu
    2360                 2365                 2370

Arg Leu  Leu Ser Lys Gly Gln  His Leu Tyr Lys Glu  Lys Pro Ser
    2375                 2380                 2385

Thr Gln  Pro Val Lys Arg Lys  Leu Glu Asp Leu Arg  Ser Glu Trp
    2390                 2395                 2400

Glu Ala  Val Asn His Leu Leu  Arg Glu Leu Arg Thr  Lys Gln Pro
    2405                 2410                 2415

Asp Arg  Ala Pro Gly Leu Ser  Thr Thr Gly Ala Ser  Ala Ser Gln
    2420                 2425                 2430

Thr Val  Thr Leu Val Thr Gln  Ser Val Val Thr Lys  Glu Thr Val
    2435                 2440                 2445

Ile Ser  Lys Leu Glu Met Pro  Ser Ser Leu Leu Leu  Glu Val Pro
    2450                 2455                 2460

Ala Leu  Ala Asp Phe Asn Arg  Ala Trp Thr Glu Leu  Thr Asp Trp
    2465                 2470                 2475

Leu Ser  Leu Leu Asp Arg Val  Ile Lys Ser Gln Arg  Val Met Val
    2480                 2485                 2490

Gly Asp  Leu Glu Asp Ile Asn  Glu Met Ile Ile Lys  Gln Lys Ala
    2495                 2500                 2505

Thr Leu  Gln Asp Leu Glu Gln  Arg Arg Pro Gln Leu  Glu Glu Leu
    2510                 2515                 2520

Ile Thr  Ala Ala Gln Asn Leu  Lys Asn Lys Thr Ser  Asn Gln Glu
    2525                 2530                 2535

Ala Arg  Thr Ile Ile Thr Asp  Arg Ile Glu Arg Ile  Gln Ile Gln
    2540                 2545                 2550

Trp Asp  Glu Val Gln Glu Gln  Leu Gln Asn Arg Arg  Gln Gln Leu
    2555                 2560                 2565

Asn Glu  Met Leu Lys Asp Ser  Thr Gln Trp Leu Glu  Ala Lys Glu
    2570                 2575                 2580
```

-continued

```
Glu Ala  Glu Gln Val Ile Gly  Gln Val Arg Gly Lys  Leu Asp Ser
    2585                 2590                 2595

Trp Lys  Glu Gly Pro His Thr  Val Asp Ala Ile Gln  Lys Lys Ile
    2600                 2605                 2610

Thr Glu  Thr Lys Gln Leu Ala  Lys Asp Leu Arg Gln  Arg Gln Ile
    2615                 2620                 2625

Ser Val  Asp Val Ala Asn Asp  Leu Ala Leu Lys Leu  Leu Arg Asp
    2630                 2635                 2640

Tyr Ser  Ala Asp Asp Thr Arg  Lys Val His Met Ile  Thr Glu Asn
    2645                 2650                 2655

Ile Asn  Thr Ser Trp Gly Asn  Ile His Lys Arg Val  Ser Glu Gln
    2660                 2665                 2670

Glu Ala  Ala Leu Glu Glu Thr  His Arg Leu Leu Gln  Gln Phe Pro
    2675                 2680                 2685

Leu Asp  Leu Glu Lys Phe Leu  Ser Trp Ile Thr Glu  Ala Glu Thr
    2690                 2695                 2700

Thr Ala  Asn Val Leu Gln Asp  Ala Ser Arg Lys Glu  Lys Leu Leu
    2705                 2710                 2715

Glu Asp  Ser Arg Gly Val Arg  Glu Leu Met Lys Pro  Trp Gln Asp
    2720                 2725                 2730

Leu Gln  Gly Glu Ile Glu Thr  His Thr Asp Ile Tyr  His Asn Leu
    2735                 2740                 2745

Asp Glu  Asn Gly Gln Lys Ile  Leu Arg Ser Leu Glu  Gly Ser Asp
    2750                 2755                 2760

Glu Ala  Pro Leu Leu Gln Arg  Arg Leu Asp Asn Met  Asn Phe Lys
    2765                 2770                 2775

Trp Ser  Glu Leu Gln Lys Lys  Ser Leu Asn Ile Arg  Ser His Leu
    2780                 2785                 2790

Glu Ala  Ser Ser Asp Gln Trp  Lys Arg Leu His Leu  Ser Leu Gln
    2795                 2800                 2805

Glu Leu  Leu Val Trp Leu Gln  Leu Lys Asp Asp Glu  Leu Ser Arg
    2810                 2815                 2820

Gln Ala  Pro Ile Gly Gly Asp  Phe Pro Ala Val Gln  Lys Gln Asn
    2825                 2830                 2835

Asp Ile  His Arg Ala Phe Lys  Arg Glu Leu Lys Thr  Lys Glu Pro
    2840                 2845                 2850

Val Ile  Met Ser Thr Leu Glu  Thr Val Arg Ile Phe  Leu Thr Glu
    2855                 2860                 2865

Gln Pro  Leu Glu Gly Leu Glu  Lys Leu Tyr Gln Glu  Pro Arg Glu
    2870                 2875                 2880

Leu Pro  Pro Glu Glu Arg Ala  Gln Asn Val Thr Arg  Leu Leu Arg
    2885                 2890                 2895

Lys Gln  Ala Glu Glu Val Asn  Ala Glu Trp Asp Lys  Leu Asn Leu
    2900                 2905                 2910

Arg Ser  Ala Asp Trp Gln Arg  Lys Ile Asp Glu Ala  Leu Glu Arg
    2915                 2920                 2925

Leu Gln  Glu Leu Gln Glu Ala  Ala Asp Glu Leu Asp  Leu Lys Leu
    2930                 2935                 2940

Arg Gln  Ala Glu Val Ile Lys  Gly Ser Trp Gln Pro  Val Gly Asp
    2945                 2950                 2955

Leu Leu  Ile Asp Ser Leu Gln  Asp His Leu Glu Lys  Val Lys Ala
    2960                 2965                 2970
```

-continued

```
Leu Arg  Gly Glu Ile Ala Pro  Leu Lys Glu Asn Val  Asn Arg Val
    2975                 2980                 2985

Asn Asp  Leu Ala His Gln Leu  Thr Thr Leu Gly Ile  Gln Leu Ser
    2990                 2995                 3000

Pro Tyr  Asn Leu Ser Thr Leu  Glu Asp Leu Asn Thr  Arg Trp Arg
    3005                 3010                 3015

Leu Leu  Gln Val Ala Val Glu  Asp Arg Val Arg Gln  Leu His Glu
    3020                 3025                 3030

Ala His  Arg Asp Phe Gly Pro  Ala Ser Gln His Phe  Leu Ser Thr
    3035                 3040                 3045

Ser Val  Gln Gly Pro Trp Glu  Arg Ala Ile Ser Pro  Asn Lys Val
    3050                 3055                 3060

Pro Tyr  Tyr Ile Asn His Glu  Thr Gln Thr Thr Cys  Trp Asp His
    3065                 3070                 3075

Pro Lys  Met Thr Glu Leu Tyr  Gln Ser Leu Ala Asp  Leu Asn Asn
    3080                 3085                 3090

Val Arg  Phe Ser Ala Tyr Arg  Thr Ala Met Lys Leu  Arg Arg Leu
    3095                 3100                 3105

Gln Lys  Ala Leu Cys Leu Asp  Leu Leu Ser Leu Ser  Ala Ala Cys
    3110                 3115                 3120

Asp Ala  Leu Asp Gln His Asn  Leu Lys Gln Asn Asp  Gln Pro Met
    3125                 3130                 3135

Asp Ile  Leu Gln Ile Ile Asn  Cys Leu Thr Thr Ile  Tyr Asp Arg
    3140                 3145                 3150

Leu Glu  Gln Glu His Asn Asn  Leu Val Asn Val Pro  Leu Cys Val
    3155                 3160                 3165

Asp Met  Cys Leu Asn Trp Leu  Leu Asn Val Tyr Asp  Thr Gly Arg
    3170                 3175                 3180

Thr Gly  Arg Ile Arg Val Leu  Ser Phe Lys Thr Gly  Ile Ile Ser
    3185                 3190                 3195

Leu Cys  Lys Ala His Leu Glu  Asp Lys Tyr Arg Tyr  Leu Phe Lys
    3200                 3205                 3210

Gln Val  Ala Ser Ser Thr Gly  Phe Cys Asp Gln Arg  Arg Leu Gly
    3215                 3220                 3225

Leu Leu  Leu His Asp Ser Ile  Gln Ile Pro Arg Gln  Leu Gly Glu
    3230                 3235                 3240

Val Ala  Ser Phe Gly Gly Ser  Asn Ile Glu Pro Ser  Val Arg Ser
    3245                 3250                 3255

Cys Phe  Gln Phe Ala Asn Asn  Lys Pro Glu Ile Glu  Ala Ala Leu
    3260                 3265                 3270

Phe Leu  Asp Trp Met Arg Leu  Glu Pro Gln Ser Met  Val Trp Leu
    3275                 3280                 3285

Pro Val  Leu His Arg Val Ala  Ala Ala Glu Thr Ala  Lys His Gln
    3290                 3295                 3300

Ala Lys  Cys Asn Ile Cys Lys  Glu Cys Pro Ile Ile  Gly Phe Arg
    3305                 3310                 3315

Tyr Arg  Ser Leu Lys His Phe  Asn Tyr Asp Ile Cys  Gln Ser Cys
    3320                 3325                 3330

Phe Phe  Ser Gly Arg Val Ala  Lys Gly His Lys Met  His Tyr Pro
    3335                 3340                 3345

Met Val  Glu Tyr Cys Thr Pro  Thr Thr Ser Gly Glu  Asp Val Arg
    3350                 3355                 3360

Asp Phe  Ala Lys Val Leu Lys  Asn Lys Phe Arg Thr  Lys Arg Tyr
```

```
    3365                3370                3375

Phe Ala  Lys His Pro Arg Met  Gly Tyr Leu Pro Val  Gln Thr Val
    3380                3385                3390

Leu Glu  Gly Asp Asn Met Glu  Thr Pro Val Thr Leu  Ile Asn Phe
    3395                3400                3405

Trp Pro  Val Asp Ser Ala Pro  Ala Ser Ser Pro Gln  Leu Ser His
    3410                3415                3420

Asp Asp  Thr His Ser Arg Ile  Glu His Tyr Ala Ser  Arg Leu Ala
    3425                3430                3435

Glu Met  Glu Asn Ser Asn Gly  Ser Tyr Leu Asn Asp  Ser Ile Ser
    3440                3445                3450

Pro Asn  Glu Ser Ile Asp Asp  Glu His Leu Leu Ile  Gln His Tyr
    3455                3460                3465

Cys Gln  Ser Leu Asn Gln Asp  Ser Pro Leu Ser Gln  Pro Arg Ser
    3470                3475                3480

Pro Ala  Gln Ile Leu Ile Ser  Leu Glu Ser Glu Glu  Arg Gly Glu
    3485                3490                3495

Leu Glu  Arg Ile Leu Ala Asp  Leu Glu Glu Glu Asn  Arg Asn Leu
    3500                3505                3510

Gln Ala  Glu Tyr Asp Arg Leu  Lys Gln Gln His Glu  His Lys Gly
    3515                3520                3525

Leu Ser  Pro Leu Pro Ser Pro  Pro Glu Met Met Pro  Thr Ser Pro
    3530                3535                3540

Gln Ser  Pro Arg Asp Ala Glu  Leu Ile Ala Glu Ala  Lys Leu Leu
    3545                3550                3555

Arg Gln  His Lys Gly Arg Leu  Glu Ala Arg Met Gln  Ile Leu Glu
    3560                3565                3570

Asp His  Asn Lys Gln Leu Glu  Ser Gln Leu His Arg  Leu Arg Gln
    3575                3580                3585

Leu Leu  Glu Gln Pro Gln Ala  Glu Ala Lys Val Asn  Gly Thr Thr
    3590                3595                3600

Val Ser  Ser Pro Ser Thr Ser  Leu Gln Arg Ser Asp  Ser Ser Gln
    3605                3610                3615

Pro Met  Leu Leu Arg Val Val  Gly Ser Gln Thr Ser  Glu Ser Met
    3620                3625                3630

Gly Glu  Glu Asp Leu Leu Ser  Pro Pro Gln Asp Thr  Ser Thr Gly
    3635                3640                3645

Leu Glu  Glu Val Met Glu Gln  Leu Asn Asn Ser Phe  Pro Ser Ser
    3650                3655                3660

Arg Gly  Arg Asn Ala Pro Gly  Lys Pro Met Arg Glu  Asp Thr Met
    3665                3670                3675


<210> SEQ ID NO 6
<211> LENGTH: 3685
<212> TYPE: PRT
<213> ORGANISM: Homo sapiens
<220> FEATURE:
<221> NAME/KEY: misc_feature
<223> OTHER INFORMATION: Protein sequence of the human dystrophin gene
      DMD

<400> SEQUENCE: 6

Met Leu Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30
```

-continued

```
Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445
```

-continued

```
Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Ile Leu Leu Lys
545                 550                 555                 560

Trp Gln Arg Leu Thr Glu Glu Gln Cys Leu Phe Ser Ala Trp Leu Ser
                565                 570                 575

Glu Lys Glu Asp Ala Val Asn Lys Ile His Thr Thr Gly Phe Lys Asp
            580                 585                 590

Gln Asn Glu Met Leu Ser Ser Leu Gln Lys Leu Ala Val Leu Lys Ala
        595                 600                 605

Asp Leu Glu Lys Lys Lys Gln Ser Met Gly Lys Leu Tyr Ser Leu Lys
    610                 615                 620

Gln Asp Leu Leu Ser Thr Leu Lys Asn Lys Ser Val Thr Gln Lys Thr
625                 630                 635                 640

Glu Ala Trp Leu Asp Asn Phe Ala Arg Cys Trp Asp Asn Leu Val Gln
                645                 650                 655

Lys Leu Glu Lys Ser Thr Ala Gln Ile Ser Gln Ala Val Thr Thr Thr
            660                 665                 670

Gln Pro Ser Leu Thr Gln Thr Thr Val Met Glu Thr Val Thr Thr Val
        675                 680                 685

Thr Thr Arg Glu Gln Ile Leu Val Lys His Ala Gln Glu Glu Leu Pro
    690                 695                 700

Pro Pro Pro Pro Gln Lys Lys Arg Gln Ile Thr Val Asp Ser Glu Ile
705                 710                 715                 720

Arg Lys Arg Leu Asp Val Asp Ile Thr Glu Leu His Ser Trp Ile Thr
                725                 730                 735

Arg Ser Glu Ala Val Leu Gln Ser Pro Glu Phe Ala Ile Phe Arg Lys
            740                 745                 750

Glu Gly Asn Phe Ser Asp Leu Lys Glu Lys Val Asn Ala Ile Glu Arg
        755                 760                 765

Glu Lys Ala Glu Lys Phe Arg Lys Leu Gln Asp Ala Ser Arg Ser Ala
    770                 775                 780

Gln Ala Leu Val Glu Gln Met Val Asn Glu Gly Val Asn Ala Asp Ser
785                 790                 795                 800

Ile Lys Gln Ala Ser Glu Gln Leu Asn Ser Arg Trp Ile Glu Phe Cys
                805                 810                 815

Gln Leu Leu Ser Glu Arg Leu Asn Trp Leu Glu Tyr Gln Asn Asn Ile
            820                 825                 830

Ile Ala Phe Tyr Asn Gln Leu Gln Gln Leu Glu Gln Met Thr Thr Thr
        835                 840                 845

Ala Glu Asn Trp Leu Lys Ile Gln Pro Thr Thr Pro Ser Glu Pro Thr
    850                 855                 860

Ala Ile Lys Ser Gln Leu Lys Ile Cys Lys Asp Glu Val Asn Arg Leu
```

-continued

```
865                 870                 875                 880

Ser Gly Leu Gln Pro Gln Ile Glu Arg Leu Lys Ile Gln Ser Ile Ala
                885                 890                 895

Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser  Thr Thr Val Lys Glu  Met Ser Lys
        995                 1000                1005

Lys Ala  Pro Ser Glu Ile Ser  Arg Lys Tyr Gln Ser  Glu Phe Glu
    1010                1015                1020

Glu Ile  Glu Gly Arg Trp Lys  Lys Leu Ser Ser Gln  Leu Val Glu
    1025                1030                1035

His Cys  Gln Lys Leu Glu Glu  Gln Met Asn Lys Leu  Arg Lys Ile
    1040                1045                1050

Gln Asn  His Ile Gln Thr Leu  Lys Lys Trp Met Ala  Glu Val Asp
    1055                1060                1065

Val Phe  Leu Lys Glu Glu Trp  Pro Ala Leu Gly Asp  Ser Glu Ile
    1070                1075                1080

Leu Lys  Lys Gln Leu Lys Gln  Cys Arg Leu Leu Val  Ser Asp Ile
    1085                1090                1095

Gln Thr  Ile Gln Pro Ser Leu  Asn Ser Val Asn Glu  Gly Gly Gln
    1100                1105                1110

Lys Ile  Lys Asn Glu Ala Glu  Pro Glu Phe Ala Ser  Arg Leu Glu
    1115                1120                1125

Thr Glu  Leu Lys Glu Leu Asn  Thr Gln Trp Asp His  Met Cys Gln
    1130                1135                1140

Gln Val  Tyr Ala Arg Lys Glu  Ala Leu Lys Gly Gly  Leu Glu Lys
    1145                1150                1155

Thr Val  Ser Leu Gln Lys Asp  Leu Ser Glu Met His  Glu Trp Met
    1160                1165                1170

Thr Gln  Ala Glu Glu Glu Tyr  Leu Glu Arg Asp Phe  Glu Tyr Lys
    1175                1180                1185

Thr Pro  Asp Glu Leu Gln Lys  Ala Val Glu Glu Met  Lys Arg Ala
    1190                1195                1200

Lys Glu  Glu Ala Gln Gln Lys  Glu Ala Lys Val Lys  Leu Leu Thr
    1205                1210                1215

Glu Ser  Val Asn Ser Val Ile  Ala Gln Ala Pro Pro  Val Ala Gln
    1220                1225                1230

Glu Ala  Leu Lys Lys Glu Leu  Glu Thr Leu Thr Thr  Asn Tyr Gln
    1235                1240                1245

Trp Leu  Cys Thr Arg Leu Asn  Gly Lys Cys Lys Thr  Leu Glu Glu
    1250                1255                1260

Val Trp  Ala Cys Trp His Glu  Leu Leu Ser Tyr Leu  Glu Lys Ala
    1265                1270                1275
```

-continued

```
Asn Lys  Trp Leu Asn Glu Val  Glu Phe Lys Leu Lys  Thr Thr Glu
    1280                 1285                 1290

Asn Ile  Pro Gly Gly Ala Glu  Glu Ile Ser Glu Val  Leu Asp Ser
    1295                 1300                 1305

Leu Glu  Asn Leu Met Arg His  Ser Glu Asp Asn Pro  Asn Gln Ile
    1310                 1315                 1320

Arg Ile  Leu Ala Gln Thr Leu  Thr Asp Gly Gly Val  Met Asp Glu
    1325                 1330                 1335

Leu Ile  Asn Glu Glu Leu Glu  Thr Phe Asn Ser Arg  Trp Arg Glu
    1340                 1345                 1350

Leu His  Glu Glu Ala Val Arg  Arg Gln Lys Leu Leu  Glu Gln Ser
    1355                 1360                 1365

Ile Gln  Ser Ala Gln Glu Thr  Glu Lys Ser Leu His  Leu Ile Gln
    1370                 1375                 1380

Glu Ser  Leu Thr Phe Ile Asp  Lys Gln Leu Ala Ala  Tyr Ile Ala
    1385                 1390                 1395

Asp Lys  Val Asp Ala Ala Gln  Met Pro Gln Glu Ala  Gln Lys Ile
    1400                 1405                 1410

Gln Ser  Asp Leu Thr Ser His  Glu Ile Ser Leu Glu  Glu Met Lys
    1415                 1420                 1425

Lys His  Asn Gln Gly Lys Glu  Ala Ala Gln Arg Val  Leu Ser Gln
    1430                 1435                 1440

Ile Asp  Val Ala Gln Lys Lys  Leu Gln Asp Val Ser  Met Lys Phe
    1445                 1450                 1455

Arg Leu  Phe Gln Lys Pro Ala  Asn Phe Glu Gln Arg  Leu Gln Glu
    1460                 1465                 1470

Ser Lys  Met Ile Leu Asp Glu  Val Lys Met His Leu  Pro Ala Leu
    1475                 1480                 1485

Glu Thr  Lys Ser Val Glu Gln  Glu Val Val Gln Ser  Gln Leu Asn
    1490                 1495                 1500

His Cys  Val Asn Leu Tyr Lys  Ser Leu Ser Glu Val  Lys Ser Glu
    1505                 1510                 1515

Val Glu  Met Val Ile Lys Thr  Gly Arg Gln Ile Val  Gln Lys Lys
    1520                 1525                 1530

Gln Thr  Glu Asn Pro Lys Glu  Leu Asp Glu Arg Val  Thr Ala Leu
    1535                 1540                 1545

Lys Leu  His Tyr Asn Glu Leu  Gly Ala Lys Val Thr  Glu Arg Lys
    1550                 1555                 1560

Gln Gln  Leu Glu Lys Cys Leu  Lys Leu Ser Arg Lys  Met Arg Lys
    1565                 1570                 1575

Glu Met  Asn Val Leu Thr Glu  Trp Leu Ala Ala Thr  Asp Met Glu
    1580                 1585                 1590

Leu Thr  Lys Arg Ser Ala Val  Glu Gly Met Pro Ser  Asn Leu Asp
    1595                 1600                 1605

Ser Glu  Val Ala Trp Gly Lys  Ala Thr Gln Lys Glu  Ile Glu Lys
    1610                 1615                 1620

Gln Lys  Val His Leu Lys Ser  Ile Thr Glu Val Gly  Glu Ala Leu
    1625                 1630                 1635

Lys Thr  Val Leu Gly Lys Lys  Glu Thr Leu Val Glu  Asp Lys Leu
    1640                 1645                 1650

Ser Leu  Leu Asn Ser Asn Trp  Ile Ala Val Thr Ser  Arg Ala Glu
    1655                 1660                 1665
```

-continued

```
Glu Trp  Leu Asn Leu Leu Leu  Glu Tyr Gln Lys His  Met Glu Thr
    1670                 1675                 1680

Phe Asp  Gln Asn Val Asp His  Ile Thr Lys Trp Ile  Ile Gln Ala
    1685                 1690                 1695

Asp Thr  Leu Leu Asp Glu Ser  Glu Lys Lys Lys Pro  Gln Gln Lys
    1700                 1705                 1710

Glu Asp  Val Leu Lys Arg Leu  Lys Ala Glu Leu Asn  Asp Ile Arg
    1715                 1720                 1725

Pro Lys  Val Asp Ser Thr Arg  Asp Gln Ala Ala Asn  Leu Met Ala
    1730                 1735                 1740

Asn Arg  Gly Asp His Cys Arg  Lys Leu Val Glu Pro  Gln Ile Ser
    1745                 1750                 1755

Glu Leu  Asn His Arg Phe Ala  Ala Ile Ser His Arg  Ile Lys Thr
    1760                 1765                 1770

Gly Lys  Ala Ser Ile Pro Leu  Lys Glu Leu Glu Gln  Phe Asn Ser
    1775                 1780                 1785

Asp Ile  Gln Lys Leu Leu Glu  Pro Leu Glu Ala Glu  Ile Gln Gln
    1790                 1795                 1800

Gly Val  Asn Leu Lys Glu Glu  Asp Phe Asn Lys Asp  Met Asn Glu
    1805                 1810                 1815

Asp Asn  Glu Gly Thr Val Lys  Glu Leu Leu Gln Arg  Gly Asp Asn
    1820                 1825                 1830

Leu Gln  Gln Arg Ile Thr Asp  Glu Arg Lys Arg Glu  Glu Ile Lys
    1835                 1840                 1845

Ile Lys  Gln Gln Leu Leu Gln  Thr Lys His Asn Ala  Leu Lys Asp
    1850                 1855                 1860

Leu Arg  Ser Gln Arg Arg Lys  Lys Ala Leu Glu Ile  Ser His Gln
    1865                 1870                 1875

Trp Tyr  Gln Tyr Lys Arg Gln  Ala Asp Asp Leu Leu  Lys Cys Leu
    1880                 1885                 1890

Asp Asp  Ile Glu Lys Lys Leu  Ala Ser Leu Pro Glu  Pro Arg Asp
    1895                 1900                 1905

Glu Arg  Lys Ile Lys Glu Ile  Asp Arg Glu Leu Gln  Lys Lys Lys
    1910                 1915                 1920

Glu Glu  Leu Asn Ala Val Arg  Arg Gln Ala Glu Gly  Leu Ser Glu
    1925                 1930                 1935

Asp Gly  Ala Ala Met Ala Val  Glu Pro Thr Gln Ile  Gln Leu Ser
    1940                 1945                 1950

Lys Arg  Trp Arg Glu Ile Glu  Ser Lys Phe Ala Gln  Phe Arg Arg
    1955                 1960                 1965

Leu Asn  Phe Ala Gln Ile His  Thr Val Arg Glu Glu  Thr Met Met
    1970                 1975                 1980

Val Met  Thr Glu Asp Met Pro  Leu Glu Ile Ser Tyr  Val Pro Ser
    1985                 1990                 1995

Thr Tyr  Leu Thr Glu Ile Thr  His Val Ser Gln Ala  Leu Leu Glu
    2000                 2005                 2010

Val Glu  Gln Leu Leu Asn Ala  Pro Asp Leu Cys Ala  Lys Asp Phe
    2015                 2020                 2025

Glu Asp  Leu Phe Lys Gln Glu  Glu Ser Leu Lys Asn  Ile Lys Asp
    2030                 2035                 2040

Ser Leu  Gln Gln Ser Ser Gly  Arg Ile Asp Ile Ile  His Ser Lys
    2045                 2050                 2055

Lys Thr  Ala Ala Leu Gln Ser  Ala Thr Pro Val Glu  Arg Val Lys
```

```
    2060                2065                2070

Leu Gln  Glu Ala Leu Ser Gln  Leu Asp Phe Gln Trp  Glu Lys Val
    2075                2080                2085

Asn Lys  Met Tyr Lys Asp Arg  Gln Gly Arg Phe Asp  Arg Ser Val
    2090                2095                2100

Glu Lys  Trp Arg Arg Phe His  Tyr Asp Ile Lys Ile  Phe Asn Gln
    2105                2110                2115

Trp Leu  Thr Glu Ala Glu Gln  Phe Leu Arg Lys Thr  Gln Ile Pro
    2120                2125                2130

Glu Asn  Trp Glu His Ala Lys  Tyr Lys Trp Tyr Leu  Lys Glu Leu
    2135                2140                2145

Gln Asp  Gly Ile Gly Gln Arg  Gln Thr Val Val Arg  Thr Leu Asn
    2150                2155                2160

Ala Thr  Gly Glu Glu Ile Ile  Gln Gln Ser Ser Lys  Thr Asp Ala
    2165                2170                2175

Ser Ile  Leu Gln Glu Lys Leu  Gly Ser Leu Asn Leu  Arg Trp Gln
    2180                2185                2190

Glu Val  Cys Lys Gln Leu Ser  Asp Arg Lys Lys Arg  Leu Glu Glu
    2195                2200                2205

Gln Lys  Asn Ile Leu Ser Glu  Phe Gln Arg Asp Leu  Asn Glu Phe
    2210                2215                2220

Val Leu  Trp Leu Glu Glu Ala  Asp Asn Ile Ala Ser  Ile Pro Leu
    2225                2230                2235

Glu Pro  Gly Lys Glu Gln Gln  Leu Lys Glu Lys Leu  Glu Gln Val
    2240                2245                2250

Lys Leu  Leu Val Glu Glu Leu  Pro Leu Arg Gln Gly  Ile Leu Lys
    2255                2260                2265

Gln Leu  Asn Glu Thr Gly Gly  Pro Val Leu Val Ser  Ala Pro Ile
    2270                2275                2280

Ser Pro  Glu Glu Gln Asp Lys  Leu Glu Asn Lys Leu  Lys Gln Thr
    2285                2290                2295

Asn Leu  Gln Trp Ile Lys Val  Ser Arg Ala Leu Pro  Glu Lys Gln
    2300                2305                2310

Gly Glu  Ile Glu Ala Gln Ile  Lys Asp Leu Gly Gln  Leu Glu Lys
    2315                2320                2325

Lys Leu  Glu Asp Leu Glu Glu  Gln Leu Asn His Leu  Leu Leu Trp
    2330                2335                2340

Leu Ser  Pro Ile Arg Asn Gln  Leu Glu Ile Tyr Asn  Gln Pro Asn
    2345                2350                2355

Gln Glu  Gly Pro Phe Asp Val  Gln Glu Thr Glu Ile  Ala Val Gln
    2360                2365                2370

Ala Lys  Gln Pro Asp Val Glu  Glu Ile Leu Ser Lys  Gly Gln His
    2375                2380                2385

Leu Tyr  Lys Glu Lys Pro Ala  Thr Gln Pro Val Lys  Arg Lys Leu
    2390                2395                2400

Glu Asp  Leu Ser Ser Glu Trp  Lys Ala Val Asn Arg  Leu Leu Gln
    2405                2410                2415

Glu Leu  Arg Ala Lys Gln Pro  Asp Leu Ala Pro Gly  Leu Thr Thr
    2420                2425                2430

Ile Gly  Ala Ser Pro Thr Gln  Thr Val Thr Leu Val  Thr Gln Pro
    2435                2440                2445

Val Val  Thr Lys Glu Thr Ala  Ile Ser Lys Leu Glu  Met Pro Ser
    2450                2455                2460
```

```
Ser Leu  Met Leu Glu Val Pro  Ala Leu Ala Asp Phe  Asn Arg Ala
    2465                 2470                 2475

Trp Thr  Glu Leu Thr Asp Trp  Leu Ser Leu Leu Asp  Gln Val Ile
    2480                 2485                 2490

Lys Ser  Gln Arg Val Met Val  Gly Asp Leu Glu Asp  Ile Asn Glu
    2495                 2500                 2505

Met Ile  Ile Lys Gln Lys Ala  Thr Met Gln Asp Leu  Glu Gln Arg
    2510                 2515                 2520

Arg Pro  Gln Leu Glu Glu Leu  Ile Thr Ala Ala Gln  Asn Leu Lys
    2525                 2530                 2535

Asn Lys  Thr Ser Asn Gln Glu  Ala Arg Thr Ile Ile  Thr Asp Arg
    2540                 2545                 2550

Ile Glu  Arg Ile Gln Asn Gln  Trp Asp Glu Val Gln  Glu His Leu
    2555                 2560                 2565

Gln Asn  Arg Arg Gln Gln Leu  Asn Glu Met Leu Lys  Asp Ser Thr
    2570                 2575                 2580

Gln Trp  Leu Glu Ala Lys Glu  Glu Ala Glu Gln Val  Leu Gly Gln
    2585                 2590                 2595

Ala Arg  Ala Lys Leu Glu Ser  Trp Lys Glu Gly Pro  Tyr Thr Val
    2600                 2605                 2610

Asp Ala  Ile Gln Lys Lys Ile  Thr Glu Thr Lys Gln  Leu Ala Lys
    2615                 2620                 2625

Asp Leu  Arg Gln Trp Gln Thr  Asn Val Asp Val Ala  Asn Asp Leu
    2630                 2635                 2640

Ala Leu  Lys Leu Leu Arg Asp  Tyr Ser Ala Asp Asp  Thr Arg Lys
    2645                 2650                 2655

Val His  Met Ile Thr Glu Asn  Ile Asn Ala Ser Trp  Arg Ser Ile
    2660                 2665                 2670

His Lys  Arg Val Ser Glu Arg  Glu Ala Ala Leu Glu  Glu Thr His
    2675                 2680                 2685

Arg Leu  Leu Gln Gln Phe Pro  Leu Asp Leu Glu Lys  Phe Leu Ala
    2690                 2695                 2700

Trp Leu  Thr Glu Ala Glu Thr  Thr Ala Asn Val Leu  Gln Asp Ala
    2705                 2710                 2715

Thr Arg  Lys Glu Arg Leu Leu  Glu Asp Ser Lys Gly  Val Lys Glu
    2720                 2725                 2730

Leu Met  Lys Gln Trp Gln Asp  Leu Gln Gly Glu Ile  Glu Ala His
    2735                 2740                 2745

Thr Asp  Val Tyr His Asn Leu  Asp Glu Asn Ser Gln  Lys Ile Leu
    2750                 2755                 2760

Arg Ser  Leu Glu Gly Ser Asp  Asp Ala Val Leu Leu  Gln Arg Arg
    2765                 2770                 2775

Leu Asp  Asn Met Asn Phe Lys  Trp Ser Glu Leu Arg  Lys Lys Ser
    2780                 2785                 2790

Leu Asn  Ile Arg Ser His Leu  Glu Ala Ser Ser Asp  Gln Trp Lys
    2795                 2800                 2805

Arg Leu  His Leu Ser Leu Gln  Glu Leu Leu Val Trp  Leu Gln Leu
    2810                 2815                 2820

Lys Asp  Asp Glu Leu Ser Arg  Gln Ala Pro Ile Gly  Gly Asp Phe
    2825                 2830                 2835

Pro Ala  Val Gln Lys Gln Asn  Asp Val His Arg Ala  Phe Lys Arg
    2840                 2845                 2850
```

-continued

```
Glu Leu  Lys Thr Lys Glu Pro  Val Ile Met Ser Thr  Leu Glu Thr
    2855                 2860                 2865

Val Arg  Ile Phe Leu Thr Glu  Gln Pro Leu Glu Gly  Leu Glu Lys
    2870                 2875                 2880

Leu Tyr  Gln Glu Pro Arg Glu  Leu Pro Pro Glu Glu  Arg Ala Gln
    2885                 2890                 2895

Asn Val  Thr Arg Leu Leu Arg  Lys Gln Ala Glu Glu  Val Asn Thr
    2900                 2905                 2910

Glu Trp  Glu Lys Leu Asn Leu  His Ser Ala Asp Trp  Gln Arg Lys
    2915                 2920                 2925

Ile Asp  Glu Thr Leu Glu Arg  Leu Gln Glu Leu Gln  Glu Ala Thr
    2930                 2935                 2940

Asp Glu  Leu Asp Leu Lys Leu  Arg Gln Ala Glu Val  Ile Lys Gly
    2945                 2950                 2955

Ser Trp  Gln Pro Val Gly Asp  Leu Leu Ile Asp Ser  Leu Gln Asp
    2960                 2965                 2970

His Leu  Glu Lys Val Lys Ala  Leu Arg Gly Glu Ile  Ala Pro Leu
    2975                 2980                 2985

Lys Glu  Asn Val Ser His Val  Asn Asp Leu Ala Arg  Gln Leu Thr
    2990                 2995                 3000

Thr Leu  Gly Ile Gln Leu Ser  Pro Tyr Asn Leu Ser  Thr Leu Glu
    3005                 3010                 3015

Asp Leu  Asn Thr Arg Trp Lys  Leu Leu Gln Val Ala  Val Glu Asp
    3020                 3025                 3030

Arg Val  Arg Gln Leu His Glu  Ala His Arg Asp Phe  Gly Pro Ala
    3035                 3040                 3045

Ser Gln  His Phe Leu Ser Thr  Ser Val Gln Gly Pro  Trp Glu Arg
    3050                 3055                 3060

Ala Ile  Ser Pro Asn Lys Val  Pro Tyr Tyr Ile Asn  His Glu Thr
    3065                 3070                 3075

Gln Thr  Thr Cys Trp Asp His  Pro Lys Met Thr Glu  Leu Tyr Gln
    3080                 3085                 3090

Ser Leu  Ala Asp Leu Asn Asn  Val Arg Phe Ser Ala  Tyr Arg Thr
    3095                 3100                 3105

Ala Met  Lys Leu Arg Arg Leu  Gln Lys Ala Leu Cys  Leu Asp Leu
    3110                 3115                 3120

Leu Ser  Leu Ser Ala Ala Cys  Asp Ala Leu Asp Gln  His Asn Leu
    3125                 3130                 3135

Lys Gln  Asn Asp Gln Pro Met  Asp Ile Leu Gln Ile  Ile Asn Cys
    3140                 3145                 3150

Leu Thr  Thr Ile Tyr Asp Arg  Leu Glu Gln Glu His  Asn Asn Leu
    3155                 3160                 3165

Val Asn  Val Pro Leu Cys Val  Asp Met Cys Leu Asn  Trp Leu Leu
    3170                 3175                 3180

Asn Val  Tyr Asp Thr Gly Arg  Thr Gly Arg Ile Arg  Val Leu Ser
    3185                 3190                 3195

Phe Lys  Thr Gly Ile Ile Ser  Leu Cys Lys Ala His  Leu Glu Asp
    3200                 3205                 3210

Lys Tyr  Arg Tyr Leu Phe Lys  Gln Val Ala Ser Ser  Thr Gly Phe
    3215                 3220                 3225

Cys Asp  Gln Arg Arg Leu Gly  Leu Leu Leu His Asp  Ser Ile Gln
    3230                 3235                 3240

Ile Pro  Arg Gln Leu Gly Glu  Val Ala Ser Phe Gly  Gly Ser Asn
```

```
    3245                3250                3255

Ile Glu  Pro Ser Val Arg Ser  Cys Phe Gln Phe Ala  Asn Asn Lys
    3260                3265                3270

Pro Glu  Ile Glu Ala Ala Leu  Phe Leu Asp Trp Met  Arg Leu Glu
    3275                3280                3285

Pro Gln  Ser Met Val Trp Leu  Pro Val Leu His Arg  Val Ala Ala
    3290                3295                3300

Ala Glu  Thr Ala Lys His Gln  Ala Lys Cys Asn Ile  Cys Lys Glu
    3305                3310                3315

Cys Pro  Ile Ile Gly Phe Arg  Tyr Arg Ser Leu Lys  His Phe Asn
    3320                3325                3330

Tyr Asp  Ile Cys Gln Ser Cys  Phe Phe Ser Gly Arg  Val Ala Lys
    3335                3340                3345

Gly His  Lys Met His Tyr Pro  Met Val Glu Tyr Cys  Thr Pro Thr
    3350                3355                3360

Thr Ser  Gly Glu Asp Val Arg  Asp Phe Ala Lys Val  Leu Lys Asn
    3365                3370                3375

Lys Phe  Arg Thr Lys Arg Tyr  Phe Ala Lys His Pro  Arg Met Gly
    3380                3385                3390

Tyr Leu  Pro Val Gln Thr Val  Leu Glu Gly Asp Asn  Met Glu Thr
    3395                3400                3405

Pro Val  Thr Leu Ile Asn Phe  Trp Pro Val Asp Ser  Ala Pro Ala
    3410                3415                3420

Ser Ser  Pro Gln Leu Ser His  Asp Asp Thr His Ser  Arg Ile Glu
    3425                3430                3435

His Tyr  Ala Ser Arg Leu Ala  Glu Met Glu Asn Ser  Asn Gly Ser
    3440                3445                3450

Tyr Leu  Asn Asp Ser Ile Ser  Pro Asn Glu Ser Ile  Asp Asp Glu
    3455                3460                3465

His Leu  Leu Ile Gln His Tyr  Cys Gln Ser Leu Asn  Gln Asp Ser
    3470                3475                3480

Pro Leu  Ser Gln Pro Arg Ser  Pro Ala Gln Ile Leu  Ile Ser Leu
    3485                3490                3495

Glu Ser  Glu Glu Arg Gly Glu  Leu Glu Arg Ile Leu  Ala Asp Leu
    3500                3505                3510

Glu Glu  Glu Asn Arg Asn Leu  Gln Ala Glu Tyr Asp  Arg Leu Lys
    3515                3520                3525

Gln Gln  His Glu His Lys Gly  Leu Ser Pro Leu Pro  Ser Pro Pro
    3530                3535                3540

Glu Met  Met Pro Thr Ser Pro  Gln Ser Pro Arg Asp  Ala Glu Leu
    3545                3550                3555

Ile Ala  Glu Ala Lys Leu Leu  Arg Gln His Lys Gly  Arg Leu Glu
    3560                3565                3570

Ala Arg  Met Gln Ile Leu Glu  Asp His Asn Lys Gln  Leu Glu Ser
    3575                3580                3585

Gln Leu  His Arg Leu Arg Gln  Leu Leu Glu Gln Pro  Gln Ala Glu
    3590                3595                3600

Ala Lys  Val Asn Gly Thr Thr  Val Ser Ser Pro Ser  Thr Ser Leu
    3605                3610                3615

Gln Arg  Ser Asp Ser Ser Gln  Pro Met Leu Leu Arg  Val Val Gly
    3620                3625                3630

Ser Gln  Thr Ser Asp Ser Met  Gly Glu Glu Asp Leu  Leu Ser Pro
    3635                3640                3645
```

Pro Gln Asp Thr Ser Thr Gly Leu Glu Glu Val Met Glu Gln Leu
3650 3655 3660

Asn Asn Ser Phe Pro Ser Ser Arg Gly Arg Asn Thr Pro Gly Lys
3665 3670 3675

Pro Met Arg Glu Asp Thr Met
3680 3685

<210> SEQ ID NO 7
<211> LENGTH: 13857
<212> TYPE: DNA
<213> ORGANISM: Mus musculus
<220> FEATURE:
<221> NAME/KEY: misc_feature
<223> OTHER INFORMATION: mRNA sequence of the murine dystrophin gene DMD transcript

<400> SEQUENCE: 7
atcagttact atgttgactc actcagtgtt gggctcactc acttgcccct tacaggactc 60
agctcttgaa ggcaatagcc tttatagaaa aaacgaatag gaagacttga agtgctattt 120 tttttttgt caaggctgct gaagtttatt ggcttctcat cgtacctaag cctcctggag 180
caataaaact gggagaaact tttaccaaga tttttatccc tgccttgata tatacttttt 240
cttccaaatg ctttggtggg aagaagtaga ggactgttat gaaagagaag atgttcaaaa 300
gaaaacattc acaaaatgga taaatgcaca attttctaag tttggaaagc aacacataga 360
caacctcttc agtgacctgc aggatggaaa acgcctccta gacctcttgg aaggccttac 420
agggcaaaaa ctgccaaaag aaaagggatc tacaagagtt catgccctga acaatgtcaa 480
caaggcactg cgggtcttac agaaaaataa tgttgattta gtgaatatag gaagcactga 540
catagtggat ggaaatcata aactcactct tggtttgatt tggaatataa tcctccactg 600
gcaggtcaaa aatgtgatga aaactatcat ggctggattg cagcaaacca acagtgaaaa 660
gattcttctg agctgggttc gacagtcaac acgtaattat ccacaggtta acgtcatcaa 720
cttcacctct agctggtccg acgggttggc tttgaatgct cttatccata gtcacaggcc 780
cgacctgttt gattggaata gtgtggtttc acagcactca gccacccaaa gactggaaca 840
tgccttcaac attgcaaaat gccagttagg catagaaaaa cttcttgatc ctgaagatgt 900
tgctaccact tatccagaca agaagtccat cttaatgtac atcacatcac tctttcaagt 960
tttgccacaa caagtgagca ttgaagccat tcaagaagtg gaaatgttgc ccaggacatc 1020
ttcaaaagta actagagaag aacattttca attacatcac cagatgcatt actctcaaca 1080
gatcacagtc agtctagcac agggctatga acaaacttct tcatctccta agcctcgatt 1140
caagagttat gccttcacac aggctgctta tgttgccacc tctgattcca cacagagccc 1200
ctatccttca cagcatttgg aagctcccag agacaagtca cttgacagtt cattgatgga 1260
gacggaagta aatctggata gttaccaaac tgctttagaa gaagtacttt catggcttct 1320
ttctgccgag gatacattgc gagcacaagg agagatttca aatgatgttg aagaagtgaa 1380
agaacagttt catgctcatg agggattcat gatggatctg acatctcatc aaggacttgt 1440
tggtaatgtt ctacagttag gaagtcaact agttggaaaa gggaaattat cagaagatga 1500
agaagctgaa gtgcaagaac aaatgaatct cctaaattca agatgggaat gtctcagggt 1560
agctagcatg gaaaaacaaa gcaaattaca caaagttcta atggatctcc agaatcagaa 1620
attaaaagaa ctagatgact ggttaacaaa aactgaagag agaactaaga aaatggagga 1680
agagcccttt ggacctgatc ttgaagatct aaaatgccaa gtacaacaac ataaggtgct 1740

```
tcaagaagat ctagaacagg agcaggtcag ggtcaactcg ctcactcaca tggtagtagt   1800
ggttgatgaa tccagcggtg atcatgcaac agctgctttg gaagaacaac ttaaggtact   1860
gggagatcga tgggcaaata tctgcagatg gactgaagac cgctggattg ttttacaaga   1920
tattcttcta aaatggcagc attttactga agaacagtgc ctttttagta catggctttc   1980
agaaaaagaa gatgcaatga agaacattca gacaagtggc tttaaagatc aaaatgaaat   2040
gatgtcaagt cttcacaaaa tatctacttt aaaaatagat ctagaaaaga aaaagccaac   2100
catggaaaaa ctaagttcac tcaatcaaga tctactttcg gcactgaaaa ataagtcagt   2160
gactcaaaag atggaaatct ggatggaaaa ctttgcacaa cgttgggaca atttaaccca   2220
aaaacttgaa aagagttcag cacaaatttc acaggctgtc accaccactc aaccatccct   2280
aacacagaca actgtaatgg aaacggtaac tatggtgacc acaagggaac aaatcatggt   2340
aaaacatgcc caagaggaac ttccaccacc acctcctcaa aagaagaggc agataactgt   2400
ggattctgaa ctcaggaaaa ggttggatgt cgatataact gaacttcaca gttggattac   2460
tcgttcagaa gctgtattac agagttctga atttgcagtc tatcgaaaag aaggcaacat   2520
ctcagacttg caagaaaaag tcaatgccat agcacgagaa aaagcagaga agttcagaaa   2580
actgcaagat gccagcagat cagctcaggc cctggtggaa cagatggcaa atgagggtgt   2640
taatgctgaa agtatcagac aagcttcaga acaactgaac agccggtgga cagaattctg   2700
ccaattgctg agtgagagag ttaactggct agagtatcaa accaacatca ttaccttta   2760
taatcagcta caacaattgg aacagatgac aactactgcc gaaaacttgt tgaaaaccca   2820
gtctaccacc ctatcagagc caacagcaat taaaagccag ttaaaaattt gtaaggatga   2880
agtcaacaga ttgtcagctc ttcagcctca aattgagcaa ttaaaaattc agagtctaca   2940
actgaaagaa aagggacagg ggccaatgtt tctggatgca gactttgtgg cctttactaa   3000
tcattttaac cacatctttg atggtgtgag ggccaaagag aaagagctac agacaatttt   3060
tgacacttta ccaccaatgc gctatcagga gacaatgagt agcatcagga cgtggatcca   3120
gcagtcagaa agcaaactct ctgtacctta tcttagtgtt actgaatatg aaataatgga   3180
ggagagactc gggaaattac aggctctgca aagttctttg aaagagcaac aaaatggctt   3240
caactatctg agtgacactg tgaaggagat ggccaagaaa gcaccttcag aaatatgcca   3300
gaaatatctg tcagaatttg aagagattga ggggcactgg aagaaacttt cctcccagtt   3360
ggtggaaagc tgccaaaagc tagaagaaca tatgaataaa cttcgaaaat ttcagaatca   3420
cataaaaacc ttacagaaat ggatggctga agttgatgtt ttcctgaaag aggaatggcc   3480
tgccctgggg gatgctgaaa tcctgaaaaa acagctcaaa caatgcagac ttttagttgg   3540
tgatattcaa acaattcagc ccagtttaaa tagtgttaat gaaggtgggc agaagataaa   3600
gagtgaagct gaacttgagt ttgcatccag actggagaca gaacttagag agcttaacac   3660
tcagtgggat cacatatgcc gccaggtcta caccagaaag gaagccttaa aggcaggttt   3720
ggataaaacc gtaagcctcc aaaaagatct atcagagatg catgagtgga tgacacaagc   3780
tgaagaagaa tatctagaga gagattttga atataaaact ccagatgaat tacagactgc   3840
tgttgaagaa atgaagagag ctaaagaaga ggcactacaa aaagaaacta aagtgaaact   3900
ccttactgag actgtaaata gtgtaatagc tcacgctcca ccctcagcac aagaggcctt   3960
aaaaaaggaa cttgaaactc tgaccaccaa ctaccaatgg ctgtgcacca ggctgaatgg   4020
aaaatgcaaa actttggaag aagtttgggc atgttggcat gagttattgt catatttaga   4080
```

-continued

```
gaaagcaaac aagtggctca atgaagtaga attgaaactt aaaaccatgg aaaatgttcc   4140
tgcaggacct gaggaaatca ctgaagtgct agaatctctt gaaaatctga tgcatcattc   4200
agaggagaac ccaaatcaga ttcgtctatt ggcacagact cttacagatg gaggagtcat   4260
ggatgaactg atcaatgagg agcttgagac gtttaattct cgttggaggg aactacatga   4320
agaggctgtg aggaaacaaa agttgcttga acagagtatc cagtctgccc aggaaattga   4380
aaagtccttg cacttaattc aggagtcgct tgaattcatt gacaagcagt tggcagctta   4440
tatcactgac aaggtggatg cagctcaaat gcctcaggaa gcccagaaaa tccaatcaga   4500
tttgacaagt catgagataa gtttagaaga aatgaagaaa cataaccagg ggaaggatgc   4560
caaccaaagg gttctttcac aaattgatgt tgcacagaaa aaattacaag atgtctccat   4620
gaaatttcga ttattccaaa aaccagccaa ttttgaacaa cgtctagagg aaagtaagat   4680
gattttagat gaagtcaaga tgcatttgcc tgcattggaa accaagagtg ttgaacagga   4740
agtaattcag tcacaactaa gtcattgtgt gaacttgtat aaaagcctga gtgaagtcaa   4800
gtctgaagtg gaaatggtga ttaaaaccgg acgtcaaatt gtacagaaaa agcagacaga   4860
aaatcccaaa gagcttgatg aacgagtaac agctttgaaa ttgcattaca atgagttggg   4920
tgcgaaggta acagagagaa agcaacagtt ggagaaatgc ttgaagttgt cccgtaagat   4980
gagaaaggaa atgaatgtct taacagaatg gctggcagca acagatacag aattgacgaa   5040
gagatcagca gttgaaggaa tgccaagtaa tttggattct gaagttgcct ggggaaaggc   5100
tactcaaaaa gagattgaga aacagaaggc tcacttgaag agtgttacag aattaggaga   5160
gtctttgaaa atggtgttgg gcaagaaaga aaccttggta gaagataaac tgagtcttct   5220
gaacagtaac tggatagctg tcacctccag agtagaagaa tggctaaatc ttttgttgga   5280
ataccagaaa cacatggaaa cctttgatca gaacatagaa caaatcacaa agtggatcat   5340
tcatgcagat gaacttttag atgagtctga aaagaagaaa ccacaacaaa aggaagacat   5400
tcttaagcgt ttaaaggctg aaatgaatga catgcgccca aaggtggact ccacacgtga   5460
ccaagcagca aaattgatgg caaaccgcgg tgaccactgc aggaaagtag tagagcccca   5520
aatctctgag ctcaaccgtc gatttgcagc tatttctcac agaattaaga ctggaaaggc   5580
ctccattcct ttgaaggaat tggagcagtt taactcagat atacaaaaat tgcttgaacc   5640
actggaggct gaaattcagc agggggtgaa tctgaaagag gaagacttca ataaagatat   5700
gagtgaagac aatgagggta ctgtaaatga attgttgcaa agaggagaca acttacaaca   5760
aagaatcaca gatgagagaa agcgagagga aataaagata aaacagcagc tgttacagac   5820
aaaacataat gctctcaagg atttgaggtc tcaaagaaga aaaaaggccc tagaaatttc   5880
tcaccagtgg tatcagtaca agaggcaggc tgatgatctc ctgaaatgct tggatgaaat   5940
tgaaaaaaaa ttagccagcc tacctgaacc cagagatgaa agaaaattaa aggaaattga   6000
tcgtgaattg cagaagaaga aagaggagct gaatgcagtg cgcaggcaag ctgagggctt   6060
gtctgagaat ggggccgcaa tggcagtgga gccaactcag atccagctca gcaagcgctg   6120
gcggcaaatt gagagcaatt ttgctcagtt tcgaagactc aactttgcac aaattcacac   6180
tctccatgaa gaaactatgg tagtgacgac tgaagatatg cctttggatg tttcttatgt   6240
gccttctact tatttgaccg agatcagtca tatcttacaa gctctttcag aagttgatca   6300
tcttctaaat actcctgaac tctgtgctaa agattttgaa gatcttttta agcaagagga   6360
gtctcttaag aatataaaag acaatttgca acaaatctca ggtcggattg atattattca   6420
caagaagaag acagcagcct tgcaaagtgc cacctccatg gaaaaggtga aagtacagga   6480
```

-continued

```
agccgtggca cagatggatt tccaggggga aaaacttcat agaatgtaca aggaacgaca   6540
agggcgattc gacagatcag ttgaaaaatg gcgacacttt cattatgata tgaaggtatt   6600
taatcaatgg ctgaatgaag ttgaacagtt tttcaaaaag acacaaaatc ctgaaaactg   6660
ggaacatgct aaatacaaat ggtatcttaa ggaactccag gatggcattg ggcagcgtca   6720
agctgttgtc agaacactga atgcaactgg ggaagaaata attcaacagt cttcaaaaac   6780
agatgtcaat attctacaag aaaaattagg aagcttgagt ctgcggtggc acgacatctg   6840
caaagagctg gcagaaagga gaaagaggat tgaagaacaa aagaatgtct tgtcagaatt   6900
tcaaagagat ttaaatgaat ttgttttgtg gctggaagaa gcagataaca ttgctattac   6960
tccacttgga gatgagcagc agctaaaaga acaacttgaa caagtcaagt tactggcaga   7020
agagttgccc ctgcgccagg gaattctaaa acaattaaat gaaacaggag gagcagtact   7080
tgtaagtgct cccataaggc cagaagagca agataaactt gaaaagaagc tcaaacagac   7140
aaatctccag tggataaagg tctccagagc tttacctgag aaacaaggag agcttgaggt   7200
tcacttaaaa gattttaggc agcttgaaga gcagctggat cacctgcttc tgtggctctc   7260
tcctattaga aaccagttgg aaatttataa ccaaccaagt caggcaggac cgtttgacat   7320
aaaggagatt gaagtaacag ttcacggtaa acaagcggat gtggaaaggc ttttgtcgaa   7380
agggcagcat ttgtataagg aaaaaccaag cactcagcca gtgaagagga agttagaaga   7440
tctgaggtct gagtgggagg ctgtaaacca tttacttcgg gagctgagga caaagcagcc   7500
tgaccgtgcc cctggactga gcactactgg agcctctgcc agtcagactg ttactctagt   7560
gacacaatct gtggttacta aggaaactgt catctccaaa ctagaaatgc catcttcttt   7620
gctgttggag gtacctgcac tggcagactt caaccgagct tggacagaac ttacagactg   7680
gctgtctctg cttgatcgag ttataaaatc acagagagtg atggtgggtg atctggaaga   7740
catcaatgaa atgatcatca aacagaaggc aacactgcaa gatttggaac agagacgccc   7800
ccaattggaa gaactcatta ctgctgccca gaatttgaaa aacaaaacca gcaatcaaga   7860
agctagaaca atcattactg atcgaattga aagaattcag attcagtggg atgaggttca   7920
agaacagctg cagaacagga gacaacagtt gaatgaaatg ttaaaggatt caacacaatg   7980
gctggaagct aaggaagaag ccgaacaggt cataggacag gtcagaggca agcttgactc   8040
atggaaagaa ggtcctcaca cagtagatgc aatccaaaag aagatcacag aaaccaagca   8100
gttggccaaa gacctccgtc aacggcagat aagtgtagac gtggcaaatg atttggcact   8160
gaaacttctt cgggactatt ctgctgatga taccagaaaa gtacacatga taacagagaa   8220
tatcaatact tcttggggaa acattcataa aagagtaagt gagcaagagg ctgctttgga   8280
agaaactcat agattactgc agcagttccc tctggacctg gagaagtttc tttcctggat   8340
tacggaagca gaaacaactg ccaatgtcct acaggacgct tcccgtaagg agaagctcct   8400
agaagactcc aggggagtca gagagctgat gaaaccatgg caagatctcc aaggagaaat   8460
tgaaactcac acagatatct atcacaatct tgatgaaaat ggccaaaaaa tcctgagatc   8520
cctggaaggt tcggatgaag cacccctgtt acaaagacgt ttggataaca tgaatttcaa   8580
gtggagtgaa cttcagaaaa agtctctcaa cattaggtcc catttggaag caagttctga   8640
ccagtggaag cgtttgcatc tttctcttca ggaacttctt gtttggctac agctgaaaga   8700
tgatgaactg agccgtcagg cacccatcgg tggtgatttc ccagcagttc agaagcagaa   8760
tgatatacat agggccttca agagggaatt gaaaactaaa gaacctgtaa tcatgagtac   8820
```

-continued

```
tctggagact gtgagaatat ttctgacaga gcagcctttg gaaggactag agaaactcta   8880
ccaggagccc agagaactgc ctcctgaaga aagagctcag aatgtcactc ggctcctacg   8940
aaagcaggct gaagaggtca acgctgaatg ggacaaattg aacctgcgct cagctgattg   9000
gcagagaaaa atagatgaag ctcttgaaag actccaggaa cttcaggaag ctgccgatga   9060
actggacctc aagttgcgcc aagctgaggt gatcaaggga tcctggcagc cagtgggga    9120
tctcctcatt gactctctgc aagatcacct tgaaaaagtc aaggcacttc ggggagaaat   9180
tgcacctctt aaagagaatg tcaatcgtgt caatgacctt gcacatcagc tgaccacact   9240
gggcattcag ctctcacctt ataacctcag cactttggaa gatctgaata ccagatggag   9300
gcttctacag gtggctgtgg aggaccgtgt cagacagctg catgaagccc acagggactt   9360
tggtcctgca tcccagcact tcctttccac ttcagttcag ggtccctggg agagagccat   9420
ctcaccaaac aaagtgccct actatatcaa ccacgagacc caaaccactt gttgggacca   9480
ccccaaaatg acagagctct accagtcttt agctgacctg aataatgtca ggttctccgc   9540
gtataggact gccatgaagc tcagaaggct ccagaaggcc ctttgcttgg atctcttgag   9600
cctgtcagct gcatgtgatg ccctggacca gcacaacctc aagcaaaatg accagcccat   9660
ggatatcctg cagataatta actgtttgac tacaatttat gatcgtctgg agcaagagca   9720
caacaatctg gtcaatgtcc ctctctgtgt ggatatgtgt ctcaactggc ttctcaatgt   9780
ttatgatacg ggacgaacag ggaggatccg tgtcctgtct tttaaaactg gcatcatttc   9840
tctgtgtaaa gcacacttgg aagacaagta cagatacctt ttcaagcaag tggcaagttc   9900
aactggcttt tgtgaccagc gtaggctggg tcttcttctg catgattcta ttcaaatccc   9960
aagacagttg ggtgaagttg cttcctttgg gggcagtaac attgagccga gtgtcaggag  10020
ctgcttccaa tttgccaata ataaacctga gattgaagct gctctcttcc ttgactggat  10080
gcgcctggaa ccccagtcta tggtgtggct gcccgtcttg cacagagtgg ctgctgctga  10140
aactgccaag catcaagcca agtgtaacat ctgtaaggag tgtccaatca ttggattcag  10200
gtacagaagc ctaaagcatt ttaattatga catctgccaa agttgctttt tttctggccg  10260
agttgcaaag ggccataaaa tgcactaccc catggtagag tattgcactc cgactacatc  10320
cggagaagat gttcgcgact tcgccaaggt actaaaaaac aaatttcgaa ccaaaaggta  10380
ttttgcgaag catccccgaa tgggctacct gccagtgcag actgtgttag agggggacaa  10440
catggaaact cccgttactc tgatcaactt ctggccagta gattctgcgc ctgcctcgtc  10500
cccccagctt tcacacgatg atactcattc acgcattgaa cattatgcta gcaggctagc  10560
agaaatggaa aacagcaatg gatcttatct aaatgatagc atctctccta atgagagcat  10620
agatgatgaa catttgttaa tccagcatta ctgccaaagt ttgaaccagg actcccccct  10680
gagccagcct cgtagtcctg cccagatctt gatttcctta gagagtgagg aaagagggga  10740
gctagagaga atcctagcag atcttgagga agaaaacagg aatctgcaag cagaatatga  10800
tcgcctgaag cagcagcatg agcataaagg cctgtctcca ctgccatctc ctcctgagat  10860
gatgcccacc tctcctcaga gtcccaggga tgctgagctc attgctgagg ctaagctact  10920
gcgccaacac aaaggacgcc tggaagccag gatgcaaatc ctggaagacc acaataaaca  10980
gctggagtct cagttacata gactgagaca gctcctggag cagccccagg ctgaagctaa  11040
ggtgaatggc accacggtgt cctctccttc cacctctctg cagaggtcag atagcagtca  11100
gcctatgctg ctccgagtgg ttggcagtca aacttcagaa tctatgggtg aggaagatct  11160
tctgagtcct ccccaggaca caagcacagg gttagaagaa gtgatggagc aactcaacaa  11220
```

-continued

```
ctccttccct agttcaagag gaagaaatgc ccccggaaag ccaatgagag aggacacaat  11280
gtaggaagcc ttttccacat ggcagatgat ttgggcagag cgatggagtc cttagtttca  11340
gtcatgacag atgaagaagg agcagaataa atgttttaca actcctgatt cccgcatggt  11400
ttttataata ttcgtacaac aaagaggatt agacagtaag agtttacaag aaataaaatc  11460
tatattttg tgaagggtag tggtactata ctgtagattt cagtagtttc taagtctgtt  11520
attgttttgt taacaatggc aggttttaca cgtctatgca attgtacaaa aaagttaaaa  11580
gaaaacatgt aaaatcttga tagctaaata acttgccatt tctttatatg gaacgcattt  11640
tgggttgttt aaaaatttat aacagttata aagaaagatt gtaaactaaa gtgtgcttta  11700
taaaaaaagt tgtttataaa aacccctaaa caaacacaca cgcacacaca cacacacaca  11760
cacacacaca cacacacgca cacatacatg cacgaaccca ccacacacac acacacacac  11820
acacacactg aggcagcaca ttgttttgca ttactttagc gtggtattca tatggaattc  11880
atgacgtttt tttattttct tgcatacgaa ccccaccaaa tgactgcttc atattgctct  11940
tttgagaatt gttgactgag tggggctggc tatgggcttt cattttatac atctatatgt  12000
ctacaagtat ataaatacta taggtatata gataaataga tatgaagtta cttcttcaaa  12060
tgttcttgcc acttcctaat ggaaattgct tctagtcatc tgggcttatc tgcttgggca  12120
agagtgaatt ttccctggag cccaaagcca ggagactacc gccacactaa aatattgtct  12180
agggctccag atgtttctag ttttaaactt tccactgaga gctagaggat tcattttttt  12240
caaggaacat gcgaatgaat acacaggact tactatcata gtaatttgtt ggctgatata  12300
ttcaacttcc tactgttggg ttatatttaa tgatgtttct gcaatagaac atcagatgac  12360
atttttaact cccagacagt aggaggaaga tggtaggagc taaaggttgc ggctcctcag  12420
tcaatttata tgaggggagc aacaactctg taaaagaatg gatgaatatt tacaactata  12480
catataaaca tctctataat tacaactaaa ttgttctgcc ctcttcataa actcaacctg  12540
aagtgggtgg ttttgttgtt gttgttgttg ttgttgttga tgatgatgat gaattttaga  12600
ttttagattt tttgggtttt tttttcttca ttgtgatgat tttttttttt aatgctgcaa  12660
gacttaggat tactgttaag aaagtaaccc aatcacattg tgaccctggt gaatatcagt  12720
ccagaagccc atgaactgca tttgtctcct ttgcattggt ttccctgcaa gtaactccac  12780
acaggattgt gggtgagaag gcacagtggt tggaaagttt tgagagcaaa agcgtctcca  12840
aactctctgg tctagttgac gggctgaaat gtctaaacaa atgcaagtca ttgaaccagg  12900
agaaaaagtg caacagaaag ctaaggactg ctaggaagag ctttactcct ctcatgccag  12960
tttcttcttc ttagcattta aagagcattc tctcaataga aatcactgtc ctatcatttt  13020
gcaaatctgt tacctctaac gtcaagtgta attaacttct agcgagtggg ttttgtccat  13080
tattaattgt aattaacatc aaacacagct tctcatgcta tttctacctc actttggttt  13140
tggggtgttt ctagtaattg tgcacaccta atttcacaac ttcaccactt gtctgttgtg  13200
tggacaccag tttccttttt tcatttataa tttccaaaag aaaacccaaa gctctaagat  13260
aacaaattga aatttggttc tggtcttgct ttctctctct ctctctcctt tatgtggcac  13320
tgggcatttt ctttatccaa ggatttgttt tcaccaagat ttaaaacaag ggttccttt  13380
cctactaaga agttttaagt ttcattctaa aatccaaggt agatagagtg catagttttg  13440
ttttaatctt ttcgttttat cttttagata ttagttctgg agtgaatcta tcaaaatatt  13500
tgaataaaaa ctgagagctt tattgctgat tttaagcata atttggacat catttcatgt  13560
```

```
tctttataac catcaagtat taaagtgtaa atcataatca gtgtaactga agcataatca  13620

tcacatggca tgtatcatca ttgtctccag gtactggact cttacttgag tatcataata  13680

gattgtgttt taacaccaac actgtaacat ttactaatta tttttttaaa cttcagtttt  13740

actgcatttt cacaacatat cagatttcac caaatatatg ccttactatt gtattatatt  13800

actgctttac tgtgtatctc aataaagcac gcagttatgt tacaaaaaaa taaaaaa     13857


<210> SEQ ID NO 8
<211> LENGTH: 213
<212> TYPE: DNA
<213> ORGANISM: Mus musculus
<220> FEATURE:
<221> NAME/KEY: misc_feature
<223> OTHER INFORMATION: Nucleotide sequence of the murine dystrophin
      gene DMD, exon 23

<400> SEQUENCE: 8

gctctgcaaa gttctttgaa agagcaacaa aatggcttca actatctgag tgacactgtg     60

aaggagatgg ccaagaaagc accttcagaa atatgccaga aatatctgtc agaatttgaa    120

gagattgagg ggcactggaa gaaactttcc tcccagttgg tggaaagctg ccaaaagcta    180

gaagaacata tgaataaact tcgaaaattt cag                                 213


<210> SEQ ID NO 9
<211> LENGTH: 213
<212> TYPE: DNA
<213> ORGANISM: Mus musculus
<220> FEATURE:
<221> NAME/KEY: misc_feature
<223> OTHER INFORMATION: Nucleotide sequence of the mutated dystrophin
      gene DMD from the mdx mouse, exon 23

<400> SEQUENCE: 9

gctctgcaaa gttctttgaa agagcaataa aatggcttca actatctgag tgacactgtg     60

aaggagatgg ccaagaaagc accttcagaa atatgccaga aatatctgtc agaatttgaa    120

gagattgagg ggcactggaa gaaactttcc tcccagttgg tggaaagctg ccaaaagcta    180

gaagaacata tgaataaact tcgaaaattt cag                                 213


<210> SEQ ID NO 10
<211> LENGTH: 114
<212> TYPE: DNA
<213> ORGANISM: Mus musculus
<220> FEATURE:
<221> NAME/KEY: misc_feature
<223> OTHER INFORMATION: Nucleotide sequence of the murine dystrophin
      gene DMD, exon 24

<400> SEQUENCE: 10

aatcacataa aaaccttaca gaaatggatg gctgaagttg atgttttcct gaaagaggaa     60

tggcctgccc tgggggatgc tgaaatcctg aaaaaacagc tcaaacaatg caga          114


<210> SEQ ID NO 11
<211> LENGTH: 913
<212> TYPE: DNA
<213> ORGANISM: Mus musculus
<220> FEATURE:
<221> NAME/KEY: misc_feature
<223> OTHER INFORMATION: Nucleotide sequence of the murine dystrophin
      gene DMD, intron 22

<400> SEQUENCE: 11

gtctgtggac atttgaatat cataaataac aaagaacatg tcttatcagt caagagatca     60
```

tattgatata ttaaacttaa ggtaataatg aaaaagtaaa gataataatg aaaaatcata 120
gattatgagt tggaaaaata aacagaacaa tttgaccaaa aacatgactt tttcttattt 180
ttttctatat attattttat aaatatacag acataaatag atatatattt ttaaattaaa 240
agtactgtat taaaggaaag gtataatttc atttcatatt tagtgacata agatatgaag 300
tatgattatt aaaattaaat cacattattt tattataatt actttatttt taattcctaa 360
tttctttaag cttaggtaaa atcaatggat ttatataatt agttagaatt taaatattaa 420
caaactataa cactatgatt aaatgcttga tattgagtag ttattttaat agcctaagtc 480
tggaaattaa atactagtaa gagaaacttc tgtgatgtga ggacatataa agactaattt 540
ttttgttgat tctaaaaatc ccatgttgta tacttattct ttttaaatct gaaaatatat 600
taatcatata ttgcctaaat gtcttaataa tgtttcactg taggtaagtt aaaatgtatc 660
acatatataa taaacatagt tattaatgca tagatattca gtaaaattat gacttctaaa 720
tttctgtcta aatataatat gccctgtaat ataatagaaa ttattcataa gaatacatat 780
atattgcttt atcagatatt ctactttgtt tagatctcta aattacataa acttttattt 840
accttcttct tgatatgaat gaaactcatc aaatatgcgt gttagtgtaa atgaacttct 900
atttaatttt gag 913

<210> SEQ ID NO 12
<211> LENGTH: 2607
<212> TYPE: DNA
<213> ORGANISM: Mus musculus
<220> FEATURE:
<221> NAME/KEY: misc_feature
<223> OTHER INFORMATION: Nucleotide sequence of the murine dystrophin
gene DMD, intron 23

<400> SEQUENCE: 12
gtaagccgag gtttggcctt taaactatat tttttcacat agcaattaat tggaaaatgt 60
gatgggaaac agatatttta cccagagtcc ttcaaagata ttgatgatat caaaagccaa 120
atctatttca aaggattgca acttgcctat ttttcctatg aaaacagtaa tgtgtcatac 180
cttcttggat tgtctgtata aatgaattga ttttttttca ccaactccaa gtatacttaa 240
cattttaaca taataattta aaatatcctt attccattat gttcattttt taagttgtag 300
atatgattta gctcacagca tacatatata cacatgtatt acatatgcat atattatata 360
tatggcagac atatgttttc actaccatat ttcacttttg aattatgaat atatgtttaa 420
tttctgccat atttccttcc ctacattgac ttctattaat ttagtatttc agtagttcta 480
acacattaat aataacctag actcaataca gtaatctaac aattatattt gtgcctgtaa 540
ttctaagtta gttaaattca taggttgtgt ttctcatagt tggccatttg tgaaatataa 600
taatatccga aaagaaagtt caaaaatgtc atgacttcat atagagttat tgaaacagtg 660
cccttacttt cattctggcc atgctagtga cttgatcatt cttgtatttt acagctaaaa 720
cactaccaaa agtgtcaaat ccatgatcta catgtttgac tgaggctagc agcacttatt 780
ccacccttat atgaagcctt taagagaaag tatatttgtt tgctattttt aacttcttga 840
aggaacatac aatctttgtt tcaagagctc atcctctttc atgctagtaa attttggtgg 900
cattgcatcc atgtctgact ctgaatctgt ttctgtctat cctgctccct aacactgtac 960
catcttcctt tttgaaaaaa aaatattgaa ttattttatt tatttacttt ccaaagttgc 1020
tcctgcctgt tcctccttct ccaagttctt cagtcccccc tgctccccac cgatgagagg 1080

-continued gaaaggtcct gaattcactg ggctccatgg gggtcctttt gcattttctt aaccttctta 1140
ataaaatagg ccttctagaa ttatatcata tacattgtga tatgacaaat gataaagtat 1200
attgttcaga gttttacctt gttcatattt gcaatgtccc cctgtcatgc tggatattct 1260
ttgattgggt atatttgcta acagattaag tatatttatc ttcgttaagc agtataactt 1320
attaagaaag aactctatta atatgagaaa taactaatga aacaccactc cacaggtgat 1380
ttcagccact ttatgaactg ctggaagcaa aaatgagatc tttgcaacat gaagcagttg 1440
ctcagttcat taaactgtgt tcaatatttc agccataaca tacattagag aatgatttat 1500
attgttcaaa catttggtgc tctatttttg catgacgtgg gattaaacac agcaccaaca 1560
atcaaacaat tgcaaagatg tattacaagt atttttttctt tttaaaacag gaaagtatac 1620
ttatatttcc attgtccaaa ccatcatgaa agggatagag attactgaca caaatttaga 1680
gaaaggattt gagtggagta agaattaaat gaaccaaaga agaattaatg tattcatcaa 1740
gaagtcatgg aggtgaaatt ggccttgaat gataccacta aggagagaat gttgagatcc 1800
ttatatttag tcaattgttt ttaaatctgt agttattaac cacattttaa tcatattgaa 1860
agggaaattt tctgtgatgc atgtattttc aatataaatt ttagaaaaga agacaattat 1920
aacttgattt tgtgaattac atggaactaa agaaatgaca gatttacatt tgaaaattga 1980
ctgaactaaa gtacataaat aaaagtcata cagaaaaatg tgggaggtgc ttgtccattt 2040
ataaaggaca aaaatgccat ttgttgccta atcattattt cttattggtc agaccaataa 2100
gaaatcaaga gctttgactt taaaggtaag aaaatcttac cttaaaatcc ccaactgaag 2160
ggactgttta aactgtcaac tgcagaaaac aagttatgga agttcaggtt tagggaaact 2220
ataaacacac cataacattg agtttatgtg catagtttgt tttatgtaca gtgagagtaa 2280
attgttagta ttatcatgag ttgttttgaa acttcaaatt tctctagagg ggtatgattt 2340
aatgttctca agaggaacat aataaaacca tatctggtat tagtttttat ttttaacaat 2400
agcagacttc atacaccaat gttcacagtg tagaccataa aatgcagtct tagtaaaaat 2460
attattctct ataaagctac aatgagacct ccctcaaaca tacattgttt tttttttttct 2520 aacttatgtt tggatatatc atcatgatga actatgttaa aaacaatcag agcttagtaa 2580
tactttcata ttgctttttt attccag 2607

<210> SEQ ID NO 13
<211> LENGTH: 150
<212> TYPE: DNA
<213> ORGANISM: Artificial Sequence
<220> FEATURE:
<223> OTHER INFORMATION: Antisense sequence AS1

<400> SEQUENCE: 13
cttcatatct tatgtcacta aatatgaaat gaaattatac ctttccttta atacagtact 60
tttaatttaa aaatatatat ctatttatgt ctgtatattt ataaaataat atatagaaaa 120
aaataagaaa aagtcatgtt tttggtcaaa 150

<210> SEQ ID NO 14
<211> LENGTH: 150
<212> TYPE: DNA
<213> ORGANISM: Artificial Sequence
<220> FEATURE:
<223> OTHER INFORMATION: Antisense sequence AS2

<400> SEQUENCE: 14 atatatttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata 150

<210> SEQ ID NO 15
<211> LENGTH: 150
<212> TYPE: DNA
<213> ORGANISM: Artificial Sequence
<220> FEATURE:
<223> OTHER INFORMATION: Antisense sequence AS3

<400> SEQUENCE: 15
aaatagaagt tcatttacac taacacgcat atttgatgag tttcattcat atcaagaaga 60
aggtaaataa aagtttatgt aatttagaga tctaaacaaa gtagaatatc tgataaagca 120
atatatatgt attcttatga ataatttcta 150

<210> SEQ ID NO 16
<211> LENGTH: 150
<212> TYPE: DNA
<213> ORGANISM: Artificial Sequence
<220> FEATURE:
<223> OTHER INFORMATION: Antisense sequence AS4

<400> SEQUENCE: 16
ttagttccat gtaattcaca aaatcaagtt ataattgtct tcttttctaa aatttatatt 60
gaaaatacat gcatcacaga aaatttccct ttcaatatga ttaaaatgtg gttaataact 120
acagatttaa aaacaattga ctaaatataa 150

<210> SEQ ID NO 17
<211> LENGTH: 150
<212> TYPE: DNA
<213> ORGANISM: Artificial Sequence
<220> FEATURE:
<223> OTHER INFORMATION: Antisense sequence AS5

<400> SEQUENCE: 17
cacataaact caatgttatg gtgtgtttat agtttcccta aacctgaact tccataactt 60
gttttctgca gttgacagtt taaacagtcc cttcagttgg ggattttaag gtaagatttt 120
cttaccttta aagtcaaagc tcttgatttc 150

<210> SEQ ID NO 18
<211> LENGTH: 150
<212> TYPE: DNA
<213> ORGANISM: Artificial Sequence
<220> FEATURE:
<223> OTHER INFORMATION: Antisense sequence AS6

<400> SEQUENCE: 18
tcatcatgat gatatatcca aacataagtt agaaaaaaaa aaacaatgta tgtttgaggg 60
aggtctcatt gtagctttat agagaataat atttttacta agactgcatt ttatggtcta 120
cactgtgaac attggtgtat gaagtctgct 150

<210> SEQ ID NO 19
<211> LENGTH: 150
<212> TYPE: DNA
<213> ORGANISM: Artificial Sequence
<220> FEATURE:
<223> OTHER INFORMATION: Antisense sequence AS7

<400> SEQUENCE: 19

-continued caagttgcaa tcctttgaaa tagatttggc ttttgatatc atcaatatct ttgaaggact 60
ctgggtaaaa tatctgtttc ccatcacatt ttccaattaa ttgctatgtg aaaaaatata 120
gtttaaaggc caaacctcgg cttacctgaa 150

<210> SEQ ID NO 20
<211> LENGTH: 150
<212> TYPE: DNA
<213> ORGANISM: Artificial Sequence
<220> FEATURE:
<223> OTHER INFORMATION: Antisense sequence AS8

<400> SEQUENCE: 20
ctacaactta aaaaatgaac ataatggaat aaggatattt taaattatta tgttaaaatg 60
ttaagtatac ttggagttgg tgaaaaaaaa tcaattcatt tatacagaca atccaagaag 120
gtatgacaca ttactgtttt cataggaaaa 150

<210> SEQ ID NO 21
<211> LENGTH: 306
<212> TYPE: DNA
<213> ORGANISM: Artificial Sequence
<220> FEATURE:
<223> OTHER INFORMATION: Antisense sequence 2XAS4

<400> SEQUENCE: 21
ttagttccat gtaattcaca aaatcaagtt ataattgtct tcttttctaa aatttatatt 60
gaaaatacat gcatcacaga aaatttccct ttcaatatga ttaaaatgtg gttaataact 120
acagatttaa aaacaattga ctaaatataa gaattcttag ttccatgtaa ttcacaaaat 180
caagttataa ttgtcttctt ttctaaaatt tatattgaaa atacatgcat cacagaaaat 240
ttccctttca atatgattaa aatgtggtta ataactacag atttaaaaac aattgactaa 300
atataa 306

<210> SEQ ID NO 22
<211> LENGTH: 2250
<212> TYPE: DNA
<213> ORGANISM: Artificial Sequence
<220> FEATURE:
<223> OTHER INFORMATION: Nucleotide sequence located in the 5'-half of
the nucleotide sequence of intron 23

<400> SEQUENCE: 22
gtaagccgag gtttggcctt taaactatat tttttcacat agcaattaat tggaaaatgt 60
gatgggaaac agatatttta cccagagtcc ttcaaagata ttgatgatat caaaagccaa 120
atctatttca aaggattgca acttgcctat ttttcctatg aaaacagtaa tgtgtcatac 180
cttcttggat tgtctgtata aatgaattga ttttttttca ccaactccaa gtatacttaa 240
cattttaaca taataattta aaatatcctt attccattat gttcattttt taagttgtag 300
atatgattta gctcacagca tacatatata cacatgtatt acatatgcat atattatata 360
tatggcagac atatgttttc actaccatat ttcacttttg aattatgaat atatgtttaa 420
tttctgccat atttccttcc ctacattgac ttctattaat ttagtatttc agtagttcta 480
acacattaat aataacctag actcaataca gtaatctaac aattatattt gtgcctgtaa 540
ttctaagtta gttaaattca taggttgtgt ttctcatagt tggccatttg tgaaatataa 600
taatatccga aaagaaagtt caaaaatgtc atgacttcat atagagttat tgaaacagtg 660
cccttacttt cattctggcc atgctagtga cttgatcatt cttgtatttt acagctaaaa 720

-continued cactaccaaa agtgtcaaat ccatgatcta catgtttgac tgaggctagc agcacttatt 780
ccacccttat atgaagcctt taagagaaag tatatttgtt tgctattttt aacttcttga 840
aggaacatac aatctttgtt tcaagagctc atcctctttc atgctagtaa attttggtgg 900
cattgcatcc atgtctgact ctgaatctgt ttctgtctat cctgctccct aacactgtac 960
catcttcctt tttgaaaaaa aaatattgaa ttattttatt tatttacttt ccaaagttgc 1020
tcctgcctgt tcctccttct ccaagttctt cagtcccccc tgctccccac cgatgagagg 1080
gaaaggtcct gaattcactg ggctccatgg gggtcctttt gcattttctt aaccttctta 1140
ataaaatagg ccttctagaa ttatatcata tacattgtga tatgacaaat gataaagtat 1200
attgttcaga gttttacctt gttcatattt gcaatgtccc cctgtcatgc tggatattct 1260
ttgattgggt atatttgcta acagattaag tatatttatc ttcgttaagc agtataactt 1320
attaagaaag aactctatta atatgagaaa taactaatga aacaccactc cacaggtgat 1380
ttcagccact ttatgaactg ctggaagcaa aaatgagatc tttgcaacat gaagcagttg 1440
ctcagttcat taaactgtgt tcaatatttc agccataaca tacattagag aatgatttat 1500
attgttcaaa catttggtgc tctatttttg catgacgtgg gattaaacac agcaccaaca 1560
atcaaacaat tgcaaagatg tattacaagt atttttcttt tttaaaacag gaaagtatac 1620
ttatatttcc attgtccaaa ccatcatgaa agggatagag attactgaca caaatttaga 1680
gaaaggattt gagtggagta agaattaaat gaaccaaaga agaattaatg tattcatcaa 1740
gaagtcatgg aggtgaaatt ggccttgaat gataccacta aggagagaat gttgagatcc 1800
ttatatttag tcaattgttt ttaaatctgt agttattaac cacattttaa tcatattgaa 1860
agggaaattt tctgtgatgc atgtattttc aatataaatt ttagaaaaga agacaattat 1920
aacttgattt tgtgaattac atggaactaa agaaatgaca gatttacatt tgaaaattga 1980
ctgaactaaa gtacataaat aaaagtcata cagaaaaatg tgggaggtgc ttgtccattt 2040
ataaaggaca aaaatgccat ttgttgccta atcattattt cttattggtc agaccaataa 2100
gaaatcaaga gctttgactt taaaggtaag aaaatcttac cttaaaatcc ccaactgaag 2160
ggactgttta aactgtcaac tgcagaaaac aagttatgga agttcaggtt tagggaaact 2220
ataaacacac cataacattg agtttatgtg 2250

<210> SEQ ID NO 23
<211> LENGTH: 34
<212> TYPE: DNA
<213> ORGANISM: Artificial Sequence
<220> FEATURE:
<223> OTHER INFORMATION: Spacer 1 (3' end)

<400> SEQUENCE: 23
acagctcttt ctttccatgg gttggcctga attc 34

<210> SEQ ID NO 24
<211> LENGTH: 42
<212> TYPE: DNA
<213> ORGANISM: Artificial Sequence
<220> FEATURE:
<223> OTHER INFORMATION: Spacer 2 (5'-end)

<400> SEQUENCE: 24
ctcgagagat ctccgcggaa cattattata acgttgctcg aa 42

<210> SEQ ID NO 25
<211> LENGTH: 7

-continued

<212> TYPE: DNA
<213> ORGANISM: Artificial Sequence
<220> FEATURE:
<223> OTHER INFORMATION: Conserved yeast branch point sequence

<400> SEQUENCE: 25 tactaac 7

<210> SEQ ID NO 26
<211> LENGTH: 30
<212> TYPE: DNA
<213> ORGANISM: Artificial Sequence
<220> FEATURE:
<223> OTHER INFORMATION: Intronic Splice Enhancer (ISE) sequence

<400> SEQUENCE: 26
ggctgaggga aggactgtcc tggggactgg 30

<210> SEQ ID NO 27
<211> LENGTH: 24
<212> TYPE: DNA
<213> ORGANISM: Artificial Sequence
<220> FEATURE:
<223> OTHER INFORMATION: Downstream Intronic Splice Enhancer (DISE) sequence

<400> SEQUENCE: 27
ctctttcttt ccatgggttg gcct 24

<210> SEQ ID NO 28
<211> LENGTH: 20
<212> TYPE: DNA
<213> ORGANISM: Artificial Sequence
<220> FEATURE:
<223> OTHER INFORMATION: Polypyrimidine tract sequence

<400> SEQUENCE: 28
tctcttcttt ttttttttcc 20

<210> SEQ ID NO 29
<211> LENGTH: 9
<212> TYPE: DNA
<213> ORGANISM: Artificial Sequence
<220> FEATURE:
<223> OTHER INFORMATION: Canonical 3' acceptor splice site

<400> SEQUENCE: 29 ggaaaacag 9

<210> SEQ ID NO 30
<211> LENGTH: 6
<212> TYPE: DNA
<213> ORGANISM: Artificial Sequence
<220> FEATURE:
<223> OTHER INFORMATION: 5' donor splice site

<400> SEQUENCE: 30 gtaaga 6

<210> SEQ ID NO 31
<211> LENGTH: 41
<212> TYPE: DNA
<213> ORGANISM: Artificial Sequence
<220> FEATURE:
<223> OTHER INFORMATION: 3' splice region of the Pre-Trans-Splicing molecule gene

<400> SEQUENCE: 31
tactaactga tatctcttct tttttttttt ccggaaaaca g 41

<210> SEQ ID NO 32
<211> LENGTH: 19
<212> TYPE: DNA
<213> ORGANISM: Artificial Sequence
<220> FEATURE:
<223> OTHER INFORMATION: Forward primer for E23

<400> SEQUENCE: 32
agatggccaa gaaagcacc 19

<210> SEQ ID NO 33
<211> LENGTH: 19
<212> TYPE: DNA
<213> ORGANISM: Artificial Sequence
<220> FEATURE:
<223> OTHER INFORMATION: Reverse primer for E23

<400> SEQUENCE: 33
ctttccacca actgggagg 19

<210> SEQ ID NO 34
<211> LENGTH: 23
<212> TYPE: DNA
<213> ORGANISM: Artificial Sequence
<220> FEATURE:
<223> OTHER INFORMATION: Forward primer for E24

<400> SEQUENCE: 34
tgaaaaaaca gctcaaacaa tgc 23

<210> SEQ ID NO 35
<211> LENGTH: 19
<212> TYPE: DNA
<213> ORGANISM: Artificial Sequence
<220> FEATURE:
<223> OTHER INFORMATION: Reverse primer for E24

<400> SEQUENCE: 35
agcatccccc agggcaggc 19

<210> SEQ ID NO 36
<211> LENGTH: 21
<212> TYPE: DNA
<213> ORGANISM: Artificial Sequence
<220> FEATURE:
<223> OTHER INFORMATION: Forward primer E22-F

<400> SEQUENCE: 36
gacactttac caccaatgcg c 21

<210> SEQ ID NO 37
<211> LENGTH: 20
<212> TYPE: DNA
<213> ORGANISM: Artificial Sequence
<220> FEATURE:
<223> OTHER INFORMATION: Reverse primer pSMD2-R1

<400> SEQUENCE: 37
ctttctgata ggcagcctgc 20

<210> SEQ ID NO 38
<211> LENGTH: 20

<212> TYPE: DNA
<213> ORGANISM: Artificial Sequence
<220> FEATURE:
<223> OTHER INFORMATION: Primer pSMD2-R5

<400> SEQUENCE: 38
ctcaccctga agttctcagg 20

<210> SEQ ID NO 39
<211> LENGTH: 3996
<212> TYPE: DNA
<213> ORGANISM: Artificial Sequence
<220> FEATURE:
<223> OTHER INFORMATION: The murine DMD minigene target comprising exons E22, E23, and E24

<400> SEQUENCE: 39
tttttgacac tttaccacca atgcgctatc aggagacaat gagtagcatc aggacgtgga 60
tccagcagtc agaaagcaaa ctctctgtac cttatcttag tgttactgaa tatgaaataa 120
tggaggagag actcgggaaa ttacaggtct gtggacattt gaatatcata aataacaaag 180
aacatgtctt atcagtcaag agatcatatt gatatattaa acttaaggta ataatgaaaa 240
agtaaagata ataatgaaaa atcatagatt atgagttgga aaaataaaca gaacaatttg 300
accaaaaaca tgactttttc ttattttttt ctatatatta ttttataaat atacagacat 360
aaatagatat atatttttaa attaaaagta ctgtattaaa ggaaaggtat aatttcattt 420
catatttagt gacataagat atgaagtatg attattaaaa ttaaatcaca ttattttatt 480
ataattactt tatttttaat tcctaatttc tttaagctta ggtaaaatca atggatttat 540
ataattagtt agaatttaaa tattaacaaa ctataacact atgattaaat gcttgatatt 600
gagtagttat tttaatagcc taagtctgga aattaaatac tagtaagaga aacttctgtg 660
atgtgaggac atataaagac taattttttt gttgattcta aaaatcccat gttgtatact 720
tattcttttt aaatctgaaa atatattaat catatattgc ctaaatgtct taataatgtt 780
tcactgtagg taagttaaaa tgtatcacat atataataaa catagttatt aatgcataga 840
tattcagtaa aattatgact tctaaatttc tgtctaaata taatatgccc tgtaatataa 900
tagaaattat tcataagaat acatatatat tgctttatca gatattctac tttgtttaga 960
tctctaaatt acataaactt ttatttacct tcttcttgat atgaatgaaa ctcatcaaat 1020
atgcgtgtta gtgtaaatga acttctattt aattttgagg ctctgcaaag ttctttgaaa 1080
gagcaataaa atggcttcaa ctatctgagt gacactgtga aggagatggc caagaaagca 1140
ccttcagaaa tatgccagaa atatctgtca gaatttgaag agattgaggg gcactggaag 1200
aaactttcct cccagttggt ggaaagctgc caaaagctag aagaacatat gaataaactt 1260
cgaaaatttc aggtaagccg aggtttggcc tttaaactat attttttcac atagcaatta 1320
attggaaaat gtgatgggaa acagatattt tacccagagt ccttcaaaga tattgatgat 1380
atcaaaagcc aaatctattt caaaggattg caacttgcct atttttccta tgaaaacagt 1440
aatgtgtcat accttcttgg attgtctgta taaatgaatt gatttttttt caccaactcc 1500
aagtatactt aacattttaa cataataatt taaaatatcc ttattccatt atgttcattt 1560
tttaagttgt agatatgatt tagctcacag catacatata tacacatgta ttacatatgc 1620
atatattata tatatggcag acatatgttt tcactaccat atttcacttt tgaattatga 1680
atatatgttt aatttctgcc atatttcctt ccctacattg acttctatta atttagtatt 1740
tcagtagttc taacacatta ataataacct agactcaata cagtaatcta acaattatat 1800

```
ttgtgcctgt aattctaagt tagttaaatt cataggttgt gtttctcata gttggccatt   1860
tgtgaaatat aataatatcc gaaaagaaag ttcaaaaatg tcatgacttc atatagagtt   1920
attgaaacag tgcccttact ttcattctgg ccatgctagt gacttgatca ttcttgtatt   1980
ttacagctaa aacactacca aaagtgtcaa atccatgatc tacatgtttg actgaggcta   2040
gcagcactta ttccaccctt atatgaagcc tttaagagaa agtatatttg tttgctattt   2100
ttaacttctt gaaggaacat acaatctttg tttcaagagc tcatcctctt tcatgctagt   2160
aaattttggt ggcattgcat ccatgtctga ctctgaatct gtttctgtct atcctgctcc   2220
ctaacactgt accatcttcc tttttgaaaa aaaaatattg aattatttta tttatttact   2280
ttccaaagtt gctcctgcct gttcctcctt ctccaagttc ttcagtcccc cctgctcccc   2340
accgatgaga gggaaaggtc ctgaattcac tgggctccat gggggtcctt ttgcattttc   2400
ttaaccttct taataaaata ggccttctag aattatatca tatacattgt gatatgacaa   2460
atgataaagt atattgttca gagttttacc ttgttcatat ttgcaatgtc cccctgtcat   2520
gctggatatt ctttgattgg gtatatttgc taacagatta agtatattta tcttcgttaa   2580
gcagtataac ttattaagaa agaactctat taatatgaga aataactaat gaaacaccac   2640
tccacaggtg atttcagcca ctttatgaac tgctggaagc aaaaatgaga tctttgcaac   2700
atgaagcagt tgctcagttc attaaactgt gttcaatatt tcagccataa catacattag   2760
agaatgattt atattgttca aacatttggt gctctatttt tgcatgacgt gggattaaac   2820
acagcaccaa caatcaaaca attgcaaaga tgtattacaa gtatttttttc tttttaaaac   2880
aggaaagtat acttatattt ccattgtcca aaccatcatg aaagggatag agattactga   2940
cacaaattta gagaaaggat ttgagtggag taagaattaa atgaaccaaa gaagaattaa   3000
tgtattcatc aagaagtcat ggaggtgaaa ttggccttga atgataccac taaggagaga   3060
atgttgagat ccttatattt agtcaattgt ttttaaatct gtagttatta accacatttt   3120
aatcatattg aaagggaaat ttctgtgat gcatgtattt tcaatataaa ttttagaaaa   3180
gaagacaatt ataacttgat tttgtgaatt acatggaact aaagaaatga cagatttaca   3240
tttgaaaatt gactgaacta aagtacataa ataaaagtca tacagaaaaa tgtgggaggt   3300
gcttgtccat ttataaagga caaaaatgcc atttgttgcc taatcattat ttcttattgg   3360
tcagaccaat aagaaatcaa gagctttgac tttaaaggta agaaaatctt accttaaaat   3420
ccccaactga agggactgtt taaactgtca actgcagaaa acaagttatg gaagttcagg   3480
tttagggaaa ctataaacac accataacat tgagtttatg tgcatagttt gttttatgta   3540
cagtgagagt aaattgttag tattatcatg agttgttttg aaacttcaaa tttctctaga   3600
ggggtatgat ttaatgttct caagaggaac ataataaaac catatctggt attagttttt   3660
atttttaaca atagcagact tcatacacca atgttcacag tgtagaccat aaaatgcagt   3720
cttagtaaaa atattattct ctataaagct acaatgagac ctccctcaaa catacattgt   3780
ttttttttt ctaacttatg tttggatata tcatcatgat gaactatgtt aaaaacaatc   3840
agagcttagt aatactttca tattgctttt ttattccaga atcacataaa aaccttacag   3900
aaatggatgg ctgaagttga tgttttcctg aaagaggaat ggcctgccct gggggatgct   3960
gaaatcctga aaaaacagct caaacaatgc agataa                             3996
```

<210> SEQ ID NO 40
<211> LENGTH: 347
<212> TYPE: DNA

<213> ORGANISM: Artificial Sequence
<220> FEATURE:
<223> OTHER INFORMATION: TS molecules AS1-E24

<400> SEQUENCE: 40
cttcatatct tatgtcacta aatatgaaat gaaattatac ctttccttta atacagtact 60
tttaatttaa aaatatatat ctatttatgt ctgtatattt ataaaataat atatagaaaa 120
aaataagaaa aagtcatgtt tttggtcaaa ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcaga 347

<210> SEQ ID NO 41
<211> LENGTH: 347
<212> TYPE: DNA
<213> ORGANISM: Artificial Sequence
<220> FEATURE:
<223> OTHER INFORMATION: TS molecule AS2-E24

<400> SEQUENCE: 41
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcaga 347

<210> SEQ ID NO 42
<211> LENGTH: 347
<212> TYPE: DNA
<213> ORGANISM: Artificial Sequence
<220> FEATURE:
<223> OTHER INFORMATION: TS molecule AS3-E24

<400> SEQUENCE: 42
aaatagaagt tcatttacac taacacgcat atttgatgag tttcattcat atcaagaaga 60
aggtaaataa aagtttatgt aatttagaga tctaaacaaa gtagaatatc tgataaagca 120
atatatatgt attcttatga ataatttcta ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcaga 347

<210> SEQ ID NO 43
<211> LENGTH: 185
<212> TYPE: DNA
<213> ORGANISM: Artificial Sequence
<220> FEATURE:
<223> OTHER INFORMATION: Trans-Splicing molecule with no binding domain
(AS-)

<400> SEQUENCE: 43
ccgcggaaca ttattataac gttgctcgaa tactaactga tatctcttct tttttttttt 60
ccggaaaaca gaatcacata aaaaccttac agaaatggat ggctgaagtt gatgttttcc 120
tgaaagagga atggcctgcc ctgggggatg ctgaaatcct gaaaaaacag ctcaaacaat 180

```
gcaga                                                                    185

<210> SEQ ID NO 44
<211> LENGTH: 515
<212> TYPE: DNA
<213> ORGANISM: Artificial Sequence
<220> FEATURE:
<223> OTHER INFORMATION: TS molecule AS1-E24-AS4

<400> SEQUENCE: 44

cttcatatct tatgtcacta aatatgaaat gaaattatac ctttccttta atacagtact    60

tttaatttaa aaatatatat ctatttatgt ctgtatattt ataaaataat atatagaaaa   120

aaataagaaa aagtcatgtt tttggtcaaa ctcgagagat ctccgcggaa cattattata   180

acgttgctcg aatactaact gatatctctt cttttttttt ttccggaaaa cagaatcaca   240

taaaaacctt acagaaatgg atggctgaag ttgatgtttt cctgaaagag gaatggcctg   300

ccctggggga tgctgaaatc ctgaaaaaac agctcaaaca atgcagagta agaagatctg   360

aattcttagt tccatgtaat tcacaaaatc aagttataat tgtcttcttt tctaaaattt   420

atattgaaaa tacatgcatc acagaaaatt tccctttcaa tatgattaaa atgtggttaa   480

taactacaga tttaaaaaca attgactaaa tataa                              515

<210> SEQ ID NO 45
<211> LENGTH: 515
<212> TYPE: DNA
<213> ORGANISM: Artificial Sequence
<220> FEATURE:
<223> OTHER INFORMATION: TS molecule AS1-E24-AS5

<400> SEQUENCE: 45

cttcatatct tatgtcacta aatatgaaat gaaattatac ctttccttta atacagtact    60

tttaatttaa aaatatatat ctatttatgt ctgtatattt ataaaataat atatagaaaa   120

aaataagaaa aagtcatgtt tttggtcaaa ctcgagagat ctccgcggaa cattattata   180

acgttgctcg aatactaact gatatctctt cttttttttt ttccggaaaa cagaatcaca   240

taaaaacctt acagaaatgg atggctgaag ttgatgtttt cctgaaagag gaatggcctg   300

ccctggggga tgctgaaatc ctgaaaaaac agctcaaaca atgcagagta agaagatctg   360

aattccacat aaactcaatg ttatggtgtg tttatagttt ccctaaacct gaacttccat   420

aacttgtttt ctgcagttga cagtttaaac agtcccttca gttggggatt ttaaggtaag   480

attttcttac ctttaaagtc aaagctcttg atttc                              515

<210> SEQ ID NO 46
<211> LENGTH: 515
<212> TYPE: DNA
<213> ORGANISM: Artificial Sequence
<220> FEATURE:
<223> OTHER INFORMATION: TS molecule AS1-E24-AS6

<400> SEQUENCE: 46

cttcatatct tatgtcacta aatatgaaat gaaattatac ctttccttta atacagtact    60

tttaatttaa aaatatatat ctatttatgt ctgtatattt ataaaataat atatagaaaa   120

aaataagaaa aagtcatgtt tttggtcaaa ctcgagagat ctccgcggaa cattattata   180

acgttgctcg aatactaact gatatctctt cttttttttt ttccggaaaa cagaatcaca   240

taaaaacctt acagaaatgg atggctgaag ttgatgtttt cctgaaagag gaatggcctg   300

ccctggggga tgctgaaatc ctgaaaaaac agctcaaaca atgcagagta agaagatctg   360
```

aattctcatc atgatgatat atccaaacat aagttagaaa aaaaaaaaca atgtatgttt 420
gagggaggtc tcattgtagc tttatagaga ataatatttt tactaagact gcattttatg 480
gtctacactg tgaacattgg tgtatgaagt ctgct 515

<210> SEQ ID NO 47
<211> LENGTH: 515
<212> TYPE: DNA
<213> ORGANISM: Artificial Sequence
<220> FEATURE:
<223> OTHER INFORMATION: TS molecule AS1-E24-AS7

<400> SEQUENCE: 47
cttcatatct tatgtcacta aatatgaaat gaaattatac ctttccttta atacagtact 60
tttaatttaa aaatatatat ctatttatgt ctgtatattt ataaaataat atatagaaaa 120
aaataagaaa aagtcatgtt tttggtcaaa ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaagatctg 360
aattccaagt tgcaatcctt tgaaatagat ttggcttttg atatcatcaa tatctttgaa 420
ggactctggg taaaatatct gtttcccatc acattttcca attaattgct atgtgaaaaa 480
atatagttta aaggccaaac ctcggcttac ctgaa 515

<210> SEQ ID NO 48
<211> LENGTH: 515
<212> TYPE: DNA
<213> ORGANISM: Artificial Sequence
<220> FEATURE:
<223> OTHER INFORMATION: TS molecule AS2-E24-AS4

<400> SEQUENCE: 48
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaagatctg 360
aattcttagt tccatgtaat tcacaaaatc aagttataat tgtcttcttt tctaaaattt 420
atattgaaaa tacatgcatc acagaaaatt tccctttcaa tatgattaaa atgtggttaa 480
taactacaga tttaaaaaca attgactaaa tataa 515

<210> SEQ ID NO 49
<211> LENGTH: 515
<212> TYPE: DNA
<213> ORGANISM: Artificial Sequence
<220> FEATURE:
<223> OTHER INFORMATION: TS molecule AS2-E24-AS5

<400> SEQUENCE: 49
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaagatctg 360
aattccacat aaactcaatg ttatggtgtg tttatagttt ccctaaacct gaacttccat 420
aacttgtttt ctgcagttga cagtttaaac agtcccttca gttggggatt ttaaggtaag 480 atttcttac ctttaaagtc aaagctcttg atttc 515

<210> SEQ ID NO 50
<211> LENGTH: 515
<212> TYPE: DNA
<213> ORGANISM: Artificial Sequence
<220> FEATURE:
<223> OTHER INFORMATION: TS molecule AS2-E24-AS6

<400> SEQUENCE: 50 atatatttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaagatctg 360
aattctcatc atgatgatat atccaaacat aagttagaaa aaaaaaaaca atgtatgttt 420
gagggaggtc tcattgtagc tttatagaga ataatatttt tactaagact gcattttatg 480
gtctacactg tgaacattgg tgtatgaagt ctgct 515

<210> SEQ ID NO 51
<211> LENGTH: 515
<212> TYPE: DNA
<213> ORGANISM: Artificial Sequence
<220> FEATURE:
<223> OTHER INFORMATION: TS molecule AS2-E24-AS7

<400> SEQUENCE: 51
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaagatctg 360
aattccaagt tgcaatcctt tgaaatagat ttggcttttg atatcatcaa tatctttgaa 420
ggactctggg taaaatatct gtttcccatc acattttcca attaattgct atgtgaaaaa 480
atatagttta aaggccaaac ctcggcttac ctgaa 515

<210> SEQ ID NO 52
<211> LENGTH: 515
<212> TYPE: DNA
<213> ORGANISM: Artificial Sequence
<220> FEATURE:
<223> OTHER INFORMATION: TS molecule AS2-E24-AS8

<400> SEQUENCE: 52
atatattttc agatttaaaa agaataagta tacaacatgg gatttttaga atcaacaaaa 60

```
aaattagtct ttatatgtcc tcacatcaca gaagtttctc ttactagtat ttaatttcca    120

gacttaggct attaaaataa ctactcaata ctcgagagat ctccgcggaa cattattata    180

acgttgctcg aatactaact gatatctctt cttttttttt ttccggaaaa cagaatcaca    240

taaaaacctt acagaaatgg atggctgaag ttgatgtttt cctgaaagag gaatggcctg    300

ccctgggga tgctgaaatc ctgaaaaaac agctcaaaca atgcagagta agaagatctg    360

aattcctaca acttaaaaaa tgaacataat ggaataagga tattttaaat tattatgtta    420

aaatgttaag tatacttgga gttggtgaaa aaaaatcaat tcatttatac agacaatcca    480

agaaggtatg acacattact gttttcatag gaaaa                               515
```

```
<210> SEQ ID NO 53
<211> LENGTH: 671
<212> TYPE: DNA
<213> ORGANISM: Artificial Sequence
<220> FEATURE:
<223> OTHER INFORMATION: TS molecule AS2-E24-2XAS4

<400> SEQUENCE: 53

atatattttc agatttaaaa agaataagta tacaacatgg gatttttaga atcaacaaaa     60

aaattagtct ttatatgtcc tcacatcaca gaagtttctc ttactagtat ttaatttcca    120

gacttaggct attaaaataa ctactcaata ctcgagagat ctccgcggaa cattattata    180

acgttgctcg aatactaact gatatctctt cttttttttt ttccggaaaa cagaatcaca    240

taaaaacctt acagaaatgg atggctgaag ttgatgtttt cctgaaagag gaatggcctg    300

ccctggggga tgctgaaatc ctgaaaaaac agctcaaaca atgcagagta agaagatctg    360

aattcttagt tccatgtaat tcacaaaatc aagttataat tgtcttcttt tctaaaattt    420

atattgaaaa tacatgcatc acagaaaatt tccctttcaa tatgattaaa atgtggttaa    480

taactacaga tttaaaaaca attgactaaa tataagaatt cttagttcca tgtaattcac    540

aaaatcaagt tataattgtc ttcttttcta aaatttatat tgaaaataca tgcatcacag    600

aaaatttccc tttcaatatg attaaaatgt ggttaataac tacagattta aaaacaattg    660

actaaatata a                                                         671
```

```
<210> SEQ ID NO 54
<211> LENGTH: 543
<212> TYPE: DNA
<213> ORGANISM: Artificial Sequence
<220> FEATURE:
<223> OTHER INFORMATION: TS molecule AS2-E24-AS4 comprising DISE

<400> SEQUENCE: 54

atatattttc agatttaaaa agaataagta tacaacatgg gatttttaga atcaacaaaa     60

aaattagtct ttatatgtcc tcacatcaca gaagtttctc ttactagtat ttaatttcca    120

gacttaggct attaaaataa ctactcaata ctcgagagat ctccgcggaa cattattata    180

acgttgctcg aatactaact gatatctctt cttttttttt ttccggaaaa cagaatcaca    240

taaaaacctt acagaaatgg atggctgaag ttgatgtttt cctgaaagag gaatggcctg    300

ccctggggga tgctgaaatc ctgaaaaaac agctcaaaca atgcagagta agaacagctc    360

tttctttcca tgggttggcc tagatctgaa ttcttagttc catgtaattc acaaaatcaa    420

gttataattg tcttcttttc taaaatttat attgaaaata catgcatcac agaaaatttc    480

cctttcaata tgattaaaat gtggttaata actacagatt taaaaacaat tgactaaata    540
```

taa 543

<210> SEQ ID NO 55
<211> LENGTH: 537
<212> TYPE: DNA
<213> ORGANISM: Artificial Sequence
<220> FEATURE:
<223> OTHER INFORMATION: TS molecule AS2-E24-AS8 comprising DISE

<400> SEQUENCE: 55
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaacagctc 360
tttctttcca tgggttggcc tgaattccta caacttaaaa aatgaacata atggaataag 420
gatattttaa attattatgt taaaatgtta agtatacttg gagttggtga aaaaaaatca 480
attcatttat acagacaatc caagaaggta tgacacatta ctgttttcat aggaaaa 537

<210> SEQ ID NO 56
<211> LENGTH: 545
<212> TYPE: DNA
<213> ORGANISM: Artificial Sequence
<220> FEATURE:
<223> OTHER INFORMATION: TS molecule AS2-ISE-E24-AS4

<400> SEQUENCE: 56
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aaggctgagg gaaggactgt cctggggact ggtactaact gatatctctt 240
cttttttttt ttccggaaaa cagaatcaca taaaaacctt acagaaatgg atggctgaag 300
ttgatgtttt cctgaaagag gaatggcctg ccctggggga tgctgaaatc ctgaaaaaac 360
agctcaaaca atgcagagta agaagatctg aattcttagt tccatgtaat tcacaaaatc 420
aagttataat tgtcttcttt tctaaaattt atattgaaaa tacatgcatc acagaaaatt 480
tccctttcaa tatgattaaa atgtggttaa taactacaga tttaaaaaca attgactaaa 540
tataa 545

<210> SEQ ID NO 57
<211> LENGTH: 699
<212> TYPE: DNA
<213> ORGANISM: Artificial Sequence
<220> FEATURE:
<223> OTHER INFORMATION: TS molecule AS2-E24-DISE-2XAS4

<400> SEQUENCE: 57
atatattttc agatttaaaa agaataagta tacaacatgg gatttttaga atcaacaaaa 60
aaattagtct ttatatgtcc tcacatcaca gaagtttctc ttactagtat ttaatttcca 120
gacttaggct attaaaataa ctactcaata ctcgagagat ctccgcggaa cattattata 180
acgttgctcg aatactaact gatatctctt cttttttttt ttccggaaaa cagaatcaca 240
taaaaacctt acagaaatgg atggctgaag ttgatgtttt cctgaaagag gaatggcctg 300
ccctggggga tgctgaaatc ctgaaaaaac agctcaaaca atgcagagta agaacagctc 360
tttctttcca tgggttggcc tagatctgaa ttcttagttc catgtaattc acaaaatcaa 420
gttataattg tcttcttttc taaaatttat attgaaaata catgcatcac agaaaatttc 480
cctttcaata tgattaaaat gtggttaata actacagatt taaaaacaat tgactaaata 540
taagaattct tagttccatg taattcacaa aatcaagtta taattgtctt cttttctaaa 600
atttatattg aaaatacatg catcacagaa aatttccctt tcaatatgat taaaatgtgg 660
ttaataacta cagatttaaa aacaattgac taaatataa 699

<210> SEQ ID NO 58
<211> LENGTH: 164
<212> TYPE: DNA
<213> ORGANISM: Artificial Sequence
<220> FEATURE:
<223> OTHER INFORMATION: Antisense sequence AS3bis

<400> SEQUENCE: 58
agagcctcaa aattaaatag aagttcattt acactaacac gcatatttga tgagtttcat 60
tcatatcaag aagaaggtaa ataaaagttt atgtaattta gagatctaaa caaagtagaa 120
tatctgataa agcaatatat atgtattctt atgaataatt tcta 164

<210> SEQ ID NO 59
<211> LENGTH: 42
<212> TYPE: DNA
<213> ORGANISM: Artificial Sequence
<220> FEATURE:
<223> OTHER INFORMATION: Spacer sequence

<400> SEQUENCE: 59
ctcgagagat ctccgcggaa cattattata acgttgctcg aa 42

<210> SEQ ID NO 60
<211> LENGTH: 213
<212> TYPE: DNA
<213> ORGANISM: Homo sapiens
<220> FEATURE:
<221> NAME/KEY: misc_feature
<223> OTHER INFORMATION: Nucleotide sequence of the human dystrophin gene DMD, exon 23

<400> SEQUENCE: 60
gctttacaaa gttctctgca agagcaacaa agtggcctat actatctcag caccactgtg 60
aaagagatgt cgaagaaagc gccctctgaa attagccgga aatatcaatc agaatttgaa 120
gaaattgagg gacgctggaa gaagctctcc tcccagctgg ttgagcattg tcaaaagcta 180
gaggagcaaa tgaataaact ccgaaaaatt cag 213

<210> SEQ ID NO 61
<211> LENGTH: 3453
<212> TYPE: DNA
<213> ORGANISM: Homo sapiens
<220> FEATURE:
<221> NAME/KEY: misc_feature
<223> OTHER INFORMATION: Nucleotide sequence of the human dystrophin gene DMD, intron 22

<400> SEQUENCE: 61
gtctgtgaat atttgaatgt caaaacaata aagcacgctt atcaagcatt cacattgata 60
taacctttaa ataatattag aatttaagtc attctgacaa gtatggtagt ttgcccattg 120

-continued

```
agcaaatgaa aatgagactt tacagtatta tttatgcata tactctatct atggatatat    180
atgtatgggc atatatacat gctgtttttg aaaacaattg tatgatctat ttatgaagta    240
tatttttaat ttagcatgca ttttcagatg tattgatttt gattattaga aaaaccattg    300
ttttattccc cacctttgct tctttatttg taactcctgt cacattctca aactggtggg    360
taaaatcagt gtacagtcat cccttcgtat ccatggggaa gtggttccag gaactcctat    420
gaatatcaga attcacagat gttcaagtcc tttatatgaa tggtgtaata tttgcatata    480
acttatgaac atgctcccat atactttaac tcatctctgg attacttata atgcctaata    540
caatgtaaat attatgaaaa tatgtgttat actgtattat ttaggaagta gtgacaatga    600
aaaagtctta catgtttagt acagatgtag ttatttttgt caaatattat ctattagtag    660
ttgactgaat ccactcattc agaatccaca aatatggagg gctggctata tttataaaat    720
tggtttaaat ttaaacatta attttctgta atgtaatgag acatttgaat tctaatagct    780
acattttttt aacatccttc tatcaggaaa gatatactaa tatgggaaat gaaagaaata    840
atttgtaaga gattttataa tacttttcct actttatttt atttttagac ggagtttcat    900
tcttgttgcc caggctggag tgcagcagtg ctatctcggc tcactgcaac ctacgcctcc    960
cgggttcaag tgattctcct gccttagcct cctgagtagc tgggattata gtgcgtgcca   1020
tcacgcctgg ctaatttttg tatttttaaa gtaaagatgg ggtttcacca tcttggccat   1080
gctggtctca aactcctgac ctcagatgat ctgcctgcct cagcctccca aagtgctggg   1140
attacaggtg tgagccactg cgcccagccc ttttcctact tattataaaa tactacatta   1200
tatgttcaat aactttttat ttctgaagac atgaaaacgt attagttata tttagaagct   1260
gagataatat gtgcatttta agaaaaatgt ttaaaaattc aaatttaaac tttatcacat   1320
agaatttttt ttggataatt aaatattttt ttgaagtaat gtattcaaag aaaaatacat   1380
ttaaacaact ttcattatgt attgtcctat ttagatattt attctactac aataccaaat   1440
ggtagctgtt tcaccttttt tgtttccttt tgttgtggtt tttaatgctt ggcataatga   1500
ttccaaagtc tatctggaaa aatgtgttgc ctaatagaac tagtaaactt ttaaacataa   1560
gaataaaaat gtgcaagaat aagagtggag aaaacacaag aaaaggcagt tagatgagca   1620
gaagagacta tttccactga aaaagatagg aaagaaaata attgttcata aatattattg   1680
ggaaatgtat taactaacta aaaaaaaaga tatgaacatt tcccccaaag ttacaccaaa   1740
ataaaaacca catacaataa aatgttcaaa aaatgtgggg aagcccaaat tttggaaaat   1800
atttaaaata ataatgttat aaaaatttag gtggagaagc ataaaaatcg atggaaacaa   1860
tcacaaacat tgtaaaaaca ccagagacaa ttttaaagaa atatgatacc aaggaatctt   1920
tttttttctg tgagtaagga agaaagtctt gagtaaggta tcctccaaaa agagacatat   1980
atgaataata aacctatgaa taattgtaac ttaaattgta aaggaagaag taaaaaaatt   2040
acaagatgag aatttttttt gcatactaaa ttgcatacac acaaaagata taagtaccaa   2100
tttgcaagtg gtgaaataaa aattgtctct tactgctgga aatgtaaatt caatatgaat   2160
tttactgagg ttaactcttc agtgcatcct aataacatac aacattaata taatttccat   2220
gaaatctgta tctgatggaa ataatcagaa tacactcaaa gatgtaaatg gaactggaga   2280
tagataggat attgattgat tgagggatgg atggatggat tagataggta ggtagataga   2340
gataaacata atttacagga gtggaaaact agaaatgaat gtgtagaact aataatggaa   2400
attgttgaac tagaaaagcc attacaattt ttgtttttga aaaaataatt atttgacatg   2460
ggcaaatgct cacactaaaa cacctagctc aaagtgtagt tatatgctag atattgtcta   2520
```

```
aataatcagt catagggggaa caatttgaaa aagtgaaata aacttaaaaa agtaaagtaa   2580

aaaaacaaat taagtaccac caaataggca taggatacta tgaaactata aaacttagat   2640

atttgacaaa ttttgggttg atataggtca cattataggg gaaagaataa ctgtttatat   2700

gtgcatacat gatcatatat ttaatattta gctatacata gaacaaattg aaaatttata   2760

taaagtacta gtagttctgg tttttttttc catttttgtc atgagccttt attattttat   2820

aaagtaaaag taacattaaa gtaaatattg aacaggggaa gtctaaagtt atgatcctac   2880

tgtaagaaat tacatgtgtt atacagaata agtataaata aattttataa attctccaca   2940

aaactatcct tgaatcccac cataatacta cataacagaa taacattttt tgaaaatata   3000

ttaagtacat agattgttca ataagttttt ctattccata tatcaatatt attagctata   3060

gttttatgta gagtttactt tcctgaaagc tcagtataat taatttcaac tccattaact   3120

gtatcacaaa tgcagttatt aatatatata cttaattcag taaaattaga tgcaccaaaa   3180

ctttttggct ctgtaagata tagttttgag atatatttga cattgttcag aaaaatacat   3240

atggagtgtt aaataccact aaataatatt caagttactc ttaggataat atgtaaaatt   3300

taaattacca ctagaagttt ataactgata gaagatcatc tactttgttt acatgtttga   3360

atcatataga tttcaagtac agttaatttc actaaaactc atcaattatt attcatcaat   3420

tagggtaaat gtatttaaaa aattgttttt tag                                3453
```

<210> SEQ ID NO 62
<211> LENGTH: 3798
<212> TYPE: DNA
<213> ORGANISM: Homo sapiens
<220> FEATURE:
<221> NAME/KEY: misc_feature
<223> OTHER INFORMATION: Nucleotide sequence of the human dystrophin gene DMD, intron 23

<400> SEQUENCE: 62

```
gtaattcaag attttacttt ctaccctcat ttttatttac ttgtttttttc cctaacgata     60

cactgtaaac tgtaaaggta cataagcatt tgaccttcag catctttcaa agttagtgag    120

aagatgaaaa gacatgagtc ttttacaaag gatggcgatt tgcttattcc ttctaggaaa    180

agaataggag ttttctcagt gtttttagaa tgaattttct attttcacca ttaccaatag    240

gaattaaaca tgtttttagt ttaataattt tcaaaaccaa tcatccattt agtctggttg    300

tcttttaaga tacgggtaat catttagctt atgactagaa aaaagttatg tatatataca    360

ttatacagag gtatattgta atcattttat atatataatg tatagtatgt atatgattat    420

ttcctatatt acctttcatt tctgctgttt tgctacttat aaaaagtagg agtcaactat    480

gctgtctata tgtgctatta tatataaaat atggtgatat gttcataaaa ttgcattata    540

tattcatccc attatgtata actccatata tgtatatgtg cagtagaaat gtaggtgtat    600

taatgtccta tgatactcct aagaaattag cagaaattta atggcttcaa acaacacaaa    660

tttattacat tactgttctg gaggtcagaa gttcagaatt aatctctgtg ggctaaaatt    720

aaggtgttag cagaactgtg tctgttttgg agactttgaa agagaatgtg tgttattggc    780

atttttagct tccatatata tatgtatata tatacacaca catacatata acatgtatat    840

atgtgtgtat atatatatat atatacgtgt ataatggaat tatatatcat gtacatatat    900

acatatctaa tgtaatatat atcacatatg taacctgttg tatatgtata ttaatgttac    960

atatgtaata tatagtaata acttatttta tcaccatatc gaatttgtaa ttatatgctt   1020
```

```
aaattttacc acatcacctt cttcctgaaa ccaaattccc ttgacttaat ttgtttgaat   1080
agtgccacca tactaataac cactcaagct aaagaaaaac agtaaaccaa caattgcatt   1140
aaggtctaaa agcctaaaat attcaataag gtaagtaatg tgtcccttga gtggtcaatt   1200
attgtgacaa atgttaatgc tgggaaggaa atgtcgaaaa cgttatggta tgatggaaaa   1260
acattgcaac aatatgctcc tggatttaaa tcccagtcta gctgcttagt ttttgtgctt   1320
acctttttaca aaccaaagca ctaagcaaac ctaaaacatt ttttaatgca tagcatttct   1380
ttacttataa acatatgtgt acatgcatac ctatgtaaat actgcatgaa aatatctatt   1440
atttgtcaag accagtggcc taagagggca caattacatg gctcttgtta tcaaggagcc   1500
cacattctag tgaaggagga aggtaggtgt attcatttcc tatggcactc ctaacaaatt   1560
gccggaaatt taataacttc aagcaacaca aatttattag agttctggaa gtcaaaagtt   1620
caggattagt ctcagtgggc taaaattaag gtgtcagcag gactttgtct gttttggagg   1680
ctttgcgaca gagtctgttt tattggcatt tttagcttct agaagcattc cttgtctcat   1740
gtccccatcc tccatcttca aagtcagcag tgtaacatca tctagtgtca atttctctct   1800
ccctgtctat ctccctctcc ctctctttct acctctcctt ctcaccttcc tttccctatc   1860
ctgttccctg tgttgacttc cttttaatta ggacctttgt gattacatta tgccctggtg   1920
gatgatccag tataatctcc ccatctcaga atccttaatg taatcacatc tgcaaagtcc   1980
tttctggtaa tatactcaca ggtttcagag attagggtga ggacatcttg gggtagcat    2040
tattcagcct tgcatggtaa ataaattaaa cagtatggga aaggttgtca cagtaggcag   2100
gaaggaaatc caacataaac taggaaaaag gattatgaaa tattatcgga acataggttg   2160
tctctgctat agattaaata ggtagaattt agttagctaa taccgagaaa gaaagagttc   2220
ttgagaaagc atagcagcat tttcagttaa atgatataag ttcaacactg ggtagacaat   2280
atatatgggg attaataaaa tattatggtt ggaaaactgg attgagagta gacagtgaat   2340
gtccttggat gctatgtttt acaatctgag ttttaatcta gtggtgatgg gactgataat   2400
aataacaata aaaacttaat aagaaaaaac tgctattggt taaagaggga aataatatga   2460
ttccacttgt gttttcaaaa cattcccaag atgagaggaa ggaggagagg agattactgg   2520
catcactgta gatcagtaat tagaatgagg tgagaccgag gcagatatca aaacgagcca   2580
gtgcattaat ggagtcacta atgagacctg aacagcccag gcgtagtggc tcatgcctat   2640
aatcccagca ctctgggcag ctgaggcagg tagatcacga ggtcaagaga tcaagaccat   2700
gctggccaac atggcgaaac cctgtctcta ctaaaaacac aaaaattagc tgggcatggt   2760
agtgcacgcc tgtaatccca gctacttggg aggctgaggc aggagaatgg cgtgaacctg   2820
ggaggtggag gctgcagtga gccaagattg tgccacttca ctccagcctg ggcgacagag   2880
caagactcca tctcaaaaaa aaaaaaaaaa aaaaacaaaa aacaaacaaa aaaaaaaaga   2940
cctgaacaag gacagtgaag atgtgaaata agaacaaatg tagacttgaa agataacagc   3000
aaggtgatcg tcttgaagtt ctcttagata aatagtttaa aaattattat taataatcac   3060
attaaagggg aaactttctg tggagcacat attttcaatg taaatttaag taaaacagaa   3120
gaaaataaca catgtagaca gcatagttga atcatacttt ttagaagtgg caaaacagca   3180
gaaaaaaagg taatacggga aagaatcatg ggtgagagat actggctatt tataaatgat   3240
aaaagatgat gatttttacc tgatcattac ttcgtactgg tcagacaaat aaaagcaaaa   3300
gctctgtctt tgaagatgac aaaatattag tccaaaagtt cccaactgga aggactattt   3360
aaactgtcat ctgtagaaaa taatttgtga aagttcgggt ttagggaggc tataaagaca   3420
```

```
ccattacatt gagtttattg ttcatagttt gttttatgta ctgtaaggac acatttttag   3480

tattctcatg agttgttttg taacttaaaa tttctctaga gggggatatg atttaatgtt   3540

ctcgagagta acatcataaa accacatttg gtagtaattt tgtattttta acaatagcag   3600

acttcacaca ccagtgctca tacagtagac cataaaaatg cagtcttagt aaaaatattc   3660

tttgcctcaa gaactactta gagacatcct ttaaacatgg gaattgtttt tgggcctgtg   3720

tttagacata acacaatgat gaattgtgtt aaaagtaatc agcacaccag taatgcctta   3780

taacgggtct cgtttcag                                                  3798


<210> SEQ ID NO 63
<211> LENGTH: 71
<212> TYPE: PRT
<213> ORGANISM: Homo sapiens
<220> FEATURE:
<221> NAME/KEY: misc_feature
<223> OTHER INFORMATION: Human sequence of the dystrophin gene DMD,
      exon 23

<400> SEQUENCE: 63

Ala Leu Gln Ser Ser Leu Gln Glu Gln Gln Ser Gly Leu Tyr Tyr Leu
1               5                   10                  15

Ser Thr Thr Val Lys Glu Met Ser Lys Lys Ala Pro Ser Glu Ile Ser
            20                  25                  30

Arg Lys Tyr Gln Ser Glu Phe Glu Glu Ile Glu Gly Arg Trp Lys Lys
        35                  40                  45

Leu Ser Ser Gln Leu Val Glu His Cys Gln Lys Leu Glu Glu Gln Met
    50                  55                  60

Asn Lys Leu Arg Lys Ile Gln
65                  70


<210> SEQ ID NO 64
<211> LENGTH: 114
<212> TYPE: DNA
<213> ORGANISM: Homo sapiens
<220> FEATURE:
<221> NAME/KEY: misc_feature
<223> OTHER INFORMATION: Human nucleotide sequence of the dystrophin
      gene DMD, exon 24

<400> SEQUENCE: 64

aatcacatac aaaccctgaa gaaatggatg gctgaagttg atgtttttct gaaggaggaa     60

tggcctgccc ttggggattc agaaattcta aaaaagcagc tgaaacagtg caga          114


<210> SEQ ID NO 65
<211> LENGTH: 38
<212> TYPE: PRT
<213> ORGANISM: Homo sapiens
<220> FEATURE:
<221> NAME/KEY: misc_feature
<223> OTHER INFORMATION: Human sequence of the dystrophin gene DMD,
      exon 24

<400> SEQUENCE: 65

Asn His Ile Gln Thr Leu Lys Lys Trp Met Ala Glu Val Asp Val Phe
1               5                   10                  15

Leu Lys Glu Glu Trp Pro Ala Leu Gly Asp Ser Glu Ile Leu Lys Lys
            20                  25                  30

Gln Leu Lys Gln Cys Arg
        35
```

<210> SEQ ID NO 66
<211> LENGTH: 608
<212> TYPE: DNA
<213> ORGANISM: Mus musculus
<220> FEATURE:
<221> NAME/KEY: misc_feature
<223> OTHER INFORMATION: Murine sequence of the dystrophin gene DMD, intron 58

<400> SEQUENCE: 66
gtaattgaat gtggaactgt aataacatat tgatagaggg ctcagtgatg agagcacagc 60
ccatccatgc ttgctgccag agtctgtata gctctcacac ttcagggtta aacagaatca 120
attcaaatta aatgtaggtg ctgaaaaaga atacagaatc acaaaccacc atgcacaatt 180
ctgttttcag tcataaataa agcaatcaat gatcagttat ttgaatattt agaaaatggt 240
aagcaaaaga tcttatctgt gataagaagt tctattgtta caaagactgc aagctaattt 300
tccgtttaag ctgactgaaa taaattggag ctgttcagca catgctaaca tttttctctc 360
tgaaagctta aatgaatctt gatttacctg attgacagaa agtagaacag attcactaag 420
gaagacagtt tagctgtgct tgactatatc aaaatttatg ccaaagtgta aaagagccat 480
taatcagtaa gttggcctcg tgttaatcta tattcctttc ctttcttcta gtctgacctt 540
ttcaaccatg ttttttttt ttaacaaaaa tggatgtgac cttaaacctt gtcatattgc 600
caatttag 608

<210> SEQ ID NO 67
<211> LENGTH: 608
<212> TYPE: DNA
<213> ORGANISM: Homo sapiens
<220> FEATURE:
<221> NAME/KEY: misc_feature
<223> OTHER INFORMATION: Human sequence of the dystrophin gene DMD, intron 58

<400> SEQUENCE: 67
gtaattgaat gtggaactat aataacatat tgatagaagg atcagtggtg acggagcagc 60
ccatccattc ttgctgccag ggtctggata gctctcatat tttcttggtt aaatagaatc 120
aattcaaatt aaacatagat gctgaaaaaa aaataaggac tcataaacta ccatgcataa 180
atcagtttgt gcattcataa ataaacatca aaagagatta gcaatcagtt attggaacat 240
ttagaaaata ataaacaaag ggagttatct gtgaggagga attctattgt tgcaaagact 300
acaagttaat tttccattta agagcctgcc tgaagtaaat tagagcttgt ggtatgcatc 360
ctaacgtttt tctcctcaat agcttaagtg aatcttaaat tgtcggattg atataaggta 420
gaaactcagg aagatatact ttagatgttc tgggctgtat caaaatttat gccaaagtat 480
aaaaaagccg ttaatcagta ggttaccctc ttgttcaact gtactctttc tttcttccag 540
tatgaccttt ttgacaatgt ttaaaaaaaa agaatgtggc ctaaaacctt gtcatattgc 600
caatttag 608

<210> SEQ ID NO 68
<211> LENGTH: 150
<212> TYPE: DNA
<213> ORGANISM: Artificial Sequence
<220> FEATURE:
<223> OTHER INFORMATION: Antisens sequence to intron 58 of DMD

<400> SEQUENCE: 68
aaaattaact tgtagtcttt gcaacaatag aattcctcct cacagataac tccctttgtt 60
tattattttc taaatgttcc aataactgat tgctaatctc ttttgatgtt tatttatgaa 120
tgcacaaact gatttatgca tggtagttta 150

<210> SEQ ID NO 69
<211> LENGTH: 2390
<212> TYPE: DNA
<213> ORGANISM: Mus musculus
<220> FEATURE:
<221> NAME/KEY: misc_feature
<223> OTHER INFORMATION: Murine sequence of the dystrophin gene DMD, exons 59-79

<400> SEQUENCE: 69
aactgcctcc tgaagaaaga gctcagaatg tcactcggct cctacgaaag caggctgaag 60
aggtcaacgc tgaatgggac aaattgaacc tgcgctcagc tgattggcag agaaaaatag 120
atgaagctct tgaaagactc caggaacttc aggaagctgc cgatgaactg gacctcaagt 180
tgcgccaagc tgaggtgatc aagggatcct ggcagccagt gggggatctc ctcattgact 240
ctctgcaaga tcaccttgaa aaagtcaagg cacttcgggg agaaattgca cctcttaaag 300
agaatgtcaa tcgtgtcaat gaccttgcac atcagctgac cacactgggc attcagctct 360
caccttataa cctcagcact ttggaagatc tgaataccag atggaggctt ctacaggtgg 420
ctgtggagga ccgtgtcaga cagctgcatg aagcccacag ggactttggt cctgcatccc 480
agcacttcct ttccacttca gttcagggtc cctgggagag agccatctca ccaaacaaag 540
tgccctacta tatcaaccac gagacccaaa ccacttgttg ggaccacccc aaaatgacag 600
agctctacca gtctttagct gacctgaata atgtcaggtt ctccgcgtat aggactgcca 660
tgaagctcag aaggctccag aaggcccttt gcttggatct cttgagcctg tcagctgcat 720
gtgatgccct ggaccagcac aacctcaagc aaaatgacca gcccatggat atcctgcaga 780
taattaactg tttgactaca atttatgatc gtctggagca agagcacaac aatctggtca 840
atgtccctct ctgtgtggat atgtgtctca actggcttct caatgtttat gatacgggac 900
gaacagggag gatccgtgtc ctgtctttta aaactggcat catttctctg tgtaaagcac 960
acttggaaga caagtacaga taccttttca agcaagtggc aagttcaact ggcttttgtg 1020
accagcgtag gctgggtctt cttctgcatg attctattca aatcccaaga cagttgggtg 1080
aagttgcttc ctttgggggc agtaacattg agccgagtgt caggagctgc ttccaatttg 1140
ccaataataa acctgagatt gaagctgctc tcttccttga ctggatgcgc ctggaacccc 1200
agtctatggt gtggctgccc gtcttgcaca gagtggctgc tgctgaaact gccaagcatc 1260
aagccaagtg taacatctgt aaggagtgtc caatcattgg attcaggtac agaagcctaa 1320
agcattttaa ttatgacatc tgccaaagtt gctttttttc tggccgagtt gcaaagggcc 1380
ataaaatgca ctaccccatg gtagagtatt gcactccgac tacatccgga gaagatgttc 1440
gcgacttcgc caaggtacta aaaaacaaat ttcgaaccaa aaggtatttt gcgaagcatc 1500
cccgaatggg ctacctgcca gtgcagactg tgttagaggg ggacaacatg gaaactcccg 1560
ttactctgat caacttctgg ccagtagatt ctgcgcctgc ctcgtccccc cagctttcac 1620
acgatgatac tcattcacgc attgaacatt atgctagcag gctagcagaa atggaaaaca 1680
gcaatggatc ttatctaaat gatagcatct ctcctaatga gagcatagat gatgaacatt 1740
tgttaatcca gcattactgc caaagtttga accaggactc ccccctgagc cagcctcgta 1800
gtcctgccca gatcttgatt tccttagaga gtgaggaaag aggggagcta gagagaatcc 1860

-continued tagcagatct tgaggaagaa aacaggaatc tgcaagcaga atatgatcgc ctgaagcagc 1920
agcatgagca taaaggcctg tctccactgc catctcctcc tgagatgatg cccacctctc 1980
ctcagagtcc cagggatgct gagctcattg ctgaggctaa gctactgcgc caacacaaag 2040
gacgcctgga agccaggatg caaatcctgg aagaccacaa taaacagctg gagtctcagt 2100
tacatagact gagacagctc ctggagcagc cccaggctga agctaaggtg aatggcacca 2160
cggtgtcctc tccttccacc tctctgcaga ggtcagatag cagtcagcct atgctgctcc 2220
gagtggttgg cagtcaaact tcagaatcta tgggtgagga agatcttctg agtcctcccc 2280
aggacacaag cacagggtta gaagaagtga tggagcaact caacaactcc ttccctagtt 2340
caagaggaag aaatgccccc ggaaagccaa tgagagagga cacaatgtag 2390

<210> SEQ ID NO 70
<211> LENGTH: 2390
<212> TYPE: DNA
<213> ORGANISM: Homo sapiens
<220> FEATURE:
<221> NAME/KEY: misc_feature
<223> OTHER INFORMATION: Human sequence of the dystrophin gene DMD, exons 59-79

<400> SEQUENCE: 70
agctgcctcc tgaggagaga gcccagaatg tcactcggct tctacgaaag caggctgagg 60
aggtcaatac tgagtgggaa aaattgaacc tgcactccgc tgactggcag agaaaaatag 120
atgagaccct tgaaagactc caggaacttc aagaggccac ggatgagctg gacctcaagc 180
tgcgccaagc tgaggtgatc aagggatcct ggcagcccgt gggcgatctc ctcattgact 240
ctctccaaga tcacctcgag aaagtcaagg cacttcgagg agaaattgcg cctctgaaag 300
agaacgtgag ccacgtcaat gaccttgctc gccagcttac cactttgggc attcagctct 360
caccgtataa cctcagcact ctggaagacc tgaacaccag atggaagctt ctgcaggtgg 420
ccgtcgagga ccgagtcagg cagctgcatg aagcccacag ggactttggt ccagcatctc 480
agcactttct ttccacgtct gtccagggtc cctgggagag agccatctcg ccaaacaaag 540
tgccctacta tatcaaccac gagactcaaa caacttgctg ggaccatccc aaaatgacag 600
agctctacca gtctttagct gacctgaata atgtcagatt ctcagcttat aggactgcca 660
tgaaactccg aagactgcag aaggcccttt gcttggatct cttgagcctg tcagctgcat 720
gtgatgcctt ggaccagcac aacctcaagc aaaatgacca gcccatggat atcctgcaga 780
ttattaattg tttgaccact atttatgacc gcctggagca agagcacaac aatttggtca 840
acgtccctct ctgcgtggat atgtgtctga actggctgct gaatgtttat gatacgggac 900
gaacagggag gatccgtgtc ctgtctttta aaactggcat catttccctg tgtaaagcac 960
atttggaaga caagtacaga taccttttca agcaagtggc aagttcaaca ggattttgtg 1020
accagcgcag gctgggcctc cttctgcatg attctatcca aattccaaga cagttgggtg 1080
aagttgcatc ctttgggggc agtaacattg agccaagtgt ccggagctgc ttccaatttg 1140
ctaataataa gccagagatc gaagcggccc tcttcctaga ctggatgaga ctggaacccc 1200
agtccatggt gtggctgccc gtcctgcaca gagtggctgc tgcagaaact gccaagcatc 1260
aggccaaatg taacatctgc aaagagtgtc caatcattgg attcaggtac aggagtctaa 1320
agcactttaa ttatgacatc tgccaaagct gctttttttc tggtcgagtt gcaaaaggcc 1380
ataaaatgca ctatcccatg gtggaatatt gcactccgac tacatcagga gaagatgttc 1440
gagactttgc caaggtacta aaaaacaaat ttcgaaccaa aaggtatttt gcgaagcatc 1500

```
cccgaatggg ctacctgcca gtgcagactg tcttagaggg ggacaacatg gaaactcccg   1560
ttactctgat caacttctgg ccagtagatt ctgcgcctgc ctcgtcccct cagctttcac   1620
acgatgatac tcattcacgc attgaacatt atgctagcag gctagcagaa atggaaaaca   1680
gcaatggatc ttatctaaat gatagcatct ctcctaatga gagcatagat gatgaacatt   1740
tgttaatcca gcattactgc caaagtttga accaggactc ccccctgagc cagcctcgta   1800
gtcctgccca gatcttgatt tccttagaga gtgaggaaag aggggagcta gagagaatcc   1860
tagcagatct tgaggaagaa aacaggaatc tgcaagcaga atatgaccgt ctaaagcagc   1920
agcacgaaca taaaggcctg tccccactgc cgtcccctcc tgaaatgatg cccacctctc   1980
cccagagtcc ccgggatgct gagctcattg ctgaggccaa gctactgcgt caacacaaag   2040
gccgcctgga agccaggatg caaatcctgg aagaccacaa taaacagctg gagtcacagt   2100
tacacaggct aaggcagctg ctggagcaac cccaggcaga ggccaaagtg aatggcacaa   2160
cggtgtcctc tccttctacc tctctacaga ggtccgacag cagtcagcct atgctgctcc   2220
gagtggttgg cagtcaaact tcggactcca tgggtgagga agatcttctc agtcctcccc   2280
aggacacaag cacagggtta gaggaggtga tggagcaact caacaactcc ttccctagtt   2340
caagaggaag aaatacccct ggaaagccaa tgagagagga cacaatgtag             2390
```

```
<210> SEQ ID NO 71
<211> LENGTH: 2617
<212> TYPE: DNA
<213> ORGANISM: Artificial Sequence
<220> FEATURE:
<223> OTHER INFORMATION: Simple PTM

<400> SEQUENCE: 71

aaaattaact tgtagtcttt gcaacaatag aattcctcct cacagataac tccctttgtt     60
tattattttc taaatgttcc aataactgat tgctaatctc ttttgatgtt tatttatgaa    120
tgcacaaact gatttatgca tggtagttta ggtaccccgc ggaacattat tataacgttg    180
ctcgaatact aactgatatc tcttcttttt ttttttccgg aaaacagagc tgcctcctga    240
ggagagagcc cagaatgtca ctcggcttct acgaaagcag gctgaggagg tcaatactga    300
gtgggaaaaa ttgaacctgc actccgctga ctggcagaga aaaatagatg agacccttga    360
aagactccag gaacttcaag aggccacgga tgagctggac ctcaagctgc gccaagctga    420
ggtgatcaag ggatcctggc agcccgtggg cgatctcctc attgactctc tccaagatca    480
cctcgagaaa gtcaaggcac ttcgaggaga aattgcgcct ctgaaagaga acgtgagcca    540
cgtcaatgac cttgctcgcc agcttaccac tttgggcatt cagctctcac cgtataacct    600
cagcactctg gaagacctga acaccagatg gaagcttctg caggtggccg tcgaggaccg    660
agtcaggcag ctgcatgaag cccacaggga ctttggtcca gcatctcagc actttctttc    720
cacgtctgtc cagggtccct gggagagagc catctcgcca aacaaagtgc cctactatat    780
caaccacgag actcaaacaa cttgctggga ccatcccaaa atgacagagc tctaccagtc    840
tttagctgac ctgaataatg tcagattctc agcttatagg actgccatga aactccgaag    900
actgcagaag gccctttgct tggatctctt gagcctgtca gctgcatgtg atgccttgga    960
ccagcacaac ctcaagcaaa atgaccagcc catggatatc ctgcagatta ttaattgttt   1020
gaccactatt tatgaccgcc tggagcaaga gcacaacaat ttggtcaacg tccctctctg   1080
cgtggatatg tgtctgaact ggctgctgaa tgtttatgat acgggacgaa cagggaggat   1140
```

-continued

```
ccgtgtcctg tcttttaaaa ctggcatcat ttccctgtgt aaagcacatt tggaagacaa   1200

gtacagatac cttttcaagc aagtggcaag ttcaacagga ttttgtgacc agcgcaggct   1260

gggcctcctt ctgcatgatt ctatccaaat tccaagacag ttgggtgaag ttgcatcctt   1320

tgggggcagt aacattgagc caagtgtccg gagctgcttc caatttgcta ataataagcc   1380

agagatcgaa gcggccctct tcctagactg gatgagactg gaaccccagt ccatggtgtg   1440

gctgcccgtc ctgcacagag tggctgctgc agaaactgcc aagcatcagg ccaaatgtaa   1500

catctgcaaa gagtgtccaa tcattggatt caggtacagg agtctaaagc actttaatta   1560

tgacatctgc caaagctgct ttttttctgg tcgagttgca aaaggccata aaatgcacta   1620

tcccatggtg gaatattgca ctccgactac atcaggagaa gatgttcgag actttgccaa   1680

ggtactaaaa aacaaatttc gaaccaaaag gtattttgcg aagcatcccc gaatgggcta   1740

cctgccagtg cagactgtct tagaggggga caacatggaa actcccgtta ctctgatcaa   1800

cttctggcca gtagattctg cgcctgcctc gtcccctcag ctttcacacg atgatactca   1860

ttcacgcatt gaacattatg ctagcaggct agcagaaatg gaaaacagca atggatctta   1920

tctaaatgat agcatctctc ctaatgagag catagatgat gaacatttgt taatccagca   1980

ttactgccaa agtttgaacc aggactcccc cctgagccag cctcgtagtc ctgcccagat   2040

cttgatttcc ttagagagtg aggaaagagg ggagctagag agaatcctag cagatcttga   2100

ggaagaaaac aggaatctgc aagcagaata tgaccgtcta aagcagcagc acgaacataa   2160

aggcctgtcc ccactgccgt cccctcctga aatgatgccc acctctcccc agagtccccg   2220

ggatgctgag ctcattgctg aggccaagct actgcgtcaa cacaaaggcc gcctggaagc   2280

caggatgcaa atcctggaag accacaataa acagctggag tcacagttac acaggctaag   2340

gcagctgctg gagcaacccc aggcagaggc caaagtgaat ggcacaacgg tgtcctctcc   2400

ttctacctct ctacagaggt ccgacagcag tcagcctatg ctgctccgag tggttggcag   2460

tcaaacttcg gactccatgg gtgaggaaga tcttctcagt cctccccagg acacaagcac   2520

agggttagag gaggtgatgg agcaactcaa caactccttc cctagttcaa gaggaagaaa   2580

tacccctgga aagccaatga gagaggacac aatgtag                            2617
```

<210> SEQ ID NO 72
<211> LENGTH: 137
<212> TYPE: DNA
<213> ORGANISM: Homo sapiens
<220> FEATURE:
<221> NAME/KEY: misc_feature
<223> OTHER INFORMATION: Human sequence of the dystrophin gene DMD, exon 70

<400> SEQUENCE: 72

```
actacatcag gagaagatgt tcgagacttt gccaaggtac taaaaaacaa atttcgaacc     60

aaaaggtatt ttgcgaagca tccccgaatg ggctacctgc cagtgcagac tgtcttagag    120

ggggacaaca tggaaac                                                   137
```

<210> SEQ ID NO 73
<211> LENGTH: 137
<212> TYPE: DNA
<213> ORGANISM: Mus musculus
<220> FEATURE:
<221> NAME/KEY: misc_feature
<223> OTHER INFORMATION: Murine sequence of the dystrophin gene DMD, exon 70

<400> SEQUENCE: 73

-continued

```
actacatccg gagaagatgt tcgcgacttc gccaaggtac taaaaaacaa atttcgaacc      60

aaaaggtatt ttgcgaagca tccccgaatg ggctacctgc cagtgcagac tgtgttagag     120

ggggacaaca tggaaac                                                    137
```